(12) United States Patent
Angiolini et al.

(10) Patent No.: US 10,336,707 B2
(45) Date of Patent: Jul. 2, 2019

(54) HETEROCYCLIC DERIVATIVES MODULATING ACTIVITY OF CERTAIN PROTEIN KINASES

(71) Applicants: EUDENDRON S.R.L., Varese (IT); UNIVERSITA' DEGLI STUDI DI MILANO, Milan (IT)

(72) Inventors: Mauro Angiolini, Varese (IT); Fabio Zuccotto, Varese (IT); Anna Bernardi, Milan (IT); Francesco Airaghi, Milan (IT)

(73) Assignees: EUDENDRON S.R.L., Varese (IT); UNIVERSITA' DEGLI STUDI DI MILANO, Milan (IT)

( * ) Notice: Subject to any disclaimer, the term of this patent is extended or adjusted under 35 U.S.C. 154(b) by 0 days.

(21) Appl. No.: 15/535,054

(22) PCT Filed: Dec. 14, 2015

(86) PCT No.: PCT/EP2015/079572
§ 371 (c)(1),
(2) Date: Jun. 11, 2017

(87) PCT Pub. No.: WO2016/096709
PCT Pub. Date: Jun. 23, 2016

(65) Prior Publication Data
US 2018/0118691 A1    May 3, 2018

(30) Foreign Application Priority Data
Dec. 16, 2014  (IT) .............. MI2014A2156

(51) Int. Cl.
*C07D 231/56*  (2006.01)
*C07D 405/14*  (2006.01)
*C07D 403/14*  (2006.01)
*C07D 403/12*  (2006.01)
*C07D 405/12*  (2006.01)
*A61P 25/28*  (2006.01)
*A61P 29/00*  (2006.01)
*A61P 35/00*  (2006.01)
*C07D 261/20*  (2006.01)

(52) U.S. Cl.
CPC ........... *C07D 231/56* (2013.01); *A61P 25/28* (2018.01); *A61P 29/00* (2018.01); *A61P 35/00* (2018.01); *C07D 261/20* (2013.01); *C07D 403/12* (2013.01); *C07D 403/14* (2013.01); *C07D 405/12* (2013.01); *C07D 405/14* (2013.01)

(58) Field of Classification Search
CPC .. C07D 231/56; C07D 405/14; C07D 403/14; C07D 403/12
See application file for complete search history.

(56) References Cited

FOREIGN PATENT DOCUMENTS

| WO | 2003097610 A1 | 11/2003 | |
|---|---|---|---|
| WO | 2005073224 A2 | 8/2005 | |
| WO | 2006122799 A1 | 11/2006 | |
| WO | 2009013126 A1 | 1/2009 | |
| WO | WO-2016188214 A1 | * 12/2016 | ........... C07D 403/12 |

OTHER PUBLICATIONS

Chinese Patent Priority Document No. 201510279568.6, filed May 27, 2015 (Year: 2015).*
Sheridan, R.P. J. Chem. Inf. Comput. Sci. 2002, 42, 103-108 (Year: 2002).*
Antonysamy S., et al. "Fragment-based discovery of JAK-2 inhibitors,"Bioorg. Med. Chem. Lett. 19 (2009) 279-282.
Medina et al., "Structure-Based design of potent and selective 3-phosphoinositide-dependent kinase-1 (PDK1) inhibitors", J. Med. Chem. vol. 54, No. 6, Feb. 22, 2011, pp. 1871-1895.
Medina J. R., "Selective 3-Phosphoinositide-Dependent Kinase 1 (PDK1) Inhibitors: Dissecting the Function and Pharmacology of PDK1," J. Med. Chem. 2013, 56, 2726-2737.
Search Report and Written Opinion of PCT/EP2015/079572 dated Mar. 9, 2016.
Witherington J., et al., "6-Heteroaryl-pyrazolo[3,4-b]pyridines: Potent and Selective Inhibitors of Glycogen Synthase Kinase-3 (GSK-3)", J. Bioorg. Med. Chem. Lett. 13 (2003) 3059-3062.

* cited by examiner

*Primary Examiner* — Matthew P Coughlin
(74) *Attorney, Agent, or Firm* — Silvia Salvadori, P.C.; Silvia Salvadori

(57) ABSTRACT

The present invention relates to novel heterocyclic derivatives having general formula (I) and their therapeutic use for diseases such as cancer, inflammation, pain, autoimmune diseases or neurodegenerative diseases like Alzheimer's or Parkinson's disease that can be treated by modulation of certain protein kinases. Compounds of formula (I) can be used for treatment of patients who do not respond to kinase inhibition therapy that comprises currently available medications.

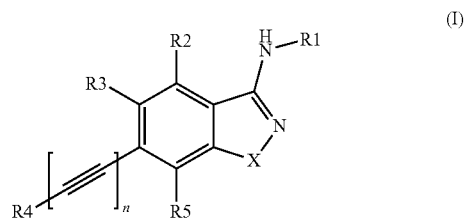

16 Claims, No Drawings

HETEROCYCLIC DERIVATIVES MODULATING ACTIVITY OF CERTAIN PROTEIN KINASES

This application is a U.S. national stage of PCT/EP2015/079572 filed on 14 Dec. 2015, which claims priority to and the benefit of Italian Application No. MI2014A002156 filed on 16 Dec. 2014.

FIELD OF THE INVENTION

The present invention relates to certain heterocyclic derivatives containing the indazole or benzoxazole bicyclic system that modulate the biological activity of certain protein kinases and their mutations. Such compounds and their pharmaceutical compositions are therefore useful for the treatment of diseases caused by dysregulation of protein kinases or for the treatment of diseases associated to resistant mutations of protein kinases. The present invention provides as well methods for the preparation of such compounds, pharmaceutical compositions containing such compounds and methods of treating diseases using pharmaceutical compositions containing such compounds.

BACKGROUND OF THE INVENTION

Protein kinases are a family of enzymes that catalyze the transfer of a phosphate group from ATP to the hydroxyl groups on tyrosine or serine/threonine residues of a client protein regulating several signal transduction pathways and crucial biological processes like cell proliferation, differentiation, survival, invasion and migration.

Up today, more than 500 members of the human protein kinase family have been discovered and classified into several subgroups. Certain human diseases, and more specifically cancers, are characterized by overexpression, amplification, mutations or rearrangements that induce aberrant activity of one or more protein kinases. The evident correlation between cancer development and dysregulation of protein kinases triggered the research of novel therapeutics for the modulation of biological activity of this class of proteins. First generation of approved protein kinase inhibitors provided potent drugs and successful clinical response during the treatment of some type of cancer. However, for a percentage of patients, therapeutic use of protein kinase inhibitors is very often associated to drug resistance leading to disease relapse. Drug resistance is mediated by several mechanisms such as secondary point mutations, activation of alternative survival and proliferation signaling pathways or gene amplification. Mutations of specific residues in the target kinase following a prolonged administration of an inhibitor represent the most relevant factors in acquiring drug resistance. Following kinase inhibitor treatment, amongst others, a frequently observed mutation is the one of the so called gatekeeper residue in the ATP binding site. For example within the protein kinase ALK, mutation from leucine to methionine of the gatekeeper residue L1196 confers drug resistance in about 30% of patients treated with Crizotinib, the drug approved by FDA as first line treatment of ALK positive non-small cell lung cancer. Development of drug resistance is thus a major limitation of currently available medications and the need for compounds useful to treat disease relapse is strongly emerging.

Amongst protein kinases heavily involved in human diseases, it is worth mentioning kinases such as ALK, RET, ROS1, $DDR_2$, $DDR_1$, PDGFR, EPHA2, EPHA3, EphB2, EphB4, ABL, KIT, $FGFR_2$, $FGFR_3$, VEFGR, IGF1R, p38α, JNK1, AXL, CDK2, CDKS, FLT3, MET, MER, MAP4K2, TYK2, RON, BRAF, TIE2, JAK1, JAK2, JAK3, IRAK4, IRAK1, EGFR, CSF1R, HCK, NIK, LCK, $HER_2$, $HER_3$, $HER_4$, LYN, SRC, PKC6, RIPK2, BTK, CAMKK2, FGR, TRKA, TRKB and TRKC. These proteins show a leading role or cause oncogene addiction in several human cancers or in central nervous system and metabolic diseases like leukemia, breast cancer, prostate cancer, neuroblastoma, lung cancer, melanoma, thyroid cancer, medulloblastoma, pancreas cancer, lymphoma, Parkinson's disease, Alzheimer's disease.

Amongst mentioned protein kinases, the anaplastic lymphoma kinase ALK is regarded as a particularly relevant therapeutic target because is responsible for certain cancer pathologies. ALK is a transmembrane receptor tyrosine-kinase protein belonging to the superfamily of insulin receptor. The structure of ALK, the oncogenic activation and pharmacological inhibition are deeply discussed in *Pharmacological Research* (2013), 68(1): 68-94.

The ALK kinase is essentially expressed in the central and peripheral nervous system. ALK is constituted by a long extra-cellular domain (1020 amino-acid residues in humans), a 21 residues trans-membrane domain and a 561 residues intracellular tyrosine catalytic domain. ALK plays a relevant role during embryo development and its role decreases after birth. An aberrant activity of ALK kinase associated to specific gene translocations, point mutations, gene amplification and/or overexpression is clearly linked to cancer development such as non-small cell lung cancer (NSCLC), anaplastic large cell lymphoma (ALCL), inflammatory myofibroblastic tumors (IMT), melanoma, glioblastoma, thyroid carcinoma, colorectal cancer and neuroblastoma.

The ALK catalytic domain was initially identified in ALCL cancer cells where the fusion protein NPM-ALK was observed. This fusion protein is the result of a translocation between the NPM1 and the ALK proteins. About 80% of all ALCL patients are characterized by the presence of the NPM-ALK fusion protein. Several other oncogenic fusion proteins involving ALK protein have been identified like TPM3-ALK in 12%-18% of inflammatory myofibroblastic tumors or the EML4-ALK in about 5% of NSCLC.

The amino terminal dimerization of ALK fusion proteins takes place in the cellular cytoplasm triggering the kinase domain activation which in turn causes the aberrant phosphorylation of intracellular substrates involved in proliferation (RAS/RAF/MEK/ERK) and survival (JAK/STAT, PI3/AKT). In addition, more than 20 activating point mutations have been identified in the pathogenesis of pediatric neuroblastoma associated to overexpression and/or amplification of ALK protein.

High level of mutated ALK protein and its fusion proteins in cancer tissues and low level in normal human tissues make the ALK protein an attractive target for the discovery of novel anti-cancer agents. A few ALK inhibitors have already been approved by FDA and many others are under clinical investigation. Amongst them Crizotinib is the first ALK inhibitor approved in 2011 by FDA for the treatment of ALK positive NSCLC patients. However, in about 30% of treated patients with Crizotinib, development of drug resistance has been observed. Most common cause of drug resistance is the mutation of the ALK gatekeeper residue L1196M that impairs the clinical efficacy of Crizotinib. Recent patents on ALK inhibitors are reported in *Expert Opinion Therapeutic Patents*, (2014) 24(4): 417-442).

In a certain percentage of NSCLC, genetic rearrangements involving the gene ROS1, which encodes the receptor tyrosine kinase ROS1 (ROS proto-oncogene 1 receptor tyrosine kinase), have been reported as well. The protein kinase ROS1, which belongs to the superfamily of insulin receptor, may function as a receptor for cell growth or differentiation factors. The approved ALK inhibitor Crizotinib targets in vitro also the ROS1 kinase. In clinical trials Crizotinib showed efficacy in patients ROS1 positive affected by NSCLC (*J. Clin. Oncol.* 2012, 30: 863-870; *N. Engl. J. Med.* 2014, 371: 1963-71). Like observed for ALK positive treated patients, also with kinase ROS1 resistance to Crizotinib therapy caused by mutations has been observed during clinical development. For example, mutations G2032R and L2026M have been detected in patients refractory to Crizotinib therapy. Protein kinase ROS1 is also expressed both in wild-type or mutated forms in several other tumors like glioblastoma, breast, liver, colon, kidney and stomach cancer. Moreover at least five oncogenic fusion proteins with the kinase ROS1 have been reported (*Med. Res. Rev.* 2011, 31(5): 794-818).

The rearranged during transfection proto-oncogene encodes the transmembrane receptor tyrosine kinase RET, a protein involved in several human cancers. Oncogenic mutations and rearrangements of RET kinase have been discovered in leukemia, thyroid, colon and lung cancer. RET fusion proteins in lung cancer have been described for the first time in 2012 making the RET kinase a relevant and novel target for a subpopulation of patients like the ALK and ROS1 protein kinases (*Nat. Med.* 2012, 18 (3), 382-384). Overexpression of RET kinase has been reported also in breast, pancreas and brain cancer. Resistance causing mutations have been described also for RET kinase with the frequent mutation of the gatekeeper residue V804M (*Nat. Rev. Cancer,* 2014, 14, 173-186).

Discoidin domain receptor 1 ($DDR_1$) and discoidin domain receptor 2 ($DDR_2$) are transmembrane protein receptor tyrosine kinases that play a crucial role in cancer development. $DDR_1$ and $DDR_2$ interact with collagens, important components of the extracellular matrix that directs crucial cellular processes like migration, motility, proliferation and differentiation. Dysregulation of $DDR_1$ and $DDR_2$ have been linked to diseases like fibrotic disorders, osteoarthritis and various types of cancers. Recently mutations of $DDR_2$ protein kinase have been described as oncogenic drivers in about 4% of patients with lung squamous cell carcinoma (SCC). Mutations L239R and I638F are selectively sensitive to the non-selective $DDR_2$ kinase inhibitor Dasatinib. Two patients with SCC carrying the mutation S768R exhibited a significant shrinkage of tumor size after treatment with Dasatinib (*J. Med: Chem.* 2015, (58), 3287-3301). Metastatic development is also strongly sustained by $DDR_1$ and $DDR_2$ protein kinases (*Cancer Metastasis Rev.* 2012, 31 (1-2), 295-321). In ductal breast carcinoma high expression of $DDR_2$ has been described as the driver of metastatic process (*Nat. Cell Biol.* 2013, 15, 677-687). Acquired resistance to Dasatinib treatment has been observed in $DDR_2$-dependent lung cancer cell lines where the mutation T654I of the gatekeeper residue has been described as responsible for drug resistance (*Mol. Cancer Ther.* 2014, 13, 475-482).

Erythropoietin-producing hepatocellular carcinoma receptor tyrosine kinases A and B (EphA, EphB receptors) are involved in various cellular signaling network with their ligands ephrins. EphA/EphB have been reported to be highly expressed in several type of cancer like melanoma, neuroblastoma, glioblastoma, prostate, lung, colon, thyroid, liver, breast and ovarian cancer (*J. Cell. Mol. Med.* 2012, 16 (12), 2894-2909). Particular interest is focused on protein kinase EphB2 that is the oncogenic driver of ependymoma, a rare type of brain and spinal cord cancer for which surgery or radiotherapy are the only available therapies due to inefficacy of standard chemotherapy in a large population of patients (*Nature* 2010, 466, 632-636). An aberrant activity of EphB2 has been observed in adhesion and cellular invasion in pediatric medulloblastoma (*Neuro-Oncology* 2012, 14(9): 1125-1135). EphB2, with other protein kinases like AXL, $FGFR_2$, IGF1R and RET is activated in osteosarcoma cell lines supporting metastatic development. EphB2 is thus an attractive therapeutic target for treatment of osteosarcoma (*Oncogenesis* 2012, 1 (11), e34). Moreover mutations in protein kinases EphA3 and EphB2 have been identified on a panel of 52 pancreatic exocrine neoplasms (*PLoS One* 2010, 5(9), e12653).

The receptor tyrosine kinase family includes the members TRKA, TRKB and TRKC and plays an important role during the development and maintenance of the central and peripheral nervous system. In particular, TRKA and TRKB are involved in neuroblastoma Inhibition of TRK kinase proteins activity might be a useful therapy for the treatment of other type of cancers where these targets are overexpressed like in prostate, lung, colon, pancreas and breast cancer. For example TRKB protein kinase promotes the metastatic process of lung adenocarcinoma and is an important target for the treatment of metastatic lung cancer (*Proc. Natl. Acad. Sci. USA* 2014, 111 (28), 10299-10304).

Mutations in the NTRK1 gene, which encodes the TRKA kinase, for example are often present in cancers such as thyroid papillary carcinoma. Mutations occur through rearrangements of genetic material that combine the NTRK1 gene with another gene. These rearrangements give rise to mutant proteins known as oncoproteins that, unlike normal TRKA protein, do not require activation by binding to the protein NGFβ. The constant activation of the protein triggers signaling for cells growth and proliferation leading to thyroid papillary carcinoma. NTRK1 rearrangements were identified in human cell lines of colorectal cancer and observed even in patients with lung cancer. They lead to constitutive activation of the kinase activity and are oncogenic. In vitro treatment of cells expressing forms of rearranged NTRK1 with inhibitors of the TRKA kinase activity inhibits autophosphorylation of TRKA and cell growth (*Nat. Med.* 2013, 19 (11), 1469-1472). Finally, TRKA TRKB and TRKC protein kinases may be important biological mediators in pain-related disorders such as rheumatoid arthritis, Crohn's disease, neuropathic pain of traumatic origin, depression, fibromyalgia and irritable bowel syndrome.

RIPK2 kinase (Receptor interacting protein kinase-2), also known as RIP2 or RICK CARDIAK, is a serine-threonine protein kinase having also a tyrosine kinase activity (*Genes & Dev.* 2010, 24:2666-2677). Its C-terminal domain interacts with the cytoplasmic receptors NOD1 and NOD2 that play an important role in innate immune response. After activation, RIPK2 is associated with NOD1 and NOD2 and acts as a molecular scaffold to aggregate other kinases such as IKKα/β and TAK1/γ, involved in the activation of NF-κB and MAP kinases. The lack of regulation of its signal was related to auto-inflammatory diseases, in particular the development of Crohn's disease. In vivo pharmacological inhibition of RIPK2 leads to a marked improvement of the disease in a spontaneous model of ileitis due to Crohn's disease (*J. Biol. Chem.* 2014, 289, 29651-29664).

RIPK2 protein kinase is implicated in the migration and invasion of tumor cells. Recent findings show that the expression of the RIPK2 gene is significantly increased in triple-negative breast tumors (negative for estrogen receptors, progesterone and Her2/Neu-Her2) compared to other clinical subtypes and high RIPK2 gene expression correlates with a decrease in progression-free survival of the disease. These studies show that the RIPK2 gene is an independent prognostic marker that stimulates the processes of metastasis in patients with advanced breast cancer.

Finally the inhibition of the RIPK2 kinase increases the chemo sensitivity of cancer cells to docetaxel and decreases both the tumor and lung metastases in experimental models of mammary tumor (*Breast Cancer Res.* 2014, 16: $R_{28}$). RIPK2 inhibitors containing the indazole nucleus structure are described in WO2011120025.

The non-receptor tyrosine kinase FYN is a protein that belongs to the SRC kinases family (SFKs) and is involved in normal physiological conditions in signal transduction pathways in the nervous system as well as in the development and activation of T lymphocytes. In cancer, FYN contributes to development and progression of melanoma, glioblastoma, squamous cell carcinoma and breast carcinoma. Recently FYN has been reported to play a key role in Tamoxifen-resistant ER positive breast cancer cell lines (*Pharmacol. Res.* 2015, 100, 250-254). Activating mutations of FYN have been also observed in integrated molecular analysis of adult T cell leukemia/lymphoma (ATL) (*Nat. Genet.* 2015, 47 (11), 1304-1315).

Alzheimer's disease is a neurodegenerative disease with a high incidence in the population over 85 years. The disease is characterized by the presence of plaques of beta-amyloid peptide (Aβ) and neurofibrillary tangles. There are numerous evidences involving the non-receptor tyrosine kinase Fyn in the pathogenesis of Alzheimer's disease. Fyn is involved in synaptic plasticity and plays a role in the regulation of Aβ production mediating synaptic deficits and Aβ-induced neurotoxicity. Fyn tyrosine phosphorylation induces tau protein activation that has been observed in neurofibrillary tangles in AD brain. Recent studies demonstrate that Aβ activates Fyn by binding to cellular prion protein on cell surface of Aβ oligomers. The interaction of Fyn with both Aβ and tau protein makes Fyn an important potential therapeutic target for the treatment of Alzheimer's disease (*J. Alzheimer's Dis.* 2011, 27(2), 243-252; *Alzheimer's Research* & Therapy, 2014, 6:8). Finally FYN regulates microglial neuroinflammatory responses in cell culture and animal models of Parkinson's disease making FYN a relevant and potential translational target for intervention of progressive neurodegenerative diseases (*J. Neurosc.* 2015, 35(27): 10058-10077).

The protein MAP4K2 or GCK kinase is a mitogen-activated protein kinase (MAPK) reported to be involved in pathogen associated molecular pattern signaling and systemic inflammation through JNK and p38 pathways. Moreover, in cancer disease MAP4K2 has been described to be a player upstream in the NFkβ pathway regulating the response of colorectal cancer to RAF inhibition. Recently GCK protein kinase has been also described as relevant target of mutant NRAS signaling especially in acute leukemia cell line with NRAS mutations (*Blood* 2015, 125 (20), 3133-3143).

The interleukin-1 receptor-associated kinases (IRAKs) are key mediators of toll-like receptor (TLR) and interleukin-1 receptor (IL1R) signaling processes. TLR/IL1R-mediated signaling controls diverse cellular processes including inflammation, apoptosis and cellular differentiation. IRAKs are categorized as serine/threonine protein kinases but only IRAK1 and IRAK4 display kinase activity. Human epidemiological studies as well as transgenic mouse models have linked genetic variations in IRAK genes to a collection of diverse diseases including inflammation and cancer. In particular, IRAK4 has been reported to be involved in melanoma, lymphoma, leukemia and breast cancer (*Br. J. Cancer* 2015, 112, 232-237).

The protein kinase JAK2 is a non-receptor tyrosine kinase that belongs to the Janus family of kinases (JAKs) in addition to JAK1 and JAK3 members. JAK2 is involved in several myeloproliferative diseases like essential thrombocythemia or primary myeolofibrosys. Mutational studies revealed that the somatic mutation V617F, within the pseudokinase domain of JAK2, is associated to disease development making the JAK2 protein kinase constitutively active. The prevalence of JAK2 activation in certain patients with myeloproliferative disorders provided a strong rationale for the exploration of new therapeutics to treat such diseases culminating with the discovery of Ruxolitinib, the first JAK1-JAK2 dual inhibitor approved by FDA. However myeloproliferative cells may develop an adaptive form of resistance to JAK2 inhibitors, termed persistence, causing the lack of pathologic remission despite clinical benefits for patients. Thus novel approaches providing inhibitors that could inactivate the JAK2 kinase activity more efficiently are urgently needed (*Blood* 2013, 122 (13), 2167-2175).

DESCRIPTION OF THE INVENTION

Indazole-based protein kinase inhibitors for the treatment of neurodegenerative diseases, inflammatory diseases, autoimmune diseases, obesity, pain and cancer have been disclosed in the following patent applications: WO2003/097610, WO2003/078403, WO2003/051847, WO2004/022544, WO2004/113303, WO2005/009389, WO2005/073219, WO2006/086255, WO2006/003276, WO2008/003396, WO2009/013126, WO2010/064875, WO2011/115725, WO2012/101239, WO2012/084704, WO2013/024011, WO2014/056083, WO2014/016433, WO2014/016434, WO2015/073344, WO2015/104662 and WO2015/112445.

In spite of undeniable advance in the field, there is still an urgent medical need for more effective and safer treatments for a large percentage of patients with such diseases. In this context the unquestionable need of novel inhibitors able to overcome the insurgence of drug resistance is emerging. The present invention relates to novel pharmaceutical products able to inhibit or modulate the activity of wild type and mutated forms of certain protein kinases. For example, the present invention relates to pharmaceutical products able to modulate the kinase activity of wild type ALK protein or ALK mutations responsible for resistance against drugs like Crizotinib or other approved ALK inhibitors such as Ceritinib or Alectinib. Relevant resistance causing mutations observed in ALK positive treated patients and modulated by compounds of the present invention are for example L1196M, C1156Y, L1152R, G1269A, F1174V, S1206Y and F1174L. The present invention also relates to certain compounds able to modulate the kinase activity of wild type, rearranged or mutated forms of one or more members of protein kinases such as the tropomyosin receptors (TRKs), the RET proto-oncogene receptor, the ephrin receptors, the ROS proto-oncogene 1 receptor, the discoidin domain receptors, the associated interleukin-1 receptors, the non-receptors Janus kinases and the proto-oncogene SRC tyrosine kinase family members.

In one embodiment the invention provides compounds of general Formula (I)

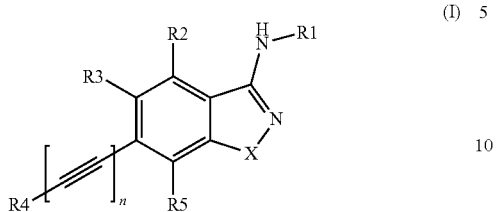

wherein:
X is —NH— or —O—, preferably —NH—;
$R_1$ is hydrogen or —CO—$R_6$, preferably —CO—$R_6$;
$R_2$ and $R_5$ are independently selected in the group of hydrogen, halogen and $C_1$-$C_6$ alkyl, preferably hydrogen;
$R_3$ is hydrogen or —Y—Ar where Y is a divalent group selected from —CH$_2$—, —NH—, —O—, —S—, —S(O)—, and —S(O)$_2$—, preferably —CH$_2$—;
Ar is an aryl, preferably phenyl or naphthyl, even more preferably phenyl, or a 5-10 membered heteroaryl, where the aryl or heteroaryl is optionally substituted by one to three groups independently selected from halogen, $C_1$-$C_6$ alkyl, $C_1$-$C_6$ haloalkyl, $C_1$-$C_6$ hydroxyalkyl, $C_1$-$C_6$ haloalkoxy, $C_1$-$C_6$ halothioalkoxy, cyano, hydroxy, mercapto, amino, $C_1$-$C_6$ alkoxy, $C_1$-$C_6$ thioalkoxy, $C_1$-$C_6$ mono alkylamino, $C_1$-$C_6$ bis alkylamino, carbamoyl, N—($C_1$-$C_6$ alkyl) carbamoyl, N,N-bis ($C_1$-$C_6$ alkyl) carbamoyl, $C_1$-$C_6$ acylamino, N—($C_1$-$C_6$ alkyl)-N—($C_1$-$C_6$ acyl)amino, N—($C_1$-$C_6$ alkyl) sulfonylamino, and N,N-bis ($C_1$-$C_6$ alkyl)sulfonylamino; preferably Ar is a phenyl substituted by one or two groups selected independently from halogen, $C_1$-$C_6$ alkyl, $C_1$-$C_6$ haloalkyl, carbamoyl, N—($C_1$-$C_6$) alkylcarbamoyl, and N,N-bis ($C_1$-$C_6$ alkyl)carbamoyl, in particular halogen such as fluorine or chlorine, $C_1$-$C_6$ haloalkyl such as trifluoromethyl, $C_1$-$C_6$ alkyl such as methyl, and carbamoyl. Even more preferably Ar is selected from 3,5-difluorophenyl, 3-fluorophenyl, 3-chlorophenyl, 3-bromophenyl, 2,4-difluorophenyl, 2,5-difluorophenyl, 2,6-difluorophenyl, 3,5-dimethylphenyl, 3,5-dichlorophenyl, 2,6-dichlorophenyl, 2,5-dichlorophenyl, 5-cyano-3-fluorophenyl, 3-cyano-6-fluorophenyl, and 2-cyano-5-fluorophenyl;
$R_4$ is selected from:
aryl, preferably phenyl or naphthyl, even more preferably phenyl, optionally substituted by one to three substituents independently selected from hydroxyl, amino, —OC(O)NHR$_e$, —OR$_e$, —NHC(O)NHR$_e$, halogen, cyano, $C_1$-$C_6$ alkyl, $C_1$-$C_6$ hydroxyalkyl, $C_1$-$C_6$ haloalkyl, $C_1$-$C_6$ haloalkoxy, $C_1$-$C_3$ alkoxy, carbamoyl, —OCH$_2$CH$_2$R$_e$, —OCH$_2$C(O)NHR$_e$, —OCH$_2$CH$_2$OR$_e$, —OCH$_2$CH$_2$NHR$_e$, —CH$_2$C(O) NHR$_e$, N—($C_1$-$C_6$ alkyl)carbamoyl, N—($C_3$-$C_6$ cycloalkyl)carbamoyl, $C_1$-$C_6$ acylamino, $C_1$-$C_6$ alkylsulfonylamino, N—($C_1$-$C_6$ alkyl)aminosulfonyl, $C_1$-$C_6$ alkylsulfonyl and aminosulfonyl, being R$_e$ an aryl, preferably phenyl or naphthyl, even more preferably a phenyl, optionally substituted by one or two substituents independently selected from $C_1$-$C_6$ haloalkyl, preferably trifluoromethyl, and CH$_2$-A, where A is an heterocyclyl selected among pyrrolidinyl, piperidinyl, piperazinyl, and morpholinyl and said heterocyclyl being optionally substituted by a $C_1$-$C_3$-alkyl group; preferably $R_4$ is a phenyl substituted by one or two groups selected from $C_1$-$C_6$ alkyl, $C_1$-$C_6$ haloalkyl, halogen and hydroxyl, preferably even more hydroxyl;
5-10 membered heteroaryl, preferably pyridyl, pyrimidinyl, pyridazinyl, pyrazinyl, triazinyl, benzo-pyrazolyl, indolyl, isoindolyl, pyrazolyl, indazolyl, imidazopyridinyl, pyrrolo-pyridinyl, thiazolyl, benzo-imidazolyl, benzo-oxazolyl, benzo-isoxazolyl, optionally substituted on the carbon atoms with one or two groups independently selected from amino, hydroxyl, $C_1$-$C_6$ acylamino, oxo, halogen, cyano, $C_1$-$C_6$ alkylsulfonyl, $C_1$-$C_6$ alkylsulfonylamino, N—($C_1$-$C_6$ alkyl)aminosulfonyl, aminosulfonyl, $C_1$-$C_6$ alkyl, $C_1$-$C_6$ haloalkyl, $C_1$-$C_3$ alkoxy, $C_1$-$C_6$ hydroxyalkyl, carbamoyl, N—($C_1$-$C_6$ alkyl)carbamoyl and N—($C_3$-$C_6$ cycloalkyl)carbamoyl;
(R$_a$)(R$_b$)(Z)C— where R$_a$ and R$_b$ are independently selected from hydrogen and $C_1$-$C_3$ alkyl and Z is selected from hydroxyl, —OC(O)NHR$_e$, —OR$_e$, amino, and —NHC(O)NHR$_e$, being R$_e$ as defined above; preferably R$_a$ and R$_b$ are hydrogen or methyl and Z is hydroxyl;
$R_6$ is aryl, preferably phenyl or naphthyl, even more preferably phenyl, in which the aryl is substituted by $R_7$ and $R_8$;
$R_7$ is selected from the group consisting of hydrogen, —OR$_f$ and —NR$_f$R$_g$, where R$_f$ and R$_g$ are independently selected from hydrogen, $C_1$-$C_6$ alkyl, $C_2$-$C_6$ alkyl optionally substituted by amino, $C_1$-$C_3$ mono alkylamino, $C_1$-$C_3$ bis alkylamino, hydroxy and $C_1$-$C_3$ alkoxy, $C_3$-$C_7$ cycloalkyl and heterocyclyl groups from 4 to 7 atoms containing up to 2 heteroatoms selected from oxygen, sulfur and nitrogen, in which those $C_3$-$C_7$ cycloalkyl and heterocyclyl are optionally substituted by one or two substituents independently selected from halogen, $C_1$-$C_6$ alkyl, $C_1$-$C_6$ haloalkyl, $C_1$-$C_6$ haloalkoxy, halothioalkoxy, nitro, cyano, hydroxy, $C_1$-$C_6$ alkoxy, mercapto, amino, $C_1$-$C_6$ alkylthio, $C_1$-$C_6$ mono alkylamino, $C_1$-$C_6$ bis alkylamino, $C_1$-$C_6$ acylamino, N—($C_1$-$C_6$ alkyl)-N—($C_1$-$C_6$ acyl)amino, $C_1$-$C_6$ alkyl sulfonylamino, N—($C_1$-$C_6$ alkyl)-N—($C_1$-$C_6$ alkyl)sulfonylamino, N—($C_1$-$C_6$ alkyl)carbamoyl, N—($C_3$-$C_7$ cycloalkyl)carbamoyl, and heterocyclyl groups from 4 to 7 atoms containing up to 2 heteroatoms selected from oxygen, sulfur and nitrogen; preferably $R_7$ is selected from hydrogen, —NR$_f$R$_g$ where R$_f$ is hydrogen and R$_g$ is $C_3$-$C_7$ cycloalkyl and heterocyclyl; even more preferably $R_7$ is a group —NHR$_g$ where R$_g$ is selected from tetrahydropiranyl and piperidinyl, or $R_7$ is one of the following groups:

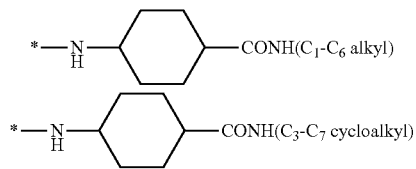

in cis o trans configuration and where the asterisk indicates the bond of those groups with $R_6$;
$R_8$ is selected from the group consisting of hydrogen, —OR$_c$, —NR$_c$R$_d$, 5-10 membered heteroaryl and heterocyclyl groups from 4 to 7 atoms containing up to 2 heteroatoms selected from oxygen, sulfur and nitrogen and optionally substituted by a substituent selected from halogen, $C_1$-$C_6$ alkyl, $C_1$-$C_6$ haloalkyl, $C_1$-$C_6$ haloalkoxy, $C_1$-$C_6$ halothioalkoxy, nitro, cyano, hydroxy, $C_1$-$C_6$ alkoxy, mercapto, $C_1$-$C_6$ alkylthio, amino, $C_1$-$C_6$ mono alkylamino, $C_1$-$C_6$ bis alkylamino, $C_1$-$C_6$ acylamino, N—($C_1$-$C_6$ alkyl)-N—($C_1$-$C_6$ acyl)amino, $C_1$-$C_6$ alkylsulfonylamino, N—($C_1$-$C_6$ alkyl)-N—($C_1$-$C_6$ alkyl)sulfonylamino, (N,N-bis($C_1$-$C_6$ alkyl)carbamoyl)$C_1$-$C_6$ alkyl and heterocyclyl groups from 4 to 7 atoms containing up to two heteroatoms selected from oxygen, sulfur and nitrogen;

$R_c$ and $R_d$ are independently selected from hydrogen, $C_1$-$C_6$ alkyl, $C_2$-$C_6$ alkyl optionally substituted by amino, $C_1$-$C_3$ mono alkylamino, $C_1$-$C_3$ bis alkylamino, hydroxyl, and $C_1$-$C_3$ alkoxy; or $R_c$ and $R_d$ are a $C_1$-$C_6$ cycloalkyl; preferably $R_8$ is a heterocyclyl selected among pyrrolidinyl, piperidinyl, piperazinyl, and morpholinyl, optionally substituted by a group selected from $C_1$-$C_3$-alkyl; even more preferably $R_8$ is a piperazinyl or a 4-methylpiperazinyl;

n is 0 or 1;

with the provisos that when n=0, then $R_3$ is —Y—Ar and $R_4$ is different from $(R_a)(R_b)(Z)C$—;

when n=1 and $R_3$ is H, then $R_4$ is aryl, heteroaryl or $(R_a)(R_b)(Z)C$— where Z is selected from —$OR_e$, —$OC(O)NHR_e$ and —$NHC(O)NHR_e$;

their N-oxides, pharmaceutically acceptable salts, enantiomers, stereoisomers, atropisomers, rotamers, tautomers, diastereomers, or racemates.

DETAILED DESCRIPTION OF THE INVENTION

The terms "$C_1$-$C_3$ alkyl" and "$C_1$-$C_6$ alkyl" mean a radical of a saturated aliphatic hydrocarbon, with a linear or branched chain having, respectively, from 1 to 3 and 1 to 6 carbon atoms. Examples of these terms are methyl, ethyl, propyl, isopropyl, n-butyl, iso-butyl, tert-butyl, n-amyl, iso-amyl and n-hexyl.

The term "$C_3$-$C_7$ cycloalkyl" means a monocyclic ring of 3 up to 7 carbon atoms, which may contain one or more double bonds but which has not a system of fully electrons conjugated 7E system. Examples of cycloalkyl groups are cyclopropane, cyclobutane, cyclopentane, cyclopentene, cyclohexene, cyclohexane, cyclohexadiene, and cycloheptane.

The terms "$C_1$-$C_3$ alkoxy" and "$C_1$-$C_6$ alkoxy" mean an alkyloxy group where the alkyl portion is as defined above. Examples of such groups are methoxy, ethoxy, n-propoxy, i-propoxy, n-butoxy, isobutoxy, sec-butoxy, tert-butoxy, pentoxy and hexoxy.

The term "$C_1$-$C_6$ thioalkoxy" means an alkyl-thio group in which the alkyl portion is as defined above. Examples of such groups are methylthio, propylthio, ethylthio, butylthio and hexylthio.

The terms "($C_1$-$C_6$) haloalkyl" and "($C_1$-$C_6$) haloalkoxy" refer to the above-mentioned groups "($C_1$-$C_6$) alkyl" and "($C_1$-$C_6$) alkoxy" where one or more hydrogen atoms are replaced by one or more halogen atoms, which can be the same or different. Examples of such groups "($C_1$-$C_6$) haloalkyl" and "($C_1$-$C_6$) haloalkoxy" can therefore include alkyl and alkoxy halogenated groups, poly- and per-halogenated, in which all hydrogen atoms are replaced by halogen atoms, such as trifluoromethyl and trifluoromethoxy.

The term "$C_1$-$C_6$ halothioalkoxy" refers to the above mentioned group "($C_1$-$C_6$) thioalkoxy" where one or more hydrogen atoms are replaced by one or more halogen atoms, which can be the same or different.

The term "carbamoyl" means the $CONH_2$ group.

The term "aryl" means a hydrocarbon consisting of a mono-, bi- and tricyclic annular system, where the rings are fused together or covalently bound together and at least one of the carbocyclic rings is aromatic. The term "aryl" means a cyclic aromatic compound as an aromatic hydrocarbon with 6 atoms, an aromatic hydrocarbon consisting of two rings with six atoms fused, and an aromatic hydrocarbon consisting of two rings with six atoms covalently linked. Examples of aryl groups include phenyl, alpha- or beta-naphthyl, 9,10-dihydroanthracenyl, indanyl, fluorenyl and biphenyl.

The term "heteroaryl" means a mono or bicyclic annular system comprising 5 up to 10 atoms containing from one to four heteroatoms selected from nitrogen, oxygen and sulfur, where rings are fused together or covalently bound together and at least one of the rings is aromatic. Examples of heteroaryl groups include pyrrolyl, furyl, thiophenyl, imidazolyl, pyrazolyl, oxazolyl, isoxazolyl, thiazolyl, isothiazolyl, indolyl, isoindolyl, indazolyl, imidazo-pyridinyl, pyrrolo-pyridinyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl, and triazinyl.

The words "heterocyclyl" or "heterocyclic ring", mean a carbocyclic ring from 4 up to 7 atoms, saturated or partially unsaturated, where one or more carbon atoms are independently replaced by nitrogen, oxygen or sulfur. The atoms of nitrogen and sulfur are eventually oxidized, and the atom (s) of nitrogen are eventually quaternary. Examples of heterocyclyl groups include, for example, radical derived from oxirane, aziridine, furan, oxetane, azetidine, tetrahydrofuran, tetrahydrothiophene, dihydrofuran, dihydrothiophene, pyrrolidine, dihydropyrrole, pyran, dihydropyran, tetrahydropyran, tetrahydrothiopyran, piperidine, pyrazoline, oxazoline, isoxazolidine, isoxazoline, thiazolidine, isothiazoline, thiazoline, dioxane, piperazine, morpholine, thiomorpholine, hexamethyleneimine and homopiperazine.

The term "aromatic" refers to a fragment in which the constituent atoms give rise to an unsaturated annular system, all atoms in the system are hybridized $sp^2$ and the total number of it electrons is $4n+2$, where n is an integer number.

In one embodiment the invention refers to compounds with general formula (I) as defined above where X is NH.

In another embodiment the invention refers to compounds with general formula (I) as defined above where:

X is —NH—;

$R_1$ is hydrogen or —CO—$R_6$;

$R_2$ and $R_5$ are independently selected in the group consisting of hydrogen, halogen and $C_1$-$C_6$ alkyl;

$R_3$ is hydrogen or —Y—Ar where Y is the bivalent group —$CH_2$—;

Ar is phenyl or naphthyl, optionally substituted by one or two groups selected independently among halogen, $C_1$-$C_6$ alkyl, $C_1$-$C_6$ haloalkyl, cyano, carbamoyl, N—($C_1$-$C_6$ alkyl) carbamoyl, and N,N-bis ($C_1$-$C_6$ alkyl)carbamoyl;

$R_4$ is selected from the following group:

phenyl or naphthyl optionally substituted by one or two substituents selected among hydroxyl, $C_1$-$C_3$ alkoxy, amine, —$OC(O)NHR_e$, —$OR_e$, —$NHC(O)NHR_e$, halogen, cyano, $C_1$-$C_6$ hydroxyalkyl, $C_1$-$C_6$ haloalkyl, carbamoyl, $C_1$-$C_6$ alkyl, $C_1$-$C_6$ haloalkoxy, —$OCH_2CH_2R_e$, —$OCH_2C(O)NHR_e$, —$OCH_2CH_2OR_e$, —$CH_2CH_2ORe$ —$OCH_2CH_2NHR_e$, —$CH_2C(O)NHR_e$, N—($C_1$-$C_6$ alkyl)carbamoyl, N—($C_3$-$C_6$ cycloalkyl)carbamoyl, $C_1$-$C_6$ acylamino, $C_1$-$C_6$ alkylsulfonylamino, aminosulfonyl, $C_1$-$C_6$ alkylsulfonyl, and N—($C_1$-$C_6$ alkyl) aminosulfonyl, being $R_e$ a phenyl, optionally substituted by one or two substituents selected among trifluoromethyl and CH$_2$-A where A is as defined above;

heteroaryl from 5 up to 10 atoms selected from pyridyl, pyrimidinyl, pyridazinyl, pyrazinyl, triazinyl, benzopyrazolyl, benzo-imidazolyl, indolyl, isoindolyl, pyrazolyl, indazolyl, imidazo-pyridinyl, pyrrolo-pyridinyl, thiazolyl, benzo-oxazolyl or benzo-isoxazolyl, optionally substituted on carbon atoms with one or two substituents independently selected from amino, oxo, C$_1$-C$_6$ acylamino, hydroxyl, C$_1$-C$_3$ alkoxy, halogen, C$_1$-C$_6$ alkylsulfonyl, C$_1$-C$_6$ alkylsulfonylamino, N—(C$_1$-C$_6$ alkyl)aminosulfonyl, aminosulfonyl, C$_1$-C$_6$ alkyl, cyano, C$_1$-C$_6$ haloalkyl, C$_1$-C$_6$ hydroxyalkyl, carbamoyl, N—(C$_1$-C$_6$ alkyl)carbamoyl and N—(C$_3$-C$_6$ cycloalkyl)carbamoyl;

(R$_a$)(R$_b$)(Z)C— where R$_a$ and R$_b$ are both hydrogen or methyl and Z is hydroxyl, —OC(O)NHR$_e$, —OR$_e$, amino, or —NHC(O)NHR$_e$;

R$_6$ is phenyl or naphthyl;

R$_7$ is selected among hydrogen, —NR$_f$R$_g$ where R$_f$ is hydrogen and R$_g$ is C$_3$-C$_7$ cycloalkyl, heterocyclyl or C$_2$-C$_6$ alkyl optionally substituted by C$_1$-C$_3$ alkoxy; or R$_7$ is a group selected among:

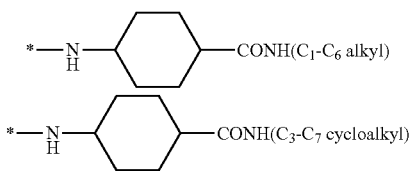

with cis or trans configuration and where the asterisk * indicates the bond of those groups with R$_6$;

R$_8$ is hydrogen or a heterocyclyl selected among pyrrolidinyl, piperidinyl, piperazinyl, and morpholinyl, optionally substituted by C$_1$-C$_3$-alkyl;

n is 0 or 1;

with the provisos that
when n=0, then R$_3$ is —Y—Ar and R$_4$ is different from (R$_a$)(R$_b$)(Z)C—;
when n=1 and R$_3$ is H, then R$_4$ is aryl, heteroaryl or (R$_a$)(R$_b$)(Z)C— where Z is —OR$_e$.

In another embodiment the invention refers to compounds with general formula (I) as defined above where:
X is —NH—;
n is 0;
R$_1$ is —CO—R$_6$;
R$_2$ and R$_5$ are selected from hydrogen, halogen and C$_1$-C$_3$ alkyl;
R$_3$ is —CH$_2$Ar, where Ar is phenyl substituted by one or two groups independently selected from halogen, C$_1$-C$_6$ alkyl, C$_1$-C$_6$ haloalkyl, cyano, carbamoyl, N—(C$_1$-C$_6$ alkyl)carbamoyl, and N,N-bis(C$_1$-C$_6$ alkyl)carbamoyl;
R$_4$ is phenyl optionally substituted by one or two substituents selected from hydroxyl, C$_1$-C$_3$ alkoxy, amino, —OC(O)NHR$_e$, —OR$_e$, —NHC(O)NHR$_e$, halogen, cyano, C$_1$-C$_6$ haloalkyl, C$_1$-C$_6$ alkyl, C$_1$-C$_6$ hydroxyalkyl, C$_1$-C$_6$ haloalkoxy, —OCH$_2$CH$_2$R$_e$, —OCH$_2$C(O)NHR$_e$, —CH$_2$CH$_2$OR$_e$, —OCH$_2$CH$_2$OR$_e$, —OCH$_2$CH$_2$NHR$_e$, —CH$_2$C(O)NHR$_e$, N—(C$_1$-C$_6$ alkyl)carbamoyl, N—(C$_3$-C$_6$ cycloalkyl)carbamoyl, C$_1$-C$_6$ acylamino, C$_1$-C$_6$ alkylsulfonylamino, and aminosulfonyl, being R$_e$ as defined above;
R$_6$ is phenyl substituted by R$_7$ and R$_8$.

In another embodiment the invention refers to compounds with general formula (I) as defined above where:
X is —NH—;
n is 0;
R$_1$ is —CO—R$_6$;
R$_2$ and R$_5$ are selected from hydrogen, halogen and C$_1$-C$_3$ alkyl;
R$_3$ is —CH$_2$Ar, where Ar is phenyl substituted by one or two groups independently selected from halogen, C$_1$-C$_6$ alkyl, C$_1$-C$_6$ haloalkyl, cyano, carbamoyl, N—(C$_1$-C$_6$ alkyl)carbamoyl, and N,N-bis(C$_1$-C$_6$ alkyl)carbamoyl;
R$_4$ is heteroaryl selected from pyridyl, pyrimidinyl, pyrazolyl, imidazo[4,5-b]pyridinyl, indazolyl, isoindolyl, and pyrrolo[2,3-b]pyridinyl, which are optionally substituted on the carbon atoms by one or two substituents independently selected from C$_1$-C$_6$ alkyl, C$_1$-C$_6$ haloalkyl, cyano, carbamoyl, C$_1$-C$_6$ hydroxyalkyl, C$_1$-C$_3$ alkoxy, amino, oxo and hydroxyl;
R$_6$ is phenyl substituted by R$_7$ and R$_8$.

In another embodiment the invention refers to compounds with general formula (I) as defined above where:
X is —NH—;
n is 0;
R$_1$ is —CO—R$_6$ where R$_6$ is phenyl substituted in position 2 and 4, respectively, by group R$_7$ and R$_8$;
R$_2$ and R$_5$ are hydrogen;
R$_3$ is —CH$_2$Ar, where Ar is phenyl substituted by one or two substituents independently selected from fluoro, chloro, trifluoromethyl, methyl, cyano and carbamoyl;
R$_4$ is phenyl preferably substituted by one or two substituents independently selected from trifluoromethyl, hydroxyl, halogen, C$_1$-C$_3$-alkoxy, C$_1$-C$_6$ hydroxyalkyl, amino, C$_1$-C$_6$ alkyl, N—C$_1$-C$_6$ alkyl)carbamoyl, —OC(O)NHR$_e$, —OR$_e$, —NHC(O)NHR$_e$, —OCH$_2$CH$_2$R$_e$, —OCH$_2$C(O)NHR$_e$, —OCH$_2$CH$_2$OR$_e$, —OCH$_2$CH$_2$NHR$_e$, and —CH$_2$C(O)NHR$_e$, being R$_e$ a trifluoromethylphenyl group.

In another embodiment the invention refers to compounds with general formula (I) where:
X is —NH—;
n is 0;
R$_1$ is —CO—R$_6$ where R$_6$ is phenyl substituted in position 2 and 4, respectively, by group R$_7$ and R$_8$;
R$_2$ and R$_5$ are hydrogen;
R$_3$ is —CH$_2$Ar, where Ar is selected among 3,5-difluorophenyl, 3-fluorophenyl, 3-cholophenyl, 3-bromophenyl, 2,4-difluorophenyl, 2,5-difluorophenyl, 2,6-difluorophenyl, 3,5-dimethylphenyl, 3,5 dichlorophenyl, 2,5-dichlorophenyl, 2,6-dichlorophenyl, 5-cyano-3-fluorophenyl, 3-cyano-6-fluorophenyl, and 2-cyano-5-fluorophenyl;
R$_4$ is phenyl substituted by one or two groups selected from trifluoromethyl, fluoro, hydroxyl, methyl, hydroxymethyl, 1-hydroxy-1-methylethyl, methoxy, and N-methylcarbamoyl;
R$_7$ is NHR$_g$ where R$_g$ is selected among tetrahydropyranyl, 2-methoxyethyl and piperidinyl; or R$_7$ is a group selected among:

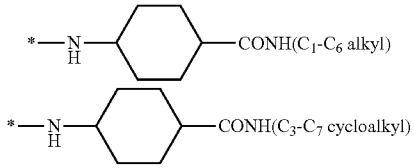

with cis or trans configuration and where the asterisk * indicates the bond of those groups with $R_6$;

$R_8$ is a piperazinyl or 4-methyl-piperazinyl.

In another embodiment the invention refers to compounds with general formula (I) where:

X is —NH—;
n is 0;
$R_1$ is —CO—$R_6$ where $R_6$ is phenyl substituted in position 2 by 4-tetrahydropyranylamino group or by 2-methoxyethylamino group and in position 4 by a 4-methyl-1-piperazinyl group;
$R_2$ and $R_5$ are hydrogen;
$R_3$ is —CH$_2$Ar, where Ar is a group 3,5-difluorophenyl, 3-fluorophenyl, 3-cholorophenyl, 3-bromophenyl, 2,4-difluorophenyl, 2,5-difluorophenyl, 2,6-difluorophenyl, 3,5-dimethylphenyl, 3,5-dichlorophenyl, 2,5-dichlorophenyl, 2,6-dichlorophenyl, 5-cyano-3-fluorophenyl, 3-cyano-6-fluorophenyl, and 2-cyano-5-fluorophenyl;
$R_4$ is phenyl substituted by hydroxyl groups, or with fluorine and hydroxyl groups, or with methyl and hydroxyl groups, or with trifluoromethyl and hydroxyl groups.

In another embodiment the invention refers to compounds with general formula (I) where:

X is —NH—;
n is 1;
$R_1$ is —CO—$R_6$ where $R_6$ is substituted phenyl in position 2 and 4, respectively, by a group $R_7$ and $R_8$;
$R_2$ and $R_5$ are hydrogen;
$R_3$ is hydrogen or —CH$_2$Ar, where Ar is phenyl substituted by one or two of substituents independently selected among fluoro, chloro, trifluoromethyl, cyano, methyl, and carbamoyl;
$R_4$ is phenyl substituted in position 3 or 4 by hydroxyl.

In another embodiment the invention refers to compounds with general formula (I) where:

X is —NH—;
n is 1;
$R_1$ is —CO—$R_6$ where $R_6$ is phenyl substituted in position 2 by 4-tetrahydropyranylamino group or by 2-methoxyethylamino group and in position 4 by a 4-methyl-1-piperazinyl or by a 1-piperazinyl group;
$R_2$ and $R_5$ are hydrogen;
$R_3$ is hydrogen or —CH$_2$Ar, where Ar is a group 3,5-difluorophenyl, 3-fluorophenyl, 3-chlorophenyl, 3-bromophenyl, 2,4-difluorophenyl, 2,5-difluorophenyl, 2,6-difluorophenyl, 3,5-dimethylphenyl, 3,5-dichlorophenyl, 2,5-dichlorophenyl, 2,6-dichlorophenyl, 5-cyano-3-fluorophenyl, 3-cyano-6-fluorophenyl and 2-cyano-5-fluorophenyl;
$R_4$ is phenyl substituted in position 3 or 4 by hydroxyl;

In another embodiment: the invention refers to compounds with general formula (I) where:

X is —NH—;
n is 1;
$R_1$ is hydrogen or —CO—$R_6$ where $R_6$ is phenyl substituted in position 2 by 4-tetrahydropyranylamino group or by 2-methoxyethylamino group and in position 4 by a 4-methyl-1-piperazinyl group;
$R_2$ and $R_5$ are hydrogen;
$R_3$ is hydrogen or 3,5-difluorobenzyl group;
$R_4$ is $(R_a)(R_b)(Z)C$— where $R_a$ and $R_b$ are independently selected between hydrogen and methyl and Z is selected among hydroxyl, —OC(O)NH($R_e$), —O$R_e$, amino, and —NHC(O)NH($R_e$), being $R_e$ a trifluoromethylphenyl group which is optionally substituted by a CH$_2$-A group, where A is an heterocyclyl selected among pyrrolidinyl, piperidinyl, piperazinyl, and morpholinyl;

with the proviso that when $R_3$ is hydrogen, then Z is selected from —O$R_e$, —OC(O)NH($R_e$) and —NHC(O)NH($R_e$), In another embodiment the invention refers to compounds with general formula (I) where:

X is —NH—;
n is 0;
$R_1$ is hydrogen;
$R_2$ and $R_5$ are selected among hydrogen, halogen and $C_1$-$C_3$ alkyl;
$R_3$ is —CH$_2$Ar, where Ar is a phenyl substituted by one or two substituents selected among fluoro, chloro, trifluoromethyl, methyl, cyano, and carbamoyl;
$R_4$ is a phenyl substituted by one or two substituents independently selected among $C_1$-$C_6$ alkyl, $C_1$-$C_6$ haloalkyl and hydroxyl;

In another embodiment the invention refers to compounds with general formula (I) where:

X is —NH—;
n is 0;
$R_1$ is hydrogen;
$R_2$ and $R_5$ are hydrogen; $R_3$ is —CH$_2$Ar, where Ar is a group 3,5-difluorophenyl, 3-fluorophenyl, 2,4-difluorophenyl, 2,5-difluorophenyl, 2,6-difluorophenyl, 3,5-dimethylphenyl, 3,5-dichlorophenyl, 2,5-dichlorophenyl, 2,6-dichlorophenyl, 5-cyano-3-fluorophenyl, 3-cyano-6-fluorophenyl, and 2-cyano-5-fluorophenyl;
$R_4$ is phenyl substituted by hydroxyl or by hydroxyl and methyl.

In another embodiment the invention refers to compounds with general formula (I) where X is —NH—;
n is 1;
$R_1$ is —CO—$R_6$ where $R_6$ is phenyl substituted in position 2 and position 4, respectively, by group $R_7$ and $R_8$, preferably in position 2 by 4-tetrahydropyranyl group and in position 4 by 4-methyl-1-piperazinyl group;
$R_2$ and $R_5$ are hydrogen;
$R_3$ is —CH$_2$Ar, where Ar is a group 3,5-difluorophenyl, 3-fluorophenyl, 2,4-difluorophenyl, 2,5-difluorophenyl, 2,6-difluorophenyl, 3,5-dimethylphenyl, 3,5-dichlorophenyl, 2,5-dichlorophenyl, 2,6-dichlorophenyl, 5-cyano-3-fluorophenyl, 3-cyano-6-fluorophenyl, and 2-cyano-5-fluorophenyl;
$R_4$ is $(R_a)(R_b)(Z)C$— where $R_a$ and $R_b$ are independently selected between hydrogen and methyl and Z is selected among hydroxyl and amino.

In another embodiment the invention refers to compounds with general formula (I) where:

X is —NH—;
n is 1;
$R_1$ is —CO—$R_6$ where $R_6$ is phenyl substituted in position 2 and position 4, respectively, by group $R_7$ and $R_8$, preferably in position 2 by 4-tetrahydropyranyl group and in position 4 by 4-methyl-1-piperazinyl group;
$R_2$ and $R_5$ are hydrogen;
$R_3$ is hydrogen;
$R_4$ is $(R_a)(R_b)(Z)C$— where $R_a$ and $R_b$ are independently selected between hydrogen and methyl and Z is selected among —OC(O)NH($R_e$), —O$R_e$, and —NHC(O)NH($R_e$), being $R_e$ a trifluoromethylphenyl group that is optionally substituted by a CH$_2$-A group, where A is an heterocyclyl selected among pyrrolidinyl, piperidinyl, piperazinyl, and morpholinyl.

Specific examples of compounds of the invention are:

| No. | Chemical Name |
|---|---|
| 1 | N-[6-[2-(3-hydroxyphenyl)ethynyl]-1H-indazol-3-yl]-4-(4-methylpiperazin-1-yl)-2-(tetrahydropyran-4-ylamino)benzamide; |
| 2 | 6-[3-[4-[(4-methylpiperazin-1-yl)methyl]-3-(trifluoromethyl)phenoxy]prop-1-ynyl]-1H-indazol-3-amine; |
| 3 | N-[5-(3,5-difluorophenyl)methyl]-6-(4-hydroxyphenyl)-1H-indazol-3-yl]-4-(4-methylpiperazin-1-yl)-2-(tetrahydropyran-4-ylamino)benzamide; |
| 4 | N-[5-[(3,5-difluorophenyl)methyl]-6-(3-hydroxyphenyl)-1H-indazol-3-yl]-4-(4-methylpiperazin-1-yl)-2-(tetrahydropyran-4-ylamino)benzamide; |
| 5 | N-[5-[(3,5-difluorophenyl)methyl]-6-(4-hydroxy-2-methyl-phenyl)-1H-indazol-3-yl]-4-(4-methylpiperazin-1-yl)-2-(tetrahydropyran-4-ylamino)benzamide; |
| 6 | N-[5-[(3,5-difluorophenyl)methyl]-6-(2-fluoro-4-hydroxy-phenyl)-1H-indazol-3-yl]-4-(4-methylpiperazin-1-yl)-2-(tetrahydropyran-4-ylamino)benzamide; |
| 7 | N-[5-[(3,5-difluorophenyl)methyl]-6-(5-hydroxy-2-methyl-phenyl)-1H-indazol-3-yl]-4-(4-methylpiperazin-1-yl)-2-(tetrahydropyran-4-ylamino)benzamide; |
| 8 | N-[5-[(3,5-difluorophenyl)methyl]-6-(2-fluoro-5-hydroxy-phenyl)-1H-indazol-3-yl]-4-(4-methylpiperazin-1-yl)-2-(tetrahydropyran-4-ylamino)benzamide; |
| 9 | N-[5-[(3,5-difluorophenyl)methyl]-6-[4-hydroxy-2-(trifluoromethyl)phenyl]-1H-indazol-3-yl]-4-(4-methylpiperazin-1-yl)-2-(tetrahydropyran-4-ylamino)benzamide; |
| 10 | N-[6-(2-aminopyrimidin-5-yl)-5-[(3,5-difluorophenyl)methyl]-1H-indazol-3-yl]-4-(4-methylpiperazin-1-yl)-2-(tetrahydropyran-4-ylamino)benzamide; |
| 11 | N-[6-(6-amino-3-pyridyl)-5-[(3,5-difluorophenyl)methyl]-1H-indazol-3-yl]-4-(4-methylpiperazin-1-yl)-2-(tetrahydropyran-4-ylamino)benzamide; |
| 12 | N-[6-(5-amino-3-pyridyl)-5-[(3,5-difluorophenyl)methyl]-1H-indazol-3-yl]-4-(4-methylpiperazin-1-yl)-2-(tetrahydropyran-4-ylamino)benzamide; |
| 13 | N-[5-[(3,5-difluorophenyl)methyl]-6-[3-(hydroxymethyl)phenyl]-1H-indazol-3-yl]-4-(4-methylpiperazin-1-yl)-2-(tetrahydropyran-4-ylamino)benzamide; |
| 14 | N-[6-(6-amino-4-methyl-3-pyridyl)-5-[(3,5-difluorophenyl)methyl]-1H-indazol-3-yl]-4-(4-methylpiperazin-1-yl)-2-(tetrahydropyran-4-ylamino)benzamide; |
| 15 | N-[5-[(3,5-difluorophenyl)methyl]-6-[1-(2-hydroxy-1,1-dimethyl-ethyl)pyrazol-4-yl]-1H-indazol-3-yl]-4-(4-methylpiperazin-1-yl)-2-(tetrahydropyran-4-ylamino)benzamide; |
| 16 | N-[5-[(3,5-difluorophenyl)methyl]-6-(2-oxo-1H-pyridin-4-yl)-1H-indazol-3-yl]-4-(4-methylpiperazin-1-yl)-2-(tetrahydropyran-4-ylamino)benzamide; |
| 17 | N-[5-[(3,5-difluorophenyl)methyl]-6-(3H-imidazo[4,5-b]pyridin-6-yl)-1H-indazol-3-yl]-4-(4-methylpiperazin-1-yl)-2-(tetrahydropyran-4-ylamino)benzamide; |
| 18 | N-[5-[(3,5-difluorophenyl)methyl]-6-(1H-pyrazol-4-yl)-1H-indazol-3-yl]-4-(4-methylpiperazin-1-yl)-2-(tetrahydropyran-4-ylamino)benzamide; |
| 19 | N-[5-[(3,5-difluorophenyl)methyl]-6-(3-fluoro-5-hydroxy-phenyl)-1H-indazol-3-yl]-4-(4-methylpiperazin-1-yl)-2-(tetrahydropyran-4-ylamino)benzamide; |
| 20 | N-[5-[(3,5-difluorophenyl)methyl]-6-[4-(methylcarbamoyl)phenyl]-1H-indazol-3-yl]-4-(4-methylpiperazin-1-yl)-2-(tetrahydropyran-4-ylamino)benzamide; |
| 21 | N-[5-[(3,5-difluorophenyl)methyl]-6-[4-hydroxy-3-methyl-phenyl]-1H-indazol-3-yl]-4-(4-methylpiperazin-1-yl)-2-(tetrahydropyran-4-ylamino)benzamide; |
| 22 | N-[5-[(3,5-difluorophenyl)methyl]-6-(6-hydroxy-3-pyridyl)-1H-indazol-3-yl]-4-(4-methylpiperazin-1-yl)-2-(tetrahydropyran-4-ylamino)benzamide; |
| 23 | N-[5-[(3,5-difluorophenyl)methyl]-6-phenyl-1H-indazol-3-yl]-4-(4-methylpiperazin-1-yl)-2-(tetrahydropyran-4-ylamino)benzamide; |
| 24 | N-[5-[(3,5-difluorophenyl)methyl]-6-(3-methoxyphenyl)-1H-indazol-3-yl]-4-(4-methylpiperazin-1-yl)-2-(tetrahydropyran-4-ylamino)benzamide; |
| 25 | N-[5-[(3,5-difluorophenyl)methyl]-6-(3-fluoro-4-hydroxy-phenyl)-1H-indazol-3-yl]-4-(4-methylpiperazin-1-yl)-2-(tetrahydropyran-4-ylamino)benzamide; |
| 26 | N-[5-[(3,5-difluorophenyl)methyl]-6-(1H-indazol-5-yl)-1H-indazol-3-yl]-4-(4-methylpiperazin-1-yl)-2-(tetrahydropyran-4-ylamino)benzamide; |
| 27 | N-[5-[(3,5-difluorophenyl)methyl]-6-pyrimidin-5-yl-1H-indazol-3-yl]-4-(4-methylpiperazin-1-yl)-2-(tetrahydropyran-4-ylamino)benzamide; |
| 28 | N-[5-[(3,5-difluorophenyl)methyl]-6-(3-oxoisoindolin-5-yl)-1H-indazol-3-yl]-4-(4-methylpiperazin-1-yl)-2-(tetrahydropyran-4-ylamino)benzamide; |
| 29 | N-[5-[(3,5-difluorophenyl)methyl]-6-(1H-pyrrolo[2,3-b]pyridin-5-yl)-1H-indazol-3-yl]-4-(4-methylpiperazin-1-yl)-2-(tetrahydropyran-4-ylamino)benzamide; |
| 30 | N-[5-[(3,5-difluorophenyl)methyl]-6-(4-pyridyl)-1H-indazol-3-yl]-4-(4-methylpiperazin-1-yl)-2-(tetrahydropyran-4-ylamino)benzamide; |
| 31 | N-[5-[(3,5-difluorophenyl)methyl]-6-(3-pyridyl)-1H-indazol-3-yl]-4-(4-methylpiperazin-1-yl)-2-(tetrahydropyran-4-ylamino)benzamide; |
| 32 | N-[5-[(3,5-difluorophenyl)methyl]-6-[4-(1-hydroxy-1-methyl-ethyl)phenyl]-1H-indazol-3-yl]-4-(4-methylpiperazin-1-yl)-2-(tetrahydropyran-4-ylamino)benzamide; |
| 33 | N-[5-[(3,5-difluorophenyl)methyl]-6-(4-hydroxyphenyl)-1H-indazol-3-yl]-4-(4-methylpiperazin-1-yl)-benzamide; |
| 34 | N-[5-[(3,5-difluorophenyl)methyl]-6-(4-hydroxy-2-methyl-phenyl)-1H-indazol-3-yl]-4-(4-methylpiperazin-1-yl)benzamide; |
| 35 | N-[5-[(3,5-difluorophenyl)methyl]-6-(1H-indazol-5-yl)-1H-indazol-3-yl]-4-(4-methylpiperazin-1-yl)benzamide; |
| 36 | N-[6-(2-aminopyrimidin-5-yl)-5-[(3,5-difluorophenyl)methyl]-1H-indazol-3-yl]-4-(4-methylpiperazin-1-yl)benzamide; |
| 37 | N-[5-[(3,5-difluorophenyl)methyl]-6-(4-hydroxy-3-methyl-phenyl)-1H-indazol-3-yl]-4-(4-methylpiperazin-1-yl)benzamide; |

-continued

| No. | Chemical Name |
|---|---|
| 38 | N-[5-(3-fluorophenyl)methyl]-6-(4-hydroxyphenyl)-1H-indazol-3-yl]-4-(4-methylpiperazin-1-yl)-2-(tetrahydropyran-4-ylamino)benzamide; |
| 39 | N-[6-(3-fluoro-4-hydroxy-phenyl)-5-[(3-fluorophenyl)methyl]-1H-indazol-3-yl]-4-(4-methylpiperazin-1-yl)-2-(tetrahydropyran-4-ylamino)benzamide; |
| 40 | N-[6-(2-fluoro-4-hydroxy-phenyl)-5-[(3-fluorophenyl)methyl]-1H-indazol-3-yl]-4-(4-methylpiperazin-1-yl)-2-(tetrahydropyran-4-ylamino)benzamide; |
| 41 | N-[6-(2-aminopyrimidin-5-yl)-5-[(3-fluorophenyl)methyl]-1H-indazol-3-yl]-4-(4-methylpiperazin-1-yl)benzamide; |
| 42 | N-[6-(3-fluoro-4-hydroxy-phenyl)-5-[(3-fluorophenyl)methyl]-1H-indazol-3-yl]-2-(2-methoxyethylamino)-4-(4-methylpiperazin-1-yl)benzamide; |
| 43 | 3-[3-amino-5-[(3,5-difluorophenyl)methyl]-1H-indazol-6-yl]-4-methyl-phenol; |
| 44 | 4-[3-amino-5-[(3,5-difluorophenyl)methyl]-1H-indazol-6-yl]phenol |

Further examples of compounds of the invention are:

| No. | Chemical Name |
|---|---|
| 45 | N-[5-[(3,5-difluorophenyl)methyl]-6-(4-hydroxyphenyl)-1H-indazol-3-yl]-4-piperazin-1-yl-2-(tetrahydropyran-4-ylamino)benzamide; |
| 46 | N-[5-[(3,5-difluorophenyl)methyl]-6-(3-hydroxyphenyl)-1H-indazol-3-yl]-4-piperazin-1-yl-2-(tetrahydropyran-4-ylamino)benzamide; |
| 47 | N-[5-[(3,5-difluorophenyl)methyl]-6-(5-hydroxy-2-methyl-phenyl)-1H-indazol-3-yl]-4-piperazin-1-yl-2-(tetrahydropyran-4-ylamino)benzamide; |
| 48 | N-[5-[(3,5-difluorophenyl)methyl]-6-(4-hydroxy-2-methyl-phenyl)-1H-indazol-3-yl]-4-piperazin-1-yl-2-(tetrahydropyran-4-ylamino)benzamide; |
| 49 | N-[5-(3-fluorophenyl)methyl]-6-(4-hydroxyphenyl)-1H-indazol-3-yl]-4-piperazin-1-yl-2-(tetrahydropyran-4-ylamino)benzamide; |
| 50 | N-[5-[(3,5-difluorophenyl)methyl]-6-(4-hydroxyphenyl)-1H-indazol-3-yl]-4-piperazin-1-yl-benzamide; |
| 51 | N-[5-[(3,5-difluorophenyl)methyl]-6-(2-oxo-1H-pyridin-4-yl)-1H-indazol-3-yl]-4-piperazin-1-yl-2-(tetrahydropyran-4-ylamino)benzamide; |
| 52 | N-[5-[(3,5-difluorophenyl)methyl]-6-[1-(2-hydroxy-1,1-dimethyl-ethyl)pyrazol-4-yl]-1H-indazol-3-yl]-4-piperazin-1-yl-2-(tetrahydropyran-4-ylamino)benzamide; |
| 53 | N-[5-[(3,5-difluorophenyl)methyl]-6-(1H-pyrazol-4-yl)-1H-indazol-3-yl]-4-piperazin-1-yl-2-(tetrahydropyran-4-ylamino)benzamide; |
| 54 | N-[5-[(3,5-difluorophenyl)methyl]-6-(2-fluoro-4-hydroxy-phenyl)-1H-indazol-3-yl]-4-piperazin-1-yl-2-(tetrahydropyran-4-ylamino)benzamide; |
| 55 | N-[5-[(3,5-difluorophenyl)methyl]-6-(4-hydroxy-2-methyl-phenyl)-1H-indazol-3-yl]-4-piperazin-1-yl-benzamide; |
| 56 | N-[5-[(3,5-difluorophenyl)methyl]-6-(1H-indazol-5-yl)-1H-indazol-3-yl]-4-piperazin-1-yl-benzamide; |
| 57 | N-[5-[(3,5-difluorophenyl)methyl]-6-(3-fluoro-5-hydroxy-phenyl)-1H-indazol-3-yl]-4-piperazin-1-yl-2-(tetrahydropyran-4-ylamino)benzamide; |
| 58 | N-[5-[(3,5-difluorophenyl)methyl]-6-(2-fluoro-5-hydroxy-phenyl)-1H-indazol-3-yl]-4-piperazin-1-yl-2-(tetrahydropyran-4-ylamino)benzamide; |
| 59 | N-[6-(2-aminopyrimidin-5-yl)-5-[(3,5-difluorophenyl)methyl]-1H-indazol-3-yl]-4-piperazin-1-yl-2-(tetrahydropyran-4-ylamino)benzamide; |
| 60 | N-[5-[(3,5-difluorophenyl)methyl]-6-(3H-imidazo[4,5-b]pyridin-6-yl)-1H-indazol-3-yl]-4-piperazin-1-yl-2-(tetrahydropyran-4-ylamino)benzamide; |
| 61 | N-[6-(5-amino-3-pyridyl)-5-[(3,5-difluorophenyl)methyl]-1H-indazol-3-yl]-4-piperazin-1-yl-2-(tetrahydropyran-4-ylamino)benzamide; |
| 62 | N-[6-(6-amino-3-pyridyl)-5-[(3,5-difluorophenyl)methyl]-1H-indazol-3-yl]-4-piperazin-1-yl-2-(tetrahydropyran-4-ylamino)benzamide; |
| 63 | N-[6-(6-amino-4-methyl-3-pyridyl)-5-[(3,5-difluorophenyl)methyl]-1H-indazol-3-yl]-4-piperazin-1-yl-2-(tetrahydropyran-4-ylamino)benzamide; |
| 64 | N-[5-[(3,5-difluorophenyl)methyl]-6-[4-(methylcarbamoyl)phenyl]-1H-indazol-3-yl]-4-piperazin-1-yl-2-(tetrahydropyran-4-ylamino)benzamide; |
| 65 | N-[5-[(3,5-difluorophenyl)methyl]-6-[3-(hydroxymethyl)phenyl]-1H-indazol-3-yl]-4-piperazin-1-yl-2-(tetrahydropyran-4-ylamino)benzamide; |
| 66 | N-[5-[(3,5-difluorophenyl)methyl]-6-[4-hydroxy-2-(trifluoromethyl)phenyl]-1H-indazol-3-yl]-4-piperazin-1-yl-2-(tetrahydropyran-4-ylamino)benzamide; |
| 67 | N-[5-[(3,5-difluorophenyl)methyl]-6-[4-hydroxy-3-methyl-phenyl]-1H-indazol-3-yl]-4-piperazin-1-yl-2-(tetrahydropyran-4-ylamino)benzamide; |
| 68 | N-[5-[(3,5-difluorophenyl)methyl]-6-(1H-pyrrolo[2,3-b]pyridin-5-yl)-1H-indazol-3-yl]-4-piperazin-1-yl-2-(tetrahydropyran-4-ylamino)benzamide; |
| 69 | N-[5-[(3,5-difluorophenyl)methyl]-6-(6-hydroxy-3-pyridyl)-1H-indazol-3-yl]-4-piperazin-1-yl-2-(tetrahydropyran-4-ylamino)benzamide; |
| 70 | N-[5-[(3,5-difluorophenyl)methyl]-6-phenyl-1H-indazol-3-yl]-4-piperazin-1-yl-2-(tetrahydropyran-4-ylamino)benzamide; |

-continued

| No. | Chemical Name |
|---|---|
| 71 | N-[5-[(3,5-difluorophenyl)methyl]-6-(3-methoxyphenyl)-1H-indazol-3-yl]-4-piperazin-1-yl-2-(tetrahydropyran-4-ylamino)benzamide; |
| 72 | N-[5-[(3,5-difluorophenyl)methyl]-6-(3-fluoro-4-hydroxy-phenyl)-1H-indazol-3-yl]-4-piperazin-1-yl-2-(tetrahydropyran-4-ylamino)benzamide; |
| 73 | N-[5-[(3,5-difluorophenyl)methyl]-6-(1H-indazol-5-yl)-1H-indazol-3-yl]-4-piperazin-1-yl-2-(tetrahydropyran-4-ylamino)benzamide; |
| 74 | N-[5-[(3,5-difluorophenyl)methyl]-6-pyrimidin-5-yl-1H-indazol-3-yl]-4-piperazin-1-yl-2-(tetrahydropyran-4-ylamino)benzamide; |
| 75 | N-[5-[(3,5-difluorophenyl)methyl]-6-(3-oxoisoindolin-5-yl)-1H-indazol-3-yl]-4-piperazin-1-yl-2-(tetrahydropyran-4-ylamino)benzamide; |
| 76 | N-[6-(2-aminopyrimidin-5-yl)-5-[(3,5-difluorophenyl)methyl]-1H-indazol-3-yl]-4-piperazin-1-yl-benzamide; |
| 77 | N-[6-(3-fluoro-4-hydroxy-phenyl)-5-[(3-fluorophenyl)methyl]-1H-indazol-3-yl]-2-(2-methoxyethylamino)-4-piperazin-1-yl-benzamide; |
| 78 | N-[6-[2-(3-hydroxyphenyl)ethynyl]-1H-indazol-3-yl]-4-piperazin-1-yl-2-(tetrahydropyran-4-ylamino)benzamide; |
| 79 | N-[5-[(3,5-difluorophenyl)methyl]-6-(4-pyridyl)-1H-indazol-3-yl]-4-piperazin-1-yl-2-(tetrahydropyran-4-ylamino)benzamide; |
| 80 | N-[5-[(3,5-difluorophenyl)methyl]-6-(3-pyridyl)-1H-indazol-3-yl]-4-piperazin-1-yl-2-(tetrahydropyran-4-ylamino)benzamide; |
| 81 | N-[6-(3-fluoro-4-hydroxy-phenyl)-5-[(3-fluorophenyl)methyl]-1H-indazol-3-yl]-4-piperazin-1-yl-2-(tetrahydropyran-4-ylamino)benzamide; |
| 82 | N-[6-(2-fluoro-4-hydroxy-phenyl)-5-[(3-fluorophenyl)methyl]-1H-indazol-3-yl]-4-piperazin-1-yl-2-(tetrahydropyran-4-ylamino)benzamide; |
| 83 | N-[5-[(3,5-difluorophenyl)methyl]-6-[4-(1-hydroxy-1-methyl-ethyl)phenyl]-1H-indazol-3-yl]-4-piperazin-1-yl-2-(tetrahydropyran-4-ylamino)benzamide; |
| 84 | N-[5-[(3,5-difluorophenyl)methyl]-6-(4-hydroxy-3-methyl-phenyl)-1H-indazol-3-yl]-4-piperazin-1-yl-benzamide; |
| 85 | N-[6-(2-aminopyrimidin-5-yl)-5-[(3-fluorophenyl)methyl]-1H-indazol-3-yl]-4-piperazin-1-yl-benzamide; |
| 86 | 6-[3-[4-(piperazin-1-ylmethyl)-3-(trifluoromethyl)phenoxy]prop-1-ynyl]-1H-indazol-3-amine; |
| 87 | 3-amino-5-(2,4-difluorobenzyl)-6-(4-hydroxyphenyl)-1H-indazole; |
| 88 | 3-amino-5-(2,6-difluorobenzyl)-6-(4-hydroxyphenyl)-1H-indazole |
| 89 | 3-amino-5-(2,5-difluorobenzyl)-6-(4-hydroxyphenyl)-1H-indazole; |
| 90 | 3-amino-5-(2,5-dimethylbenzyl)-6-(4-hydroxyphenyl)-1H-indazole; |
| 91 | 3-amino-5-(2,5-dichlorobenzyl)-6-(4-hydroxyphenyl)-1H-indazole; |
| 92 | 3-amino-5-(3,5-dichlorobenzyl)-6-(4-hydroxyphenyl)-1H-indazole; |
| 93 | 3-amino-5-(2,6-dichlorobenzyl)-6-(4-hydroxyphenyl)-1H-indazole; |
| 94 | 3-amino-5-(3-fluorobenzyl)-6-(4-hydroxyphenyl)-1H-indazole; |
| 95 | 3-[3-amino-5-[(2,4-difluorophenyl)methyl]-1H-indazol-6-yl]-4-methyl-phenol; |
| 96 | 3-[3-amino-5-[(2,5-difluorophenyl)methyl]-1H-indazol-6-yl]-4-methyl-phenol; |
| 97 | 3-[3-amino-5-[(2,5-dimethylphenyl)methyl]-1H-indazol-6-yl]-4-methyl-phenol; |
| 98 | 3-[3-amino-5-[(2,5-dichlororophenyl)methyl]-1H-indazol-6-yl]-4-methyl-phenol; |
| 99 | 3-[3-amino-5-[(3,5-dichlorophenyl)methyl]-1H-indazol-6-yl]-4-methyl-phenol; |
| 100 | 3-[3-amino-5-[(2,6-dichlorophenyl)methyl]-1H-indazol-6-yl]-4-methyl-phenol; |
| 101 | 3-[3-amino-5-[(3-fluorophenyl)methyl]-1H-indazol-6-yl]-4-methyl-phenol; |
| 102 | [5-[(2,4-difluorophenyl)methyl]-6-(4-hydroxyphenyl)-1H-indazol-3-yl]-4-(4-methylpiperazin-1-yl)-2-(tetrahydropyran-4-ylamino)benzamide; |
| 103 | N-[5-[(2,6-difluorophenyl)methyl]-6-(4-hydroxyphenyl)-1H-indazol-3-yl]-4-(4-methylpiperazin-1-yl)-2-(tetrahydropyran-4-ylamino)benzamide; |
| 104 | N-[5-[(2,3-difluorophenyl)methyl]-6-(4-hydroxyphenyl)-1H-indazol-3-yl]-4-(4-methylpiperazin-1-yl)-2-(tetrahydropyran-4-ylamino)benzamide; |
| 105 | N-[5-[(2,5-difluorophenyl)methyl]-6-(4-hydroxyphenyl)-1H-indazol-3-yl]-4-(4-methylpiperazin-1-yl)-2-(tetrahydropyran-4-ylamino)benzamide; |
| 106 | N-[5-[(2,5-dimethylpheny)methyl]-6-(4-hydroxyphenyl)-1H-indazol-3-yl]-4-(4-methylpiperazin-1-yl)-2-(tetrahydropyran-4-ylamino)benzamide; |
| 107 | N-[5-[(3,5-dimethylphenyl)methyl]-6-(4-hydroxyphenyl)-1H-indazol-3-yl]-4-(4-methylpiperazin-1-yl)-2-(tetrahydropyran-4-ylamino)benzamide; |
| 108 | N-[5-[(2,5-dichlorophenyl)methyl]-6-(4-hydroxyphenyl)-1H-indazol-3-yl]-4-(4-methylpiperazin-1-yl)-2-(tetrahydropyran-4-ylamino)benzamide; |
| 109 | N-[5-[(3,4-dichlorophenyl)methyl]-6-(4-hydroxyphenyl)-1H-indazol-3-yl]-4-(4-methylpiperazin-1-yl)-2-(tetrahydropyran-4-ylamino)benzamide; |
| 110 | N-[5-[(3,5-dichlorophenyl)methyl]-6-(4-hydroxyphenyl)-1H-indazol-3-yl]-4-(4-methylpiperazin-1-yl)-2-(tetrahydropyran-4-ylamino)benzamide; |
| 111 | N-[5-[(2,3-dichlorophenyl)methyl]-6-(4-hydroxyphenyl)-1H-indazol-3-yl]-4-(4-methylpiperazin-1-yl)-2-(tetrahydropyran-4-ylamino)benzamide |

The compounds of the present invention can be prepared by various methods according to the procedures described below. Compounds of formula (I) where X is —NH—, n is 0, $R_1$ is —CO—$R_6$, $R_3$ is —CH$_2$Ar and $R_4$ is aryl or heteroaryl [compounds of formula (Ia)] are prepared through the synthesis shown in Scheme 1 (Method A).

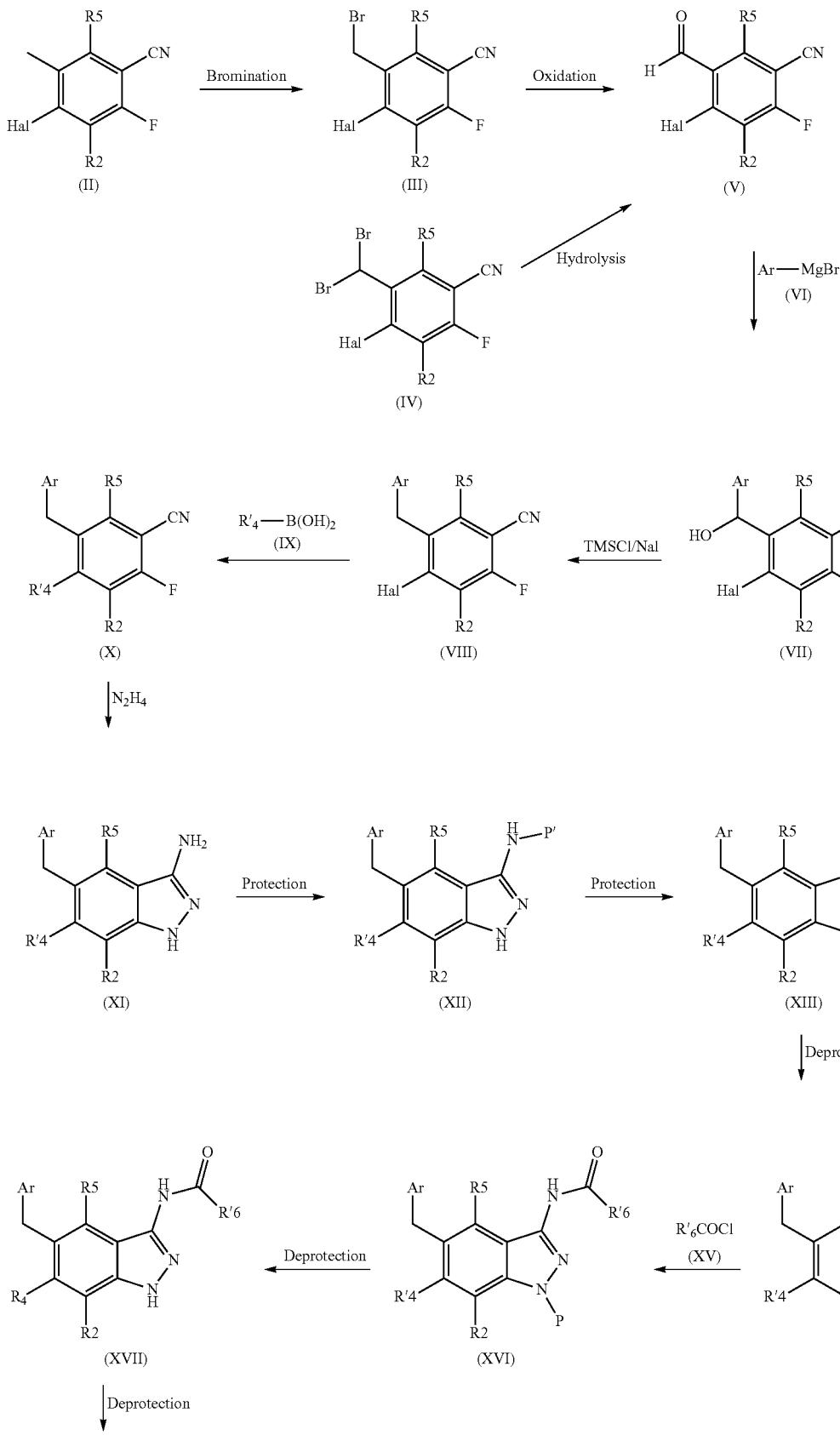
Scheme 1

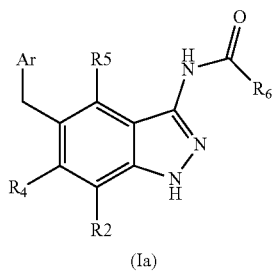

(Ia)

The Method A involves the bromination reaction of a compound of formula (II), where $R_2$ and $R_5$ are as defined above for compounds of formula (I) and Hal is an atom of chlorine, bromine or iodine. Compounds of formula (II) are converted to benzyl bromide (III) where $R_2$, $R_5$ and Hal are as defined above in the classic conditions of radical halogenation, using for example N-bromosuccinimide (NBS) in the presence of a radical initiator such as azobisisobutyronitrile (AIBN) in a solvent like carbon tetrachloride. With compounds of formula (III), the benzyl dibromide compound of formula (IV), where $R_2$, $R_5$ and Hal are as defined above, can be also isolated. The compounds of formula (III) and (IV) are converted into aldehydes of formula (V) where $R_2$, $R_5$ and Hal are as defined above. The conversion of (III) to (V) occurs through oxidation, for example with N-methylmorpholine-N-oxide. Compounds of formula (IV) are converted to (V) by hydrolysis, heating for example in N,N-dimethylformamide as solvent at a temperature between 120° and 140° C. Reaction of compounds of formula (V) with Grignard reagents of formula (VI) where Ar is as defined in the compounds of formula (I), provides compounds of formula (VII) where $R_2$, $R_5$ and Hal are as defined above. The compounds of formula (VII) are reduced to the compounds of formula (VIII) where $R_2$, $R_5$, Hal and Ar are as defined above by reaction with trimethylsilyl chloride in the presence of sodium iodide. The compounds of formula (VIII) are then submitted to Suzuki coupling reaction with an aryl boronic acid of formula (IX) where $R'_4$ is an aryl or heteroaryl as defined above for the compounds in formula (I), in which the hydroxyl or amino groups optionally present are protected with a protective group removable in acidic conditions, such as p-methoxybenzyl group, providing a compound of formula (X) where $R_2$, $R_5$, $R'_4$ and Ar are defined as above. The Suzuki coupling is typically carried out in a mixture of solvents like dioxane and water at high temperature, usually 100° C., using a catalyst such us tetrakis(triphenylphosphine)palladium, cesium carbonate as base and operating in a microwave reactor for a period of time between 75 and 180 minutes. Reaction of compounds of formula (X) with hydrazine in solvent like methanol or ethanol provides 3-amino-indazole compounds of formula (XI) where $R_2$, $R_5$, $R'_4$ and Ar are as defined above. Protection of amino group in position 3 of compounds of formula (XI) with a removable protective group in basic conditions, for example with the trifluoroacetamide group, followed by protection of the nitrogen atom in position 1 with a removable protective group in an acidic conditions, such as for example the triphenylmethyl group, provides compounds of formula, respectively (XII) and (XIII), where $R_2$, $R_5$, $R'_4$ and Ar are as defined above, P and P' are removable protective groups, respectively, in acidic or basic conditions. Deprotection of the amino group in position 3, for example with triethylamine in solvent like methanol, provides compounds of formula (XIV), where $R_2$, $R_5$, $R'_4$, Ar and P are as defined above, which may react with a compound of formula (XV), where $R'_6$ has the same meanings of $R_6$ in formula (I) and the primary and/or secondary amino groups present in $R'_6$ may be optionally protected with a protective group removable under basic conditions. The reaction is carried out by heating in a solvent like tetrahydrofuran or dioxane in presence of a tertiary amine such as triethylamine or diisopropylamine, providing compounds of formula (XVI) where $R_2$, $R_5$, $R'_4$, $R'_6$, Ar and P are defined as above. Deprotection in acidic conditions of removable protective group present in compounds of formula (XVI) provides compounds of formula (XVII) where $R_2$, $R_4$, $R_5$, $R'_6$ and Ar are as defined above. Final removal in basic conditions of the protective group present in compounds of formula (XVII) provides derivatives of formula (Ia) where $R_2$, $R_4$, $R_5$, $R_6$ and Ar are defined as in formula (I).

Compounds of formula (I) where X is —NH—, n is 0, $R_1$ is —CO—$R_6$, $R_3$ is —$CH_2$Ar and $R_4$ is aryl or heteroaryl [compounds of formula (Ia)] may be also prepared through the synthesis shown in Scheme 2 (Method B).

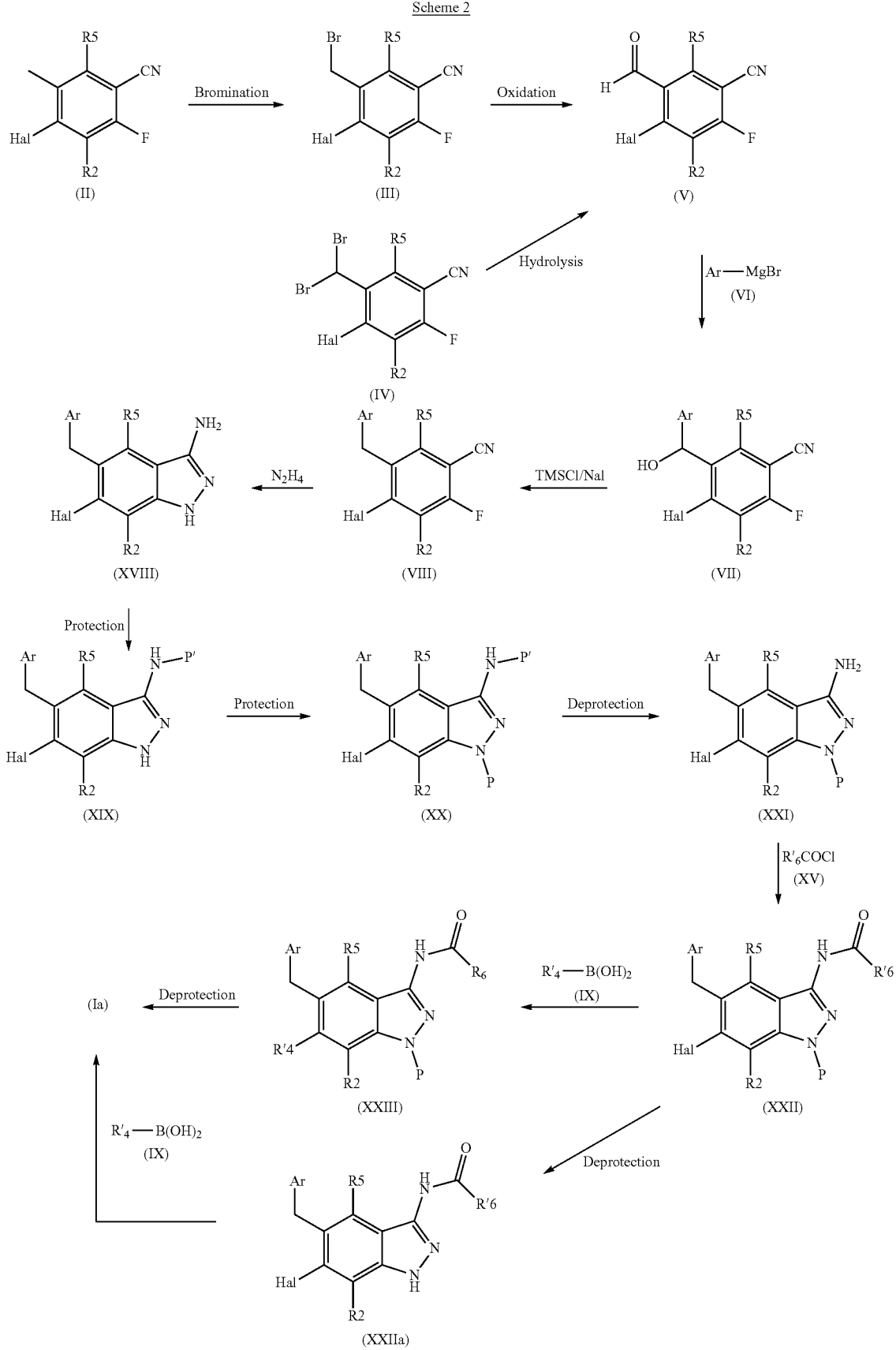
Scheme 2

The Method B involves the bromination reaction of a compound of formula (II), where $R_2$ and $R_5$ are as defined above for compounds of formula (I) and Hal is an atom of chlorine, bromine or iodine. Compounds of formula (II) are converted to benzyl bromide (III) where $R_2$, $R_5$ and Hal are as defined above in the classic conditions of radical halogenation, using for example N-bromosuccinimide (NBS) in the presence of a radical initiator such as azobisisobutyronitrile (AIBN) in a solvent like carbon tetrachloride. With compounds of formula (III), the benzyl dibromide compound of formula (IV), where $R_2$, $R_5$ and Hal are as defined above, can be isolated. The compounds of formula (III) and (IV) are converted into aldehydes of formula (V) where $R_2$, $R_5$ and Hal are as defined above. The conversion of (III) to (V) occurs through oxidation, for example with N-methyl-morpholine-N-oxide in solvent like acetonitrile. Compounds of formula (IV) are converted to (V) by hydrolysis, heating for example in N,N-dimethylformamide as solvent at a temperature between 120° and 140° C. Reaction of compounds of formula (V) with Grignard reagents of formula (VI) where Ar is as defined in the compounds of formula (I), provides compounds of formula (VII) where $R_2$, $R_5$ and Hal are as defined above. The compounds of formula (VII) are reduced to the compounds of formula (VIII) where $R_2$, $R_5$, Hal and Ar are as defined above for reaction with trimethylsilyl chloride in the presence of sodium iodide. The compounds of formula (VIII) are then submitted to reaction with hydrazine in solvent like methanol or ethanol providing 3-amino-indazole compounds of formula (XVIII) where $R_2$, $R_5$ and Ar are as defined above. Protection of amino group in position 3 of compounds of formula (XVIII) with a removable protective group in basic conditions, for example with the trifluoroacetamide group, followed by protection of the nitrogen atom in position 1 with a removable protective group in acidic conditions, such as the triphenylmethyl group, provides compounds of formula, respectively (XIX) and (XX), where $R_2$, $R_5$ and Ar are as defined above, P and P' are removable protective groups, respectively, in acidic or basic conditions. Deprotection of the amino group in position 3 provides compounds of formula (XXI), where $R_2$, $R_5$, Ar and P are as defined above, which may react with a compound of formula (XV), where $R'_6$ has the same meanings of $R_6$ in formula (I) and primary and/or secondary amino groups present in $R'_6$ are optionally protected with a protective group removable under basic conditions. The reaction is carried out by heating in a solvent like tetrahydrofuran or dioxane in presence of a tertiary amine such as triethylamine or diisopropylamine to give compounds of formula (XXII) where $R_2$, $R_5$, $R'_6$, Ar and P are as defined above. Compounds of formula (XXII) are submitted to Suzuki coupling reaction with an aryl boronic acid of formula (IX) where $R'_4$ is an aryl or heteroaryl as defined above for the compounds in formula (I), in which the hydroxyl or amino groups optionally present are eventually protected with a protective group removable in acidic conditions, such as p-methoxybenzyl to give compounds of formula (XXIII) where $R_2$, $R_5$, $R'_4$, $R'_6$, Ar and P are as defined above. The Suzuki coupling is typically carried out in a mixture of solvents like dioxane and water at high temperature, usually between 90° C. and 100° C., using as catalyst tetrakis(triphenylphosphine)palladium, cesium carbonate as base and operating in a microwave reactor for a period of time between 1 and 2 hours. Deprotection respectively in acidic and basic conditions of compounds of formula (XXIII) provides compounds of formula (Ia) where $R_2$, $R_4$, $R_5$, $R_6$ and Ar are defined as above. Alternatively, compounds of formula (XXII) can be deprotected to compounds of formula (XXIIa) where $R_2$, $R_5$, $R'_6$ and Ar are as defined above. Compounds of formula (XXIIa) are finally submitted to Suzuki coupling providing compounds of formula (Ia) where $R_2$, $R_4$, $R_5$, $R_6$ and Ar are defined as above.

Compounds of formula (I) where X is —NH—, n is 1, $R_1$ is —CO—$R_6$, $R_3$ is hydrogen and $R_4$ is aryl, heteroaryl or $(R_a)(R_b)ZC$ as defined above [compounds of formula (Ib)] may be prepared through the synthesis shown in Scheme 3 (Method C).

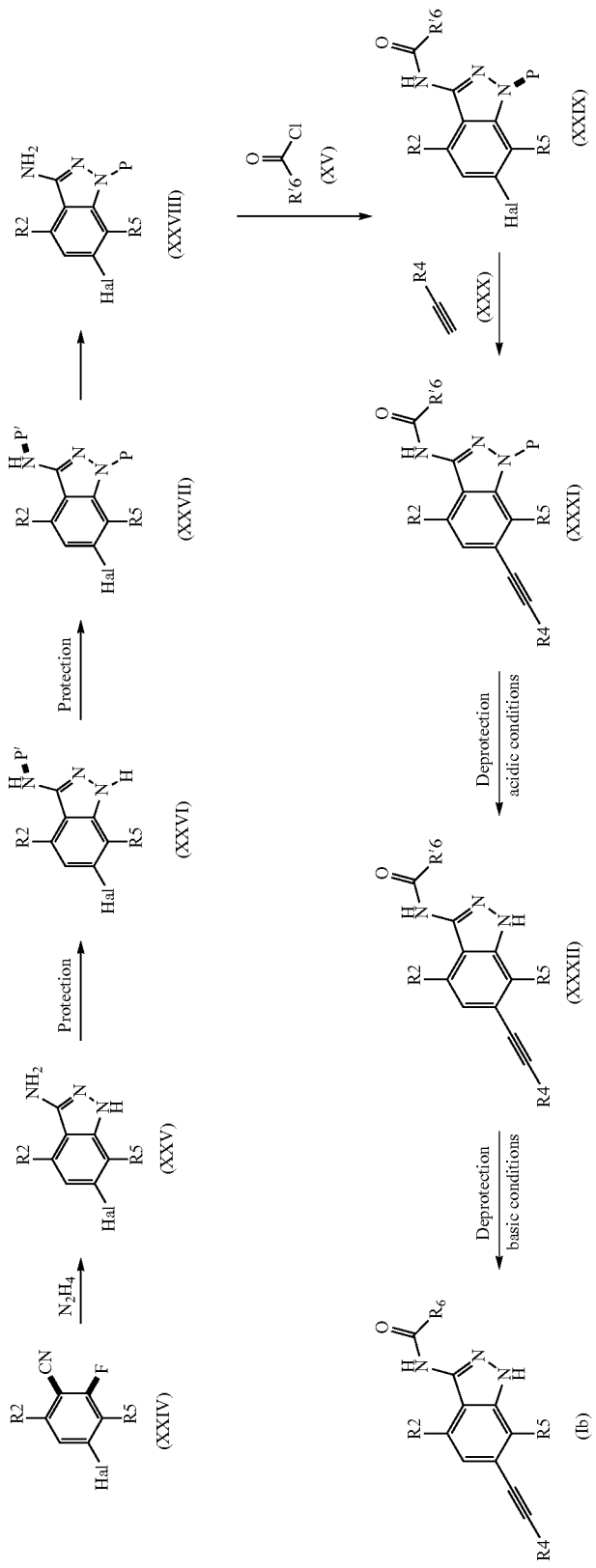

Following the synthetic pathway of Scheme 3 compounds of formula (XXIV) where $R_2$ and $R_5$ are defined as above for compounds of formula (I), are heated with hydrazine in solvents like ethanol or dioxane providing compounds of formula (XXV) that in turn are protected on the amino group in position 3 of the indazole ring with a removable protective group in basic conditions, for example with the trifluoroacetamide group, followed by protection of the nitrogen atom in position 1 with a removable protective group in acidic conditions, such as the triphenylmethyl group, affording compounds of formula, respectively (XXVI) and (XXVII), where $R_2$, $R_5$ are as defined above, P and P' are removable protective groups, respectively, in acidic or basic conditions. Compounds of formula (XXVII) are deprotected on position 3, for example with triethylamine in solvent like methanol, providing compounds of formula (XXVIII), where $R_2$, $R_5$ and P are as defined above. Compounds of formula (XXVIII) may react with a compound of formula (XV), where $R'_6$ has the same meanings of $R_6$ in formula (I) and primary and/or secondary amino groups present in $R'_6$ are optionally protected with a protective group removable under basic conditions. The reaction with chloride of formula (XV) is carried out by heating in a solvent like tetrahydrofuran to give compounds of formula (XXIX) where $R_2$, $R_5$, $R'_6$ and P are defined as above. Compounds of formula (XXIX) is thus submitted to Sonogashira reaction with compounds of formula (XXX) carrying on the alkynyl bond a group $R_4$, where $R_4$ is an aryl or heteroaryl as defined above for the compounds in formula (I). Compounds of formula (XXXI) where P, $R_2$, $R_4$, $R_5$ and $R'_6$ are defined as above are thus obtained. Sonogashira coupling is carried out heating the reaction in a microwave reactor for a period of time between 75 and 150 minutes, in presence for example of catalytic amount of palladium-bis(triphenylphosphine) dichloride and copper (I) iodide, ligands such as triphenylphosphine, triethylamine as base in solvent like dioxane or dimethylformamide. Compounds of formula (XXX) are known or can be prepared using available methodologies such as Sonogashira reaction between an aryl or heteroaryl bromide and a trialkylsilyl acetylene such as trimethylsilyl or triisopropylsilyl acetylene, followed by the removal of the trialkylsilyl group in basic conditions. Compounds of formula (XXXI) are then subjected to removal of the protective group P in acidic conditions by treatment, for example, with trifluoroacetic acid to provide compounds of formula (XXXII) where $R_2$, $R_4$, $R_5$ and $R'_6$ are as defined above. Finally removal of protective group on primary and secondary amines present in $R'_6$ with base like triethylamine in solvent like methanol, provides compounds of formula (Ib) where X is —NH—, n is 1, $R_1$ is —CO—$R_6$, $R_4$ is aryl or heteroaryl and $R_3$ is H.

Compounds of formula (I) where X is —NH—, n is 0, $R_1$ is hydrogen, $R_3$ is —YAr where Y is —$CH_2$— and $R_4$ is aryl or heteroaryl [compounds of formula (Ic)] are prepared through the synthesis shown in Scheme 4 (Method D).

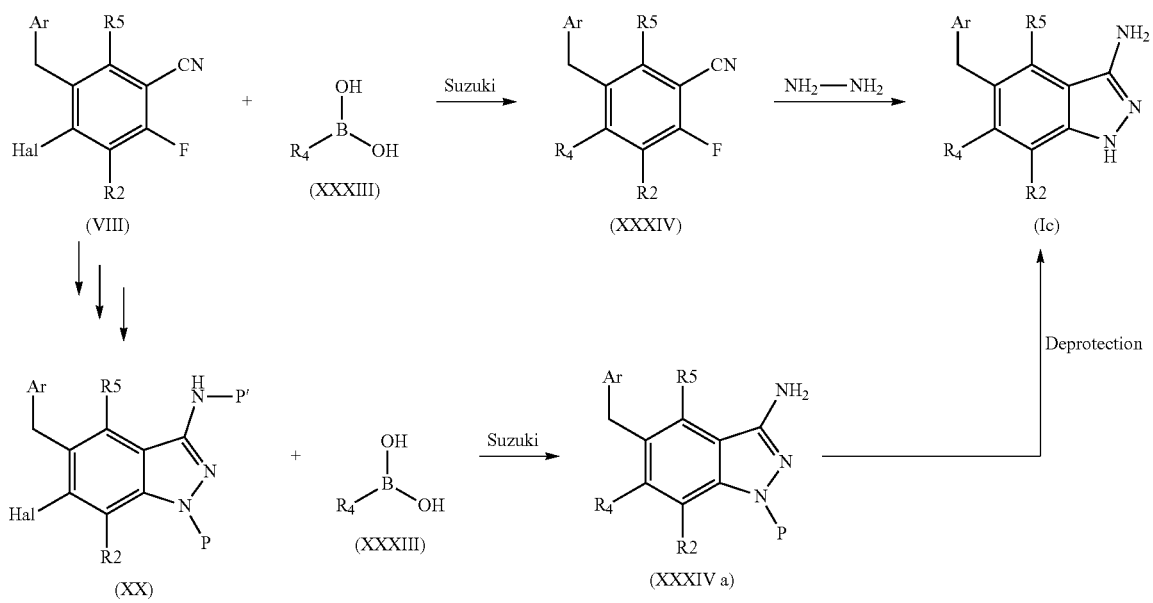

Scheme 4

Compounds of formula (VIII) are submitted to reaction with an aryl boronic acid of formula (XXXIII), where $R_4$ is an aryl or heteroaryl defined as above for the compounds of formula (I), under the conditions of the Suzuki reaction. Compounds of formula (XXXIV) where $R_2$, $R_4$, $R_5$ and Ar are as defined above can be isolated. The Suzuki coupling is typically carried out in a mixture of solvents like dioxane and water at high temperature, usually between 90° C. and 100° C., using as catalyst tetrakis(triphenylphosphine)palladium, cesium carbonate as base and operating in a microwave reactor for a period of time between 1 and 2 hours. Reaction of compounds (XXXIV) with hydrazine provides compounds of formula (Ic) where $R_2$, $R_4$ and $R_5$ are defined as above. Alternatively, compounds of formula (VIII), following the procedure reported in Scheme 2, are converted to compounds of formula (XX) which in turn are submitted to Suzuki coupling providing compounds of formula (XXXIVa) where $R_2$, $R_5$, $R_4$, P and Ar are as defined above. Compounds of formula (XXXIVa) are finally deprotected providing compounds of formula (Ic) where $R_2$, $R_4$, $R_5$ and Ar are defined as above.

Compounds of formula (I) where X is —NH—, n is 1, $R_1$ is hydrogen, $R_3$ is hydrogen and $R_4$ is aryl, heteroaryl or $(R_a)(R_b)ZC$ as defined above [compounds of formula (Id)] may be prepared through the synthesis shown in Scheme 5 (Method E).

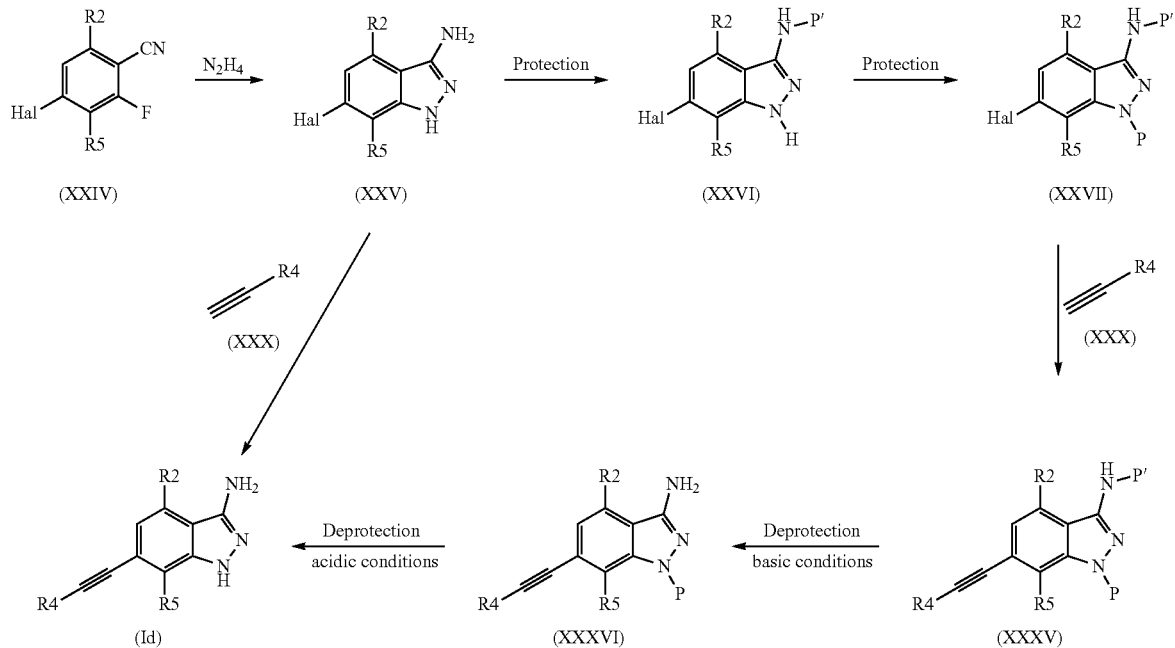

Scheme 5

Compounds of formula (XXVII), where $R_2$ and $R_5$ are defined as above for compounds of formula (I), have been described in the present document for the preparation shown in Scheme 3 starting from compounds of formula (XXIV). Compounds of formula (XXVII) are thus submitted to Suzuki coupling reaction with reagent (XXX). Usually Suzuki reaction is carried out in solvents like dioxane or dimethylformamide at high temperature, usually between 70° C. and 100° C. in presence of catalytic amount of catalysts like palladium-bis(triphenylphosphine)dichloride and copper (I) iodide, ligands such as triphenylphosphine and triethylamine as base, operating in a microwave reactor for a period of time between 2 and 10 hours. This procedure provides compounds of formula (XXXV) where $R_2$, $R_4$ and $R_5$ are defined as above, P and P' are removable protective groups, respectively, in acidic or basic conditions. Deprotection of compounds of formula (XXXV) in basic conditions, for example with triethylamine in methanol in a range of temperature between 20° C. and 50° C., followed by treatment with trifluoroacetic acid affords compounds of formula (Id) where $R_2$, $R_4$ and $R_5$ are defined as above. Alternatively, in certain cases compounds of formula (Id) where $R_2$, $R_5$ and $R_4$ are as defined above can directly prepared from compounds of formula (XXV) by Suzuki coupling with reagent (XXX).

The present invention provides a method for treating diseases linked or caused by certain protein kinases, their rearrangements and mutated forms. According to the present invention, compounds of formula (I) displays a potent modulation of kinase activity with regard to protein kinases ALK, ACK1, LTK, HCK, BLK, AXL, BMX, $DDR_2$, $DDR_1$, EPHB2, EPHA2, EPHA3, EPHA5, TRKA, TRKB, TRKC, CSF1R, ERBB4, RET, ROS1, JAK1, JAK2, JAK3, FRK, LYN, FYN, PI3K, Aurora 2, FGR, YES, SLK, $VEGFR_2$, RIPK2, MAP4K2, MAP4K5, TXK, CDK4, CDK6, CDK9, CAMKK2, PKCδ, IRAK4, $FGFR_3$, $FGFR_2$, TYK2, FER, LCK, MERTK, MELK, TIE2, BTK, BRK, and SRC. More particularly compounds of the invention preferably modulate the kinase activity of ALK, LTK, $DDR_2$, $DDR_1$, EPHB2, TRKA, JAK1, JAK2, JAK3, TRKB, TRKC, RET, ROS1, LYN, FYN, TYK2, SRC, HCK, PKCδ, TXK, and FGR.

In a panel of cell lines, compounds of the invention are for example more potent and selective ALK inhibitors than Crizotinib, especially against immortalized cell line murine BaF3 NPM/ALK carrying the drug resistant ALK mutation L1196M. Compounds of the invention are also potent modulators of cell proliferation against SUPM2, Karpas 299 and SUDHL1 cell lines from anaplastic large cell lymphoma positive for $CD_{30}$ and ALK. The compounds of the invention determine the arrest of cell proliferation in tested cancer cell lines. This effect is specific for ALK-dependent cell lines.

A further object of the invention relates therefore to compounds of formula (I) defined as above and to the use of same as drugs. The compounds of the invention, when administered to mammals with cancer, are therefore useful in controlling tumor growth and metastasis formation, especially in the treatment of cancers whose growth is driven by an abnormal kinase activity of protein like ALK, LTK, $DDR_2$, $DDR_1$, EPHB2, TRKA, JAK1, JAK2, JAK3, TRKB, TRKC, RET, ROS1, LYN, FYN, TYK2, SRC, HCK, PKCδ, TXK, FGR, by their rearrangements or by mutated forms like for example ALK L1196M, ALK F1174L, ALK L1152R, ALK G1269A, ALK C1156Y, ALK F1174V, ALK S1206Y, RET V804M, RET C634W, RET M918T, DDR2 T654I, and DDR2 T654M. This use of the compounds is a further object of the invention.

Examples of cancers that can be treated with the compounds of the invention are tumors of the breast, lung, in particular the non-small cell lung cancer, colon, liver, prostate, endometrium, ovary, stomach, esophagus, thyroid, pancreas and kidney. The compounds are useful in the treatment of melanoma, myeloma, rhabdomyosarcoma, Ewing's sarcoma, Kaposi's sarcoma, medulloblastoma, malignant glioma, glioblastoma and ependymoma.

Examples of tumors characterized by aberrant expression of ALK or its forms changed or rearranged and can advantageously be treated with compounds of the present invention are neuroblastoma, rhabdomyosarcoma, glioblastoma, inflammatory myofibroblastic tumor, mammary carcinoma, melanoma, sarcoma, Ewing's sarcoma, retinoblastoma, B-cell lymphoma, diffuse large B-cell anaplastic lymphoma, squamous cell carcinoma, thyroid carcinoma, pancreatic carcinoma, prostate carcinoma, and non-small cell lung cancer. The compounds of the invention are also useful as drugs for the treatment of neurodegenerative diseases such as Alzheimer's disease. This use is a further object of the invention.

The compounds of the invention may be administered to a patient in doses ranging from 0.1 mg to 1000 mg per Kg of body weight per day. A preferred route of administration is the one that uses a dosage approximately from 1 mg to 50 mg per Kg of body weight per day, with doses to be administered in 24 hours from approximately 70 mg to 3.5 g of active substance to a patient having weight of about 70 Kg. Such a way of administration can be adjusted to achieve a better therapeutic effect. For example, doses can be adapted depending on therapeutic situation of patients.

The active compounds according to the invention may be administered orally, intravenously, intramuscularly or subcutaneously. Determination of optimal dosages and routes of administration for a given patient are well known to experts in the field.

The compounds of the invention, when administered according to well-known therapeutic modalities, in combination with other agents used to induce regression of tumors, increase the antitumor effects of these compounds in a synergistic way.

Examples of drugs that can be used in combination with the compounds of the invention include hormonal agents such as anti-androgens and anti-estrogens, aromatase inhibitors, inhibitors of topoisomerase I, inhibitors of topoisomerase II, anti-mitotic agents, Platinum complexes, alkylating agents, intercalating agents on DNA, DNA-damaging agents, antimetabolites, kinase inhibitors, inhibitors of mTOR, inhibitors of histone deacetylase, inhibitors of farnesyl transferase, inhibitors of hypoxic response and monoclonal antibodies, such as cisplatin, carboplatin, doxorubicin, topotecan, taxol, taxotere, vincristine, 5-fluorouracil and decarbazine. The compounds of the invention can also be used in combination with radiotherapy. These uses in combination with the compounds of the invention are a further object of the invention.

Another object of the present invention relates to a compounds of formula (I) mixed with an excipient for pharmaceutical use. For therapeutic use, compounds of the invention can be properly formulated with ingredients or physiologically acceptable vehicles. Suitable dosage forms may vary depending on the specific compound and the route of administration. The dosage of the active substance shall be determined from time to time, based on the severity of the treated disease and the general condition of patients. Appropriate pharmaceutical compositions can be prepared by following the guidelines in Remington's Pharmaceutical Sciences, 18th ed. Mack Publishing Co.

Pharmaceutical compositions according to the present invention contains therapeutically effective amount of at least one compound according to the invention in mixture with other ingredients compatible with pharmaceuticals. Oral compositions generally include an inert diluent or an eatable support and can be packed into gelatine capsules or in tablets. Other possible forms of oral administration include capsules, pills, elixirs, suspensions and syrups.

Tablets, pills, capsules and similar compositions may contain the following ingredients, in addition to the compound of the formula (I): a binder, such as microcrystalline cellulose, gelatine or tragacanth; media such as starch or lactose, a disrupter such as alginic acid, primogel, corn starch and the like; a lubricant such as magnesium stearate; a condenser such as colloidal silicon dioxide; a sweetener such as sucrose or saccharine or a flavouring such as mint flavour, methyl salicylate or orange aroma. When the selected composition is in capsule form, it may contain in addition a vehicle such as a liquid fat oil. Other compositions may contain a variety of materials, such as glazing agents (for tablets and pills) such as sugar or shellac. The material used in the preparation of compositions should be pharmaceutically pure and non-toxic at doses used.

For the preparation of pharmaceutical compositions for parenteral administration, active ingredient may be included in solutions or suspensions, which may contain the following components: a sterile diluent such as water for injection, saline, oil, polyethylene glycol, glycerine, propylene glycol or other synthetic solvents; antibacterial agents such as benzyl alcohol; antioxidants such as ascorbic acid or sodium metabisulfite; chelating agents such as EDTA; buffers such as phosphates citrates acetates and agents to adjust the firmness of the solution such as sodium chloride or dextrose. Parenteral preparations can be enclosed in ampoules, syringes, glass vials or plastic.

The invention is further described by the following examples.

Chemistry Experimental Section and Examples

For a reference to any specific compound of formula (I) of the present invention, optionally in the form of a pharmaceutically acceptable salt, refer to the experimental section and claims. Referring to the examples that follow, compounds of the present invention have been synthesized using the methods described herein, or other methods, which are well known to any person skilled in the art.

All reactions were carried out under nitrogen atmosphere using anhydrous solvents unless otherwise specified. Unless otherwise noted, all materials were obtained from commercial suppliers, of the best grade and used without further purification. NMR spectra were recorded with an instrument Bruker 400 MHz at 298 K using CDCl3 ($\delta$=7.26 ppm), CD$_3$OD ($\delta$=3.31 ppm), or DMSO ($\delta$=2.50 ppm) as a solvent and internal standard. Chemical shifts (chemical shifts) ($\delta$) were scaled ppm and the coupling constants (J) have been reported in Hz. LCMS spectra were obtained with an instrument Agilent 1200 series 6110 or 6120 mass spectrometer with electrospray ionization and, excepted as otherwise indicated, the general LCMS conditions were as follows: Waters X Bridge C18 column (50 mm×4.6 mm×3.5 um), flow rate: 2.0 mL/min, column temperature: 40° C.; mobile phase: A: Water (0.05% TFA) and B: ACN (0.05% TFA); gradient: B from 5% to 100% for 1.6 min and hold 100% for 1.4 min; UV detection at 220 nm and 254 nm. Full scan mass range from 100 to 800 amu. Capillary voltage was 2.5 KV; source temperature was 120° C.; cone was 10 V. Mass are given as m/z ratio. General purification: flash column chromatography was performed on silica gel (Merck grade 9395, 60A).

As used herein the symbols and conventions used in the processes, schemes and examples are consistent with those used in the contemporary scientific literature, for example, the *Journal of Medicinal Chemistry*. The short forms and abbreviations used herein have the following meaning:

g (grams)
mg (milligrams)
ml (milliliters)
μM (micromolar)
mmol (millimoles)
h (hours)
bs (broad singlet)
bt (broad triplet)
m (multiplet)
d (doublet)
dd (doublet of doublet)
dt (doublet of triplet)
t (triplet)
tt (triplet of triplet)
s (singlet)
MHz (Mega-Hertz)
Hz (Hertz)
M (molar)
min (minutes)
mol (moles)
eq. (equivalent)
TFA (trifluoroacetic acid)
TFAA (trifluoroacetic anhydride)
$Boc_2O$ (di-tert-butyl dicarbonate)
PE (petroleum ether)
DIPEA (N,N-diisopropyl-N-ethylamine)
DMAP (4-dimethylamino-pyridine)
THF (tetrahydrofuran)
MeOH (Methanol)
TLC (thin layer chromatography)
TEA (triethylamine)
DMF (N,N-dimethyl formamide)
DCM (dichloromethane)
Hex (hexane)
PMB (para-methoxybenzyl)
DMSO (dimethylsulfoxide)
AcOEt (ethyl acetate)
ESI (electrospray ionization)

Preparative Example 1: Synthesis of 4-(4-carboxy-3-(2,2,2-trifluoro-N-(tetrahydropyran-4-yl)acet-amido)phenyl)-1-methylpiperazin-1-ium 2,2,2-trifluoroacetate The compound was prepared as previously described in WO2008/74749 and in WO2012101239 differing only in the hydrogenation step where hydrogen was used instead of cyclohexene.

a) Synthesis of tert-butyl 4-fluoro-2-nitrobenzoate

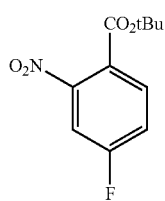 [SMILES: CC(C)(C)OC(=O)c1ccc(F)cc1[N+](=O)[O-]]

To a solution of 4-fluoro-2-nitro-benzoic acid (1.38 g, 7.5 mmol) in DCM (25 ml), $Boc_2O$ (3.27 g, 15 mmol) and DMAP (275 mg) were added. After 30 minutes, tert-butanol (75 mmol, 7 ml) was added and the reaction was stirred at room temperature for 24 h. The reaction mixture was then diluted with ethyl acetate and washed with HCl 1M, a saturated solution of aqueous $NaHCO_3$, a brine solution, dried over sodium sulfate, filtered and evaporated to dryness. The title compound was isolated in the form of a yellow solid (1.56 g, 86%).

$^1$H-NMR (400 MHz, $CDCl_3$) δ 7.78 (dd, J=8.6, 5.4 Hz, 1H), 7.48 (dd, J=7.8, 2.5 Hz, 1H), 7.33 (ddd, J=8.5, 7.6, 2.5 Hz, 1H), 1.53 (s, 9H).

b) Synthesis of tert-butyl 4-(4-methylpiperazin-1-yl)-2-nitrobenzoate

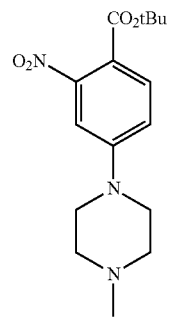 [SMILES: CN1CCN(c2ccc(C(=O)OC(C)(C)C)c([N+](=O)[O-])c2)CC1]

4-methylpiperazine (19 mmol, 2.15 ml) was added to a flask containing tert-butyl 4-fluoro-2-nitro-benzoate (6.46 mmol, 1.56 g) at room temperature. The mixture was stirred for 5 hours, water (30 ml) was added and stirred for 18 hours. The precipitate formed was filtered, rinsed with water and dried under vacuum to yield the title compound as a yellow solid (1.96 g, 95%).

$^1$H NMR (400 MHz, $CDCl_3$) δ 7.71 (d, J=8.8 Hz, 1H), 6.99 (d, J=2.1 Hz, 1H), 6.94 (dd, J=8.8, 2.2 Hz, 1H), 3.44-3.29 (m, 4H), 2.65-2.50 (m, 4H), 2.35 (s, 3H), 1.51 (s, 9H).

c) Synthesis of tert-butyl 2-amino-4-(4-methylpiperazin-1-yl)benzoate

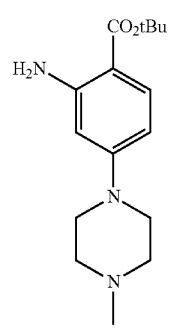

Tert-butyl 4-(4-methylpiperazin-1-yl)-2-nitrobenzoate (1.56 mmol, 500 mg) was dissolved in ethanol (10 ml), then Pd/C (25 mg) was added. Hydrogenation at atmosphere pressure was started and the mixture was stirred for 6 hours. The solution was filtered over a pad of celite and washed with methanol several times. Solvent was removed under vacuum affording the title compound as a white solid (442 mg, 97%).

¹H NMR (400 MHz, CDCl₃) δ 7.69 (d, J=9.0 Hz, 1H), 6.22 (dd, J=9.0, 2.5 Hz, 1H), 6.01 (d, J=2.4 Hz, 1H), 5.67 (bs, 2H), 3.35 (bs, 4H), 2.65 (bs, 4H), 2.40 (s, 3H), 1.56 (s, 9H).

d) Synthesis of tert-butyl 4-(4-methylpiperazin-1-yl)-2-(tetrahydropyran-4-ylamino)benzoate

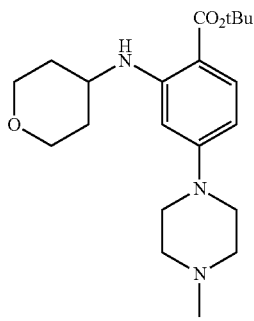 [SMILES: CN1CCN(c2ccc(C(=O)OC(C)(C)C)c(NC3CCOCC3)c2)CC1]

Under nitrogen atmosphere tert-butyl 2-amino-4-(4-methylpiperazin-1-yl)benzoate (1.51 mmol, 440 mg) was dissolved in DCM (15 ml). Pyranone (1.81 mmol, 168 µl) followed by TFA (3.93 mmol, 300 µl) were added. After 90 minutes of stirring at room temperature, tetramethylammonium triacetoxyborohydride (2.26 mmol, 596 mg) was added and the mixture stirred for 18 hours. Reaction was diluted with water, organic phase was separated with DCM, washed with HCl 0.5M, NaOH 1M, brine, dried over sodium sulfate, filtered and evaporated to dryness. The acidic aqueous phase were basified with NaOH 1M and extracted with DCM.

The title compound was isolated as orange oil (530 mg, 90%).

¹H NMR (400 MHz, CDCl₃) δ 7.92 (d, J=7.4 Hz, 1H), 7.75 (d, J=9.0 Hz, 1H), 6.15 (dd, J=9.0, 2.4 Hz, 1H), 6.01 (d, J=2.2 Hz, 1H), 4.02 (t, J=3.9 Hz, 1H), 3.98 (dd, J=10.4, 4.9 Hz, 2H), 3.64-3.50 (m, 3H), 3.34 (s, 4H), 2.64 (s, 4H), 2.42 (s, 3H), 2.04 (dd, J=12.9, 1.8 Hz, 2H), 1.73-1.59 (m, 2H), 1.55 (s, 9H).

e) Synthesis of tert-butyl 4-(4-methylpiperazin-1-yl)-2-(2,2,2-trifluoro-N-(tetrahydropyran-4-yl)-acetamido) benzoate

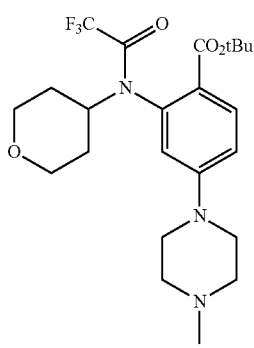 [SMILES: CN1CCN(c2ccc(C(=O)OC(C)(C)C)c(N(C(=O)C(F)(F)F)C3CCOCC3)c2)CC1]

Under nitrogen atmosphere tert-butyl 4-(4-methylpiperazin-1-yl)-2-(tetrahydropyran-4-ylamino)benzoate (0.69 mmol, 260 mg) was dissolved in DCM (7 ml) and cooled to 0° C. Then TEA (1.1 mmol, 154 µl) was added followed by a slow addition of TFAA (0.9 mmol, 253 µl). Reaction was terminated after 4 hours, washed with water, diluted with DCM, washed with a saturated solution of aqueous NaHCO₃, brine solution, dried over sodium sulfate, filtered and evaporated to dryness affording the title compound as an orange foam (253 mg, 78%).

¹H NMR (400 MHz, CDCl₃) δ 7.95 (d, J=8.9 Hz, 1H), 6.91 (dd, J=8.9, 2.6 Hz, 1H), 6.55 (d, J=2.4 Hz, 1H), 4.64 (ddd, J=12.1, 8.1, 4.0 Hz, 1H), 4.05-3.95 (m, 2H), 3.90 (dd, J=11.6, 4.3 Hz, 1H), 3.64-3.32 (m, 6H), 2.81 (s, 3H), 2.52 (dd, J=16.0, 9.9 Hz, 4H), 2.12 (d, J=12.7 Hz, 1H), 1.79-1.32 (m, 10H), 1.32-1.02 (m, 2H).

f) Synthesis of 4-(4-carboxy-3-(2,2,2-trifluoro-N-(tetrahydropyran-4-yl)acetamido)phenyl)-1-methyl-piperazin-1-ium 2,2,2-trifluoroacetate

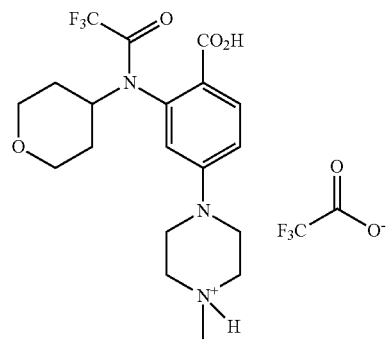 [SMILES: C[NH+]1CCN(c2ccc(C(=O)O)c(N(C(=O)C(F)(F)F)C3CCOCC3)c2)CC1 ; O=C([O-])C(F)(F)F]

To a cooled solution of tert-butyl 4-(4-methylpiperazin-1-yl)-2-(2,2,2-trifluoro-N-(tetrahydropyran-4-yl) acetamido) benzoate (0.65 mmol, 310 mg) at 0° C. in DCM (3 ml) was added TFA (13 mmol, 1 ml). The reaction was stirred at room temperature for 20 hours and the solvent removed. The residue was washed with a mixture of ethyl ether and hexane affording the title compound as a brown solid (360 mg, 75%).

¹H NMR (400 MHz, DMSO-d₆) δ 12.84 (s, 1H), 9.86 (s, 1H), 7.91 (d, J=8.9 Hz, 1H), 7.12 (dd, J=9.0, 2.5 Hz, 1H), 6.98 (d, J=2.5 Hz, 1H), 4.54-4.40 (m, 1H), 4.10 (d, J=10.2 Hz, 2H), 3.86 (dd, J=7.4, 4.5 Hz, 1H), 3.78 (dd, J=11.1, 4.5 Hz, 1H), 3.54 (d, J=9.9 Hz, 2H), 3.46-3.30 (m, 3H), 3.25-2.98 (m, 4H), 2.87 (s, 3H), 1.95 (d, J=10.8 Hz, 1H), 1.67-1.39 (m, 2H), 1.07-0.95 (m, 1H).

Preparative Example 2: Synthesis of 2-[2-methoxy-ethyl-(2,2,2-trifluoroacetyl)amino]-4-(4-methylpiperazin-4-ium-1-yl)benzoic acid; 2,2,2-trifluoroacetate a) Synthesis of tert-butyl 2-(2-methoxyethylamino)-4-(4-methylpiperazin-1-yl)benzoate

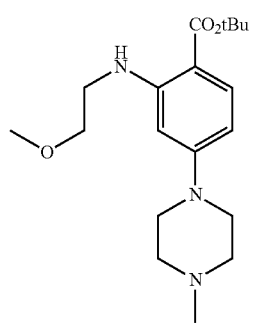 [SMILES: COCCNc1cc(N2CCN(C)CC2)ccc1C(=O)OC(C)(C)C]

A solution of 1,1-2-trimethoxyethane (0.1 mol, 12 g) in 1M HCl (100 ml) was heated at 100° C. for 2 h. The cooled mixture was extracted with DCM (5×30 ml) and the organic solution dried (3A molecular sieves). Tert-butyl 2-amino-4-(4-methylpiperazin-1-yl)benzoate (10 mmol, 2.91 g) was added and the resultant solution stirred under nitrogen for 20 min. TFA (20 mmol, 2.3 g) and sodium triacetoxyborohydride (15 mmol, 1.8 g) were added and the reaction mixture stirred under nitrogen at room temperature for 16 h. Saturated sodium bicarbonate (60 ml) was added portion wise and the resultant mixture stirred for 0.5 h and extracted with DCM (2×100 ml). The organic solution was dried and the solvent removed under vacuum. The title compound was obtained as orange oil (2.1 g, 60%).

b) Synthesis of tert-butyl 2-[2-methoxyethyl-(2,2,2-trifluoroacetyl)amino]-4-(4-methylpiperazin-1-yl)benzoate

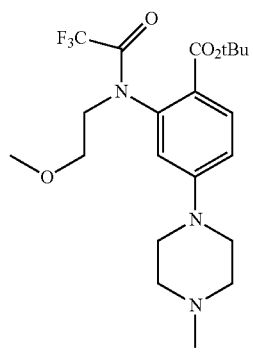 [SMILES: COCCN(C(=O)C(F)(F)F)c1cc(N2CCN(C)CC2)ccc1C(=O)OC(C)(C)C]

Under nitrogen atmosphere, to a solution of tert-butyl 2-(2-methoxyethylamino)-4-(4-methylpiperazin-1-yl)benzoate (6 mmol, 2.1 g) in DCM (10 ml) was added TEA (9.6 mol, 960 mg) at 0° C. TFAA (8 mol, 1.68 g) was then added slowly. The mixture was stirred at room temperature for 4 h and then partitioned between DCM and water. The organic phase was washed with saturated NaHCO₃ solution and brine. The resulting solution was dried over sodium sulfate and evaporated to dryness. The title compound was obtained as orange foam (2.3 g, over 86%).

c) Synthesis of 2-[2-methoxyethyl-(2,2,2-trifluoroacetyl)amino]-4-(4-methylpiperazin-4-ium-1-yl)benzoic Acid; 2,2,2-trifluoroacetate

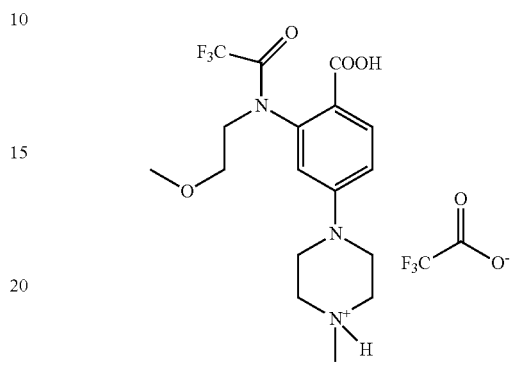

To a solution of tert-butyl 2-[2-methoxyethyl-(2,2,2-trifluoroacetyl)amino]-4-(4-methylpiperazin-1-yl)benzoate (5.2 mol, 2.3 g) in DCM (10 ml) at 0° C. was added TFA (0.1 mol, 11.4 g). The reaction was stirred at room temperature for 20 h. The solvent was removed under vacuum. The residue was washed with Et₂O/Hexane and dried under vacuum. The title compound was obtained as a brown solid (1.3 g, 52%).

Preparative Example 3: Synthesis of 4-(4-methyl-piperazin-4-ium-1-yl)-2-[tetrahydropyran-4-yl-(2,2,2-trifluoroacetyl)amino]benzoyl chloride [XV; R'₆=4-(4-methylpiperazin-1-yl)-2-(2,2,2-trifluoro-N-(tetrahydropyran-4-yl)-acetamido)phenyl]

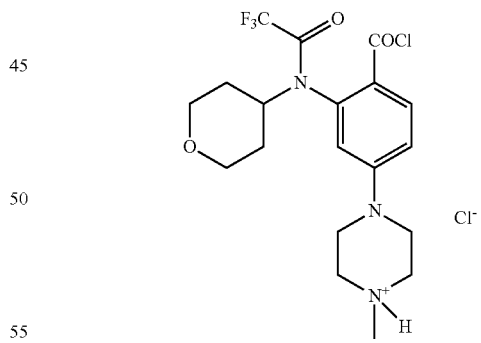

Under nitrogen atmosphere 4-(4-carboxy-3-(2,2,2-trifluoro-N-(tetrahydropyran-4-yl)acetamido)phenyl)-1-methylpiperazin-1-ium 2,2,2-trifluoroacetate (0.58 mmol, 310 mg) was dissolved in DCM (6 ml). DMF was added (1 drop) and the mixture cooled to 0° C. A 2M solution of (COCl)₂ in DCM (1.45 ml) was added slowly. Reaction was stirred for 3 hours at room temperature. Solvent was removed and the crude was dried under vacuum for at least 2 hours affording the title compound as pale yellow powder. The crude solid compound was used without further purification.

Preparative Example 4: Synthesis of 2-[2-methoxy-ethyl-(2,2,2-trifluoroacetyl)amino]-4-(4-methylpiperazin-1-yl)benzoyl chloride [XV; R'$_6$=4-(4-methyl-piperazin-1-yl)-2-(2,2,2-trifluoro-N-(2-methoxyethyl)-acetamido)phenyl]

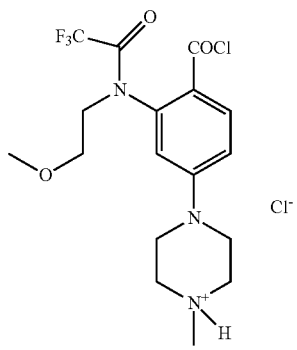 [SMILES: COCCN(C(=O)C(F)(F)F)c1cc(N2CC[NH+](C)CC2)ccc1C(=O)Cl ; [Cl-]]

Under nitrogen atmosphere, to a solution of 2-[2-methoxyethyl-(2,2,2-trifluoroacetyl)amino]-4-(4-methyl-piperazin-4-ium-1-yl)benzoic acid; 2,2,2-trifluoroacetate (2.7 mmol, 1.3 g) in DCM (10 ml) was added DMF (1 drop) at 0° C. (COCl)$_2$ (5.4 mmol, 0.67 g) was then added carefully. The mixture was stirred for 3 h and the solvent was removed. The residue was dried under vacuum for at least 2 h. The title compound as solid powder was used without further purification.

Preparative Example 5: Synthesis of 4-(4-methyl-piperazin-4-ium-1-yl)benzoyl chloride [XV; R'$_{6=4}$-(4-methylpiperazin-1-yl)-2-phenyl]

a) Synthesis of 4-(4-methylpiperazin-1-yl)benzonitrile

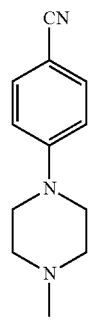

To a solution of 4-fluorobenzonitrile (0.041 mol, 5 g) in DMF (10 ml) were added K$_2$CO$_3$ (0.082 mol, 11.4 g) and 1-methylpiperazine (0.062 mol, 6.15 g). The mixture was stirred over 18 h at 100° C. The mixture was partitioned between water and ethyl acetate. The organic phase was washed with water and brine. The resulting solution was dried over sodium sulfate and evaporated to dryness. The title compound was obtained as a white solid and used without further purification (7 g, 84%).

(ESI+) MS: m/z 202.3 (MH$^+$).

b) Synthesis of 4-(4-methylpiperazin-4-ium-1-yl)benzoic Acid chloride

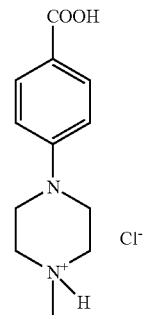 [SMILES: C[NH+]1CCN(c2ccc(C(=O)O)cc2)CC1 ; [Cl-]]

4-(4-Methylpiperazin-1-yl)benzonitrile (0.035 mmol, 7 g) was dissolved in concentrated HCl (10 ml) at 0° C. and the resulting solution was immediately warmed up to 100° C. and stirred for 5 h. The solvent was removed and the residue was dried affording the title compound as a white solid (6.5 g, 73%).

(ESI+) MS: m/z 221.2 (MH$^+$).

c) Synthesis of 4-(4-methylpiperazin-4-ium-1-yl)benzoyl chloride

Under nitrogen atmosphere 4-(4-methylpiperazin-4-ium-1-yl)benzoic acid chloride (3 mmol, 0.77 g) was dissolved in SOCl$_2$ (3 ml) at room temperature. The mixture was stirred for 30 minutes at 80° C. and the solvent was removed. The residue was dried under vacuum for at least 2 h. The title compound was used without further purification.

Preparative Example 6: Synthesis of N-(6-bromo-1-trityl-1H-indazol-3-yl)-4-(4-methylpiperazin-1-yl)-2-(2,2,2-trifluoro-N-(tetrahydropyran-4-yl)acetamido)benzamide [XXIX; $R_2=R_5$=H; Hal=Br; P=Trityl; $R'_6$=4-(4-methylpiperazin-1-yl)-2-(2,2,2-trifluoro-N-(tetrahydropyran-4-yl)-acetamido)phenyl]

a) Synthesis of 6-bromo-1H-indazol-3-amine [XXV; $R_2=R_5$=H; Hal=Br]

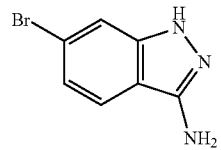 [SMILES: Nc1n[nH]c2cc(Br)ccc12]

2-Fluoro-4-bromo-benzonitrile (26.9 mmol, 5.38 g) and hydrazine hydrate 50% (107.6 mmol, 6.7 ml) were dissolved in ethanol (90 ml) and heated at 70° C. for 5 hours. After cooling to room temperature the title compound was filtered and isolated as a white solid (4.36 g, 76%).

$^1$H NMR (400 MHz, DMSO-$d_6$) δ 11.51 (s, 1H), 7.63 (dd, J=8.5, 0.5 Hz, 1H), 7.42 (dd, J=1.6, 0.5 Hz, 1H), 7.02 (dd, J=8.5, 1.6 Hz, 1H), 5.47 (s, 2H).

$^{13}$C NMR (101 MHz, DMSO-$d_6$) δ 149.4, 142.1, 122.1, 120.3, 119.8, 113.1, 111.8.

(ESI+) MS: m/z 233.1 (MNa+).

b) Synthesis of N-(6-bromo-1H-indazol-3-yl)-2,2,2-trifluoroacetamide [XXVI; $R_2=R_5$=H; Hal=Br; P'=2,2,2-trifluoroacetyl]

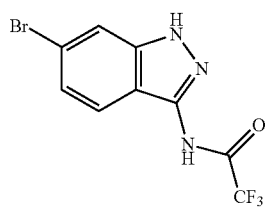

Under nitrogen atmosphere to a cooled suspension of 6-bromo-1H-indazol-3-amine (2.24 mmol, 475 mg) in a mixture of DCM (15 ml) and THF (2 ml), was slowly added TFA (6.7 mmol, 0.9 ml). When reaction is completed, solvent was removed and the crude dissolved in ethyl acetate, washed with a saturated solution of aqueous NaHCO$_3$, dried over sodium sulfate, filtered and evaporated to dryness.

The title compound was isolated as a white solid (789 mg, 99%).

$^1$H NMR (400 MHz, CDCl$_3$) δ 8.73 (s, 1H), 8.68-8.61 (m, 1H), 8.16 (d, J=8.7 Hz, 1H), 7.66 (dd, J=8.8, 1.7 Hz, 1H).

$^{13}$C NMR (101 MHz, CDCl$_3$) δ 145.6, 142.1, 130.4, 127.0, 125.6, 118.7, 118.2, 116.8, 113.9.

(ESI+) MS: m/z 306.1 (MH+).

c) Synthesis of N-(6-bromo-1-trityl-1H-indazol-3-yl)-2,2,2-trifluoroacetamide [XXVII; $R_2=R_5$=H; Hal=Br; P=Trityl; P'=2,2,2-trifluoroacetyl]

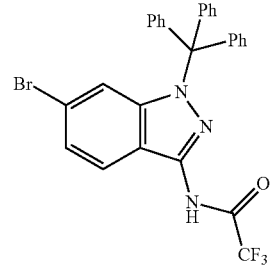 [SMILES: O=C(Nc1nn(C(c2ccccc2)(c2ccccc2)c2ccccc2)c2cc(Br)ccc12)C(F)(F)F]

Under nitrogen atmosphere N-(6-bromo-1H-indazol-3-yl)-2,2,2-trifluoroacetamide (2.24 mmol, 1.2 g) was dissolved in DCM (10 ml) and THF (2 ml). TEA (5.37 mmol, 748 µl) was added followed by trityl chloride (2.69 mmol, 749 mg). Reaction was stirred at room temperature for 48 hours. The mixture was washed with a saturated solution of aqueous NH$_4$Cl, water, dried over sodium sulfate, filtered and evaporated to dryness.

The crude was purified by flash column chromatography with DCM/Hex 3:7 1:1 affording the title compound as a white solid (815 mg, 68%).

$^1$H NMR (400 MHz, CDCl$_3$) δ 9.78 (s, 3H), 8.00 (d, J=8.9 Hz, 3H), 7.44-7.26 (m, 56H), 7.26-7.09 (m, 23H), 6.59 (d, J=1.1 Hz, 2H).

$^{13}$C NMR (101 MHz, CDCl$_3$) δ 154.8 (q, J=37 Hz), 143.3, 141.9, 136.5, 130.2, 128.0 (2C), 125.0, 124.2, 121.6, 120.2, 116.9, 116.4, 114.5, 79.2.

(ESI−) MS: m/z 548.1 (M-H$^-$).

d) Synthesis of 6-bromo-1-trityl-1H-indazol-3-amine [XXVIII; $R_2=R_5$=H; Hal=Br; P=Trityl]

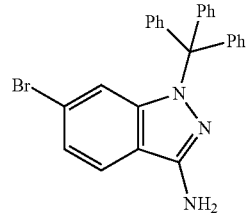 [SMILES: Nc1nn(C(c2ccccc2)(c2ccccc2)c2ccccc2)c2cc(Br)ccc12]

N-(6-bromo-1-trityl-1H-indazol-3-yl)-2,2,2-trifluoroacetamide (1.07 mmol, 590 mg) was dissolved in methanol (5 ml). TEA (3.2 mmol, 450 µl) was then added and the mixture was stirred at 70° C. for 18 hours. Solvent was removed and the crude purified by flash column chromatography with DCM/Hex 95:5.

$^1$H NMR (400 MHz, CDCl$_3$) δ 7.36-7.19 (m, 16H), 7.05 (dd, J=8.5, 1.5 Hz, 1H), 6.42 (d, J=1.2 Hz, 1H), 4.33-3.47 (m, 2H).

$^{13}$C NMR (101 MHz, CDCl$_3$) δ 147.4, 143.9, 142.9, 130.0, 127.8, 127.6, 127.3, 122.8, 120.9, 120.4, 116.8, 116.2, 77.9.

(ESI+) MS: m/z 453.6 (MH+).

e) Synthesis of N-(6-bromo-1-trityl-1H-indazol-3-yl)-4-(4-methylpiperazin-1-yl)-2-(2,2,2-trifluoro-N-(tetrahydropyran-4-yl)acetamido)benzamide [XXIX; R$_2$=R$_5$=H; Hal=Br; P=Trityl; R'$_{6=4}$-(4-methylpiperazin-1-yl)-2-(2,2,2-trifluoro-N-(tetrahydropyran-4-yl)-acetamido)phenyl]

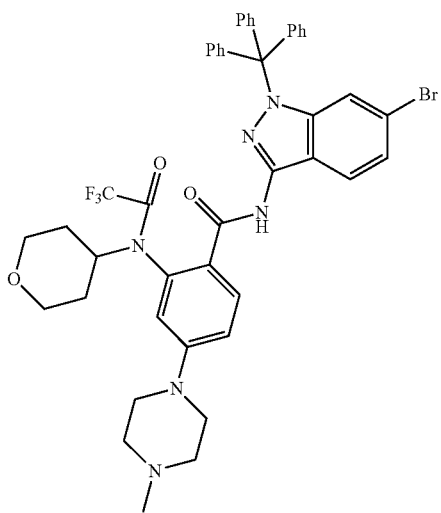 [SMILES: CN1CCN(c2ccc(C(=O)Nc3nn(C(c4ccccc4)(c4ccccc4)c4ccccc4)c4cc(Br)ccc34)c(N(C(=O)C(F)(F)F)C3CCOCC3)c2)CC1]

Under nitrogen atmosphere 6-bromo-1-trityl-1H-indazol-3-amine (0.7 mmol, 319 mg) was dissolved in a bottom round flask with THF (2 ml). DMAP (0.07 mmol, 7 mg) and DIPEA (3.48 mmol, 606 µl) were added at 0° C. A solution of 4-(4-methylpiperazin-4-ium-1-yl)-2-[tetrahydropyran-4-yl-(2,2,2-trifluoroacetyl)amino]benzoyl chloride (0.58 mmol) in DCM (2 ml) is slowly added to the cooled flask. Reaction was stirred at room temperature for 18 hours. The reaction mixture was diluted with DCM, washed with NaOH 1M, brine, dried over sodium sulfate, filtered and evaporated to dryness.

The crude was purified by flash column chromatography with eluent DCM/MeOH/NH$_4$OH 96:4:0.1 affording the title compound as a yellow solid (336 mg, 68%).

$^1$H NMR (400 MHz, CDCl$_3$) δ 8.26 (s, 1H), 7.82 (d, J=7.9 Hz, 1H), 7.69 (d, J=7.8 Hz, 1H), 7.38-7.24 (m, 10H), 7.24-7.07 (m, 6H), 6.89 (d, J=8.8 Hz, 1H), 6.65 (s, 1H), 6.49 (s, 1H), 4.67 (t, J=11.0 Hz, 1H), 3.99 (d, J=8.6 Hz, 1H), 3.83 (d, J=7.9 Hz, 1H), 3.63-3.20 (m, 6H), 2.63 (s, 4H), 2.41 (s, 3H), 2.10 (d, J=11.8 Hz, 1H), 1.73 (dd, J=34.6, 10.4 Hz, 2H), 1.43-1.12 (m, 1H).

$^{13}$C NMR (101 MHz, CDCl$_3$) δ 163.9, 156.4, 153.1, 143.4, 142.3, 139.4, 137.0, 130.2, 129.7, 127.9, 127.7, 124.7, 124.5, 122.5, 121.1, 117.8, 117.3, 116.6, 114.2, 78.8, 67.3, 67.3, 56.1, 55.4, 54.6, 47.3, 46.1, 31.4, 29.8, 29.6.

(ESI−) MS: m/z 849.2 (M-H$^-$).

Preparative Example 7: Synthesis of 3-ethynylphenol [XXX; R$_4$=3-hydroxyphenyl]

a) Synthesis of 3-(triisopropylsilyl)ethynyl)phenol

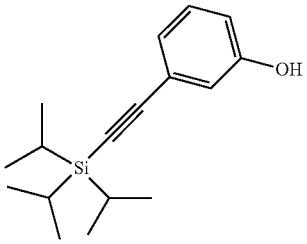 [SMILES: CC(C)[Si](C#Cc1cccc(O)c1)(C(C)C)C(C)C]

In a microwave vial under argon atmosphere were added respectively 3-bromo-phenol (0.58 mmol, 65 µl), triisopropylsilyl-acetylene (1.16 mmol, 260 µl), PdCl$_2$(PPh$_3$)$_2$ (0.023 mmol, 16 mg), CuI (0.023 mmol, 4.5 mg), triphenyl phosphine (0.046 mmol, 12 mg) and TEA (2.9 mmol, 400 µl). The reagents were dissolved with 6 ml of degassed dioxane and stirred for 5 minutes to dissolve the suspension. The reaction was carried out under irradiation at 70° C. for 75 minutes. The crude was purified by flash column chromatography with eluent Hexane/AcOEt 9:1 affording the title compound as yellow oil (31 mg, 20%).

$^1$H NMR (400 MHz, CDCl$_3$) δ 7.23-6.75 (m, 4H), 4.75 (bs, 1H), 1.15 (s, 21H).

b) Synthesis of 3-ethynylphenol [XXX; R$_4$=3-hydroxyphenyl]

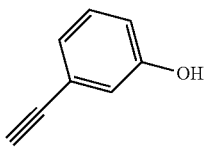

3-(triisopropylsilyl)ethynyl)phenol (0.11 mmol, 31 mg) was dissolved in THF (1 ml) under nitrogen atmosphere and TBAF 1M in THF was added (0.12 mmol, 120 µl) for 1 h at room temperature. The reaction mixture was diluted with DCM, washed with brine, dried over sodium sulfate, filtered and evaporated to dryness.

The crude was purified by flash column chromatography with eluent Hexane/AcOEt 9:1 affording the title compound as yellow oil (13 mg, 95%).

$^1$H NMR (400 MHz, CDCl$_3$) δ 7.25-6.73 (m, 4H), 4.75 (bs, 1H), 3.0 (s, 1H).

Example 1 (Method C): synthesis of N-[6-[2-(3-hydroxyphenyl)ethynyl]-1H-indazol-3-yl]-4-(4-methylpiperazin-1-yl)-2-(tetrahydropyran-4-ylamino)benzamide [(Ib); R$_2$=R$_5$=H; R$_4$=3-hydrohy-phenyl; R$_6$=4-(4-methylpiperazin-1-yl)-2-(tetrahydropyran-4-ylamino)phenyl]

a) Synthesis of N-(6-((3-hydroxyphenyl)ethynyl)-1-trityl-1H-indazol-3-yl)-4-(4-methylpiperazin-1-yl)-2-(2,2,2-trifluoro-N-(tetrahydropyran-4-yl)acetamido)benzamide [XXXI; R$_2$=R$_5$=H; P=Trityl; R$_4$=3-hydrohy-phenyl; R'$_6$=4-(4-methylpiperazin-1-yl)-2-(2,2,2-trifluoro-N-(tetrahydropyran-4-yl)-acetamido)phenyl]

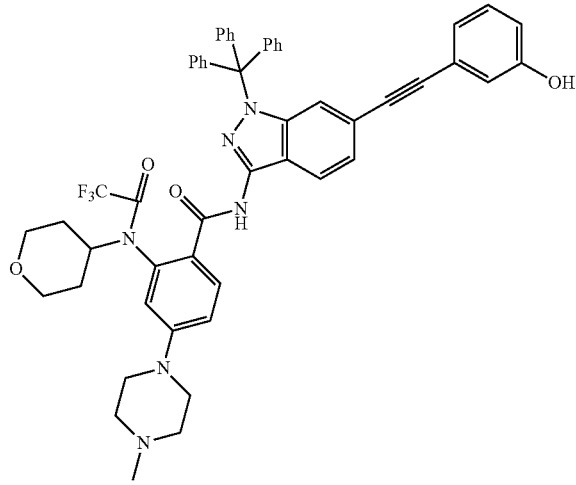 [SMILES: CN1CCN(c2ccc(C(=O)Nc3nn(C(c4ccccc4)(c4ccccc4)c4ccccc4)c4cc(C#Cc5cccc(O)c5)ccc34)c(N(C(=O)C(F)(F)F)C3CCOCC3)c2)CC1]

A microwave vial under argon atmosphere was loaded with N-(6-bromo-1-trityl-1H-indazol-3-yl)-4-(4-methylpiperazin-1-yl)-2-(2,2,2-trifluoro-N-(tetrahydropyran-4-yl)acetamido)benzamide (0.05 mmol, 44 mg), CuI (0.005 mmol, 1 mg), PdCl$_2$(PPh$_3$)$_2$ (0.005 mmol, 4 mg) and PPh$_3$ (0.01 mmol, 3 mg). The mixture was dissolved in a degassed mixture of dioxane/TEA (500 μl dioxane/TEA 5 eq; 0.26 mmol, 36 μl). Finally 3-ethynylphenol was added (0.075 mmol, 9 μl). The reaction was carried out under irradiation at 100° C. for 80 minutes.

The crude was directly purified by flash column chromatography with eluent DCM/MeOH 97:3 affording the title compound (15 mg, 33%).

$^1$H NMR (400 MHz, CDCl$_3$) δ 8.24 (s, 1H), 7.93-7.86 (m, 1H), 7.68 (d, J=8.8 Hz, 1H), 7.32-7.18 (m, 15H), 7.18-7.10 (m, 2H), 6.99 (d, J=7.7 Hz, 1H), 6.87 (dd, J=6.5, 5.2 Hz, 2H), 6.77 (ddd, J=8.2, 2.6, 0.9 Hz, 1H), 6.63 (s, 1H), 6.51 (s, 1H), 4.64 (d, J=11.8 Hz, 1H), 3.98 (d, J=8.1 Hz, 1H), 3.83 (d, J=11.2 Hz, 1H), 3.50 (t, J=11.4 Hz, 1H), 3.42 (t, J=11.6 Hz, 1H), 3.37-3.22 (m, 4H), 2.68-2.47 (m, 4H), 2.38 (s, 3H), 2.09 (d, J=13.5 Hz, 1H), 1.79 (d, J=11.0 Hz, 1H), 1.68 (dd, J=12.1, 4.4 Hz, 1H), 1.31 (dd, J=12.4, 4.6 Hz, 1H).

$^{13}$C NMR (101 MHz, CDCl$_3$) δ 164.0, 155.6, 153.2, 142.5, 142.4, 139.3, 136.9, 135.9, 134.7, 134.6, 131.0, 130.9, 130.2, 129.7, 127.9, 127.6, 124.5, 124.4, 124.3, 123.4, 122.5, 121.1 118.4, 118.1, 117.8, 117.1, 116.0, 114.2, 90.1, 89.2, 78.8, 67.4, 56.1, 54.6, 47.4, 46.2, 31.4, 29.9, 29.6.

(ESI+) MS: m/z 889.5 (MH+).

b) Synthesis of N-[6-[2-(3-hydroxyphenyl)ethynyl]-1H-indazol-3-yl]-4-(4-methylpiperazin-1-yl)-2-(tetrahydropyran-4-ylamino)benzamide [(Ib); R$_2$=R$_5$=H; R$_4$=3-hydrohy-phenyl; R$_6$=4-(4-methylpiperazin-1-yl)-2-(tetrahydropyran-4-ylamino)phenyl]

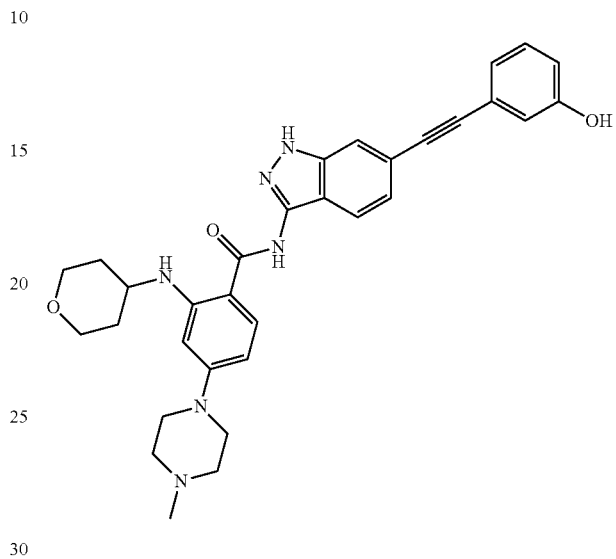

A solution of N-(6-((3-hydroxyphenyl)ethynyl)-1-trityl-1H-indazol-3-yl)-4-(4-methylpiperazin-1-yl)-2-(2,2,2-trifluoro-N-(tetrahydropyran-4-yl)acetamido)benzamide (0.034 mmol, 30 mg) dissolved in 1 ml of a freshly prepared solution of HCl 4M in MeOH, was stirred at 0° C. for 20 hours at room temperature. Solvent was removed and the product was collected as hydrochloride salt. The precipitate was washed with a mixture Et$_2$O/MeOH 95:5 several times affording 18 mg of intermediate that was dissolved in MeOH (600 μl) and TEA (0.2 mmol, 28 μl) at room temperature. The mixture was stirred for 18 hours and the solvent removed under vacuum. The crude was purified by flash column chromatography with eluent DCM/MeOH/NH$_4$OH 9:1:0.1 affording the title compound (16 mg, 85%).

$^1$H NMR (400 MHz, CDCl$_3$) δ 8.58 (s, 1H), 8.15 (d, J=6.6 Hz, 1H), 7.85 (d, J=8.5 Hz, 1H), 7.56 (d, J=9.4 Hz, 2H), 7.24-7.13 (m, 2H), 7.10 (s, 1H), 7.03 (d, J=7.6 Hz, 1H), 6.89 (dd, J=8.1, 1.6 Hz, 1H), 6.19 (d, J=8.9 Hz, 1H), 6.07 (s, 1H), 3.96 (d, J=11.8 Hz, 2H), 3.53 (t, J=10.3 Hz, 3H), 3.31 (s, 4H), 2.59 (d, J=4.5 Hz, 4H), 2.37 (s, 3H), 2.11-1.88 (m, 2H), 1.67-1.53 (m, 2H).

$^{13}$C NMR (101 MHz, CDCl$_3$) δ 167.9, 157.0, 155.1, 151.1, 130.2, 129.6, 124.0, 124.0, 123.3, 118.7, 116.6, 116.0, 113.5, 104.7, 103.1, 96.5, 90.0, 66.6, 54.9, 48.1, 47.6, 33.0, 32.1, 29.8, 29.5, 22.8, 14.3.

(ESI+) MS: m/z 551.5 (MH+).

Example 2 (Method E): Synthesis of 6-[3-[4-[(4-methylpiperazin-1-yl)methyl]-3-(trifluoromethyl) phenoxy]prop-1-ynyl]-1H-indazol-3-amine [(Id); R$_2$=R$_5$=H; R$_4$=[4-[(4-methylpiperazin-1-yl) methyl]-3-(trifluoromethyl)phenoxy]methyl]

a) Synthesis of 4-prop-2-ynoxy-2-(trifluoromethyl)benzaldehyde

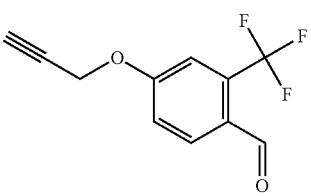 [SMILES: C#CCOc1ccc(C=O)c(C(F)(F)F)c1]

Under nitrogen atmosphere, a solution of 4-fluoro-2-(trifluoromethyl)benzaldehyde (10 mol, 2 g) in CH$_3$CN (10 ml) was added with prop-2-yn-1-ol (30 mmol, 1.7 g) and potassium carbonate (12 mmol, 1.7 g). The mixture was stirred for 5 h at 85° C. The mixture was partitioned between water (50 ml) and CH$_2$Cl$_2$ (50 ml) and the organic phase was dried over sodium sulfate and evaporated to dryness. The residue was purified by flash column chromatography with eluent PE/AcOEt 10:1 to afford the title compound as colorless oil (1.2 g, 53%).

b) Synthesis of 1-methyl-4-[[4-prop-2-ynoxy-2-(trifluoromethyl)phenyl]methyl]piperazine [XXX; R$_4$=[4-[(4-methylpiperazin-1-yl)methyl]-3-(trifluoromethyl)phenoxy]methyl]

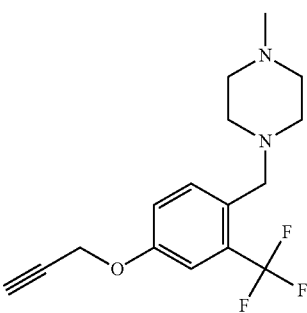 [SMILES: C#CCOc1ccc(CN2CCN(C)CC2)c(C(F)(F)F)c1]

A solution of 4-prop-2-ynoxy-2-(trifluoromethyl)benzaldehyde (1.2 g, 5.3 mmol) in 1,2-dichloroethane (10 ml) was added with 1-methylpiperazine (6.4 mol, 640 mg) followed by TFA (14 mmol, 1.6 g) at room temperature. After 90 minutes of stirring, NaHB(OAc)$_3$ (8 mmol, 0.95 g) was added in one portion and the mixture stirred for 18 h at room temperature and was poured into water and solid K$_2$CO$_3$. The organic layer was evaporated under vacuum. The residue was purified by flash column chromatography with eluent PE/AcOEt 1:1 affording the title compound as yellow solid (0.8 g, 48%).

c) Synthesis of 6-[3-[4-[(4-methylpiperazin-1-yl) methyl]-3-(trifluoromethyl)phenoxy]prop-1-ynyl]-1H-indazol-3-amine [(Id); R$_2$=R$_5$=H; R$_4$=[4-[(4-methylpiperazin-1-yl)methyl]-3-(trifluoromethyl) phenoxy]methyl]

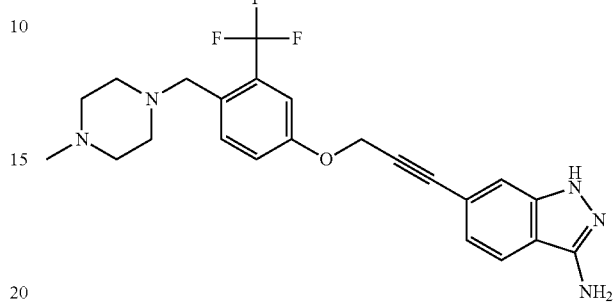

Under nitrogen atmosphere, a solution of 1-methyl-4-[[4-prop-2-ynoxy-2-(trifluoromethyl)phenyl]methyl]piperazine (1.6 mmol, 500 mg) in 1,4-dioxane (15 ml) was added with 6-bromo-1H-indazol-3-amine (2.4 mmol, 500 mg), CuI (0.32 mmol, 60 mg), Pd(PPh$_3$)$_2$Cl$_2$ (0.16 mmol, 112 mg) and TEA (4.8 mmol, 480 mg). The mixture was stirred at 100° C. overnight under nitrogen atmosphere. The mixture was partitioned between water and DCM. The organic phase was washed with water and brine. The resulting solution was dried over sodium sulfate and evaporated to dryness. The residue was purified by flash column chromatography with eluent AcOEt/MeOH 50:1 to afford the title compound as yellow oil (20 mg, 3%).

$^1$H NMR (400 MHz, CD$_3$OD) δ 7.61 (d, J=8.4 Hz, 1H), 7.54 (d, J=7.6 Hz, 1H), 7.24 (m, 2H), 7.19 (m, 1H), 6.89 (d, J=8.4 Hz, 1H), 4.94 (s, 2H), 3.52 (s, 2H), 2.43 (bs, 8H), 2.23 (s, 3H).

(ESI+) MS: m/z 444.2 (MH+).

Example 3 (Method A): synthesis of N-[5-[(3,5-difluorophenyl)methyl]-6-(4-hydroxyphenyl)-1H-indazol-3-yl]-4-(4-methylpiperazin-1-yl)-2-(tetrahydropyran-4-ylamino)benzamide [(Ia); R$_2$=R$_5$=H; R$_4$=4-hydroxy-phenyl; Ar=3,5-difluorophenyl; R$_6$=4-(4-methylpiperazin-1-yl)-2-(tetrahydropyran-4-yl)phenyl]

a) Synthesis of 4-bromo-5-(bromomethyl)-2-fluorobenzonitrile [III; R$_2$=R$_5$=H; Hal=Br]

This compound was previously described in US2010/0261709.

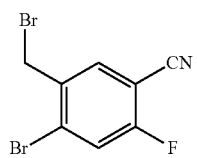 [SMILES: N#Cc1cc(CBr)c(Br)cc1F]

A mixture of 2-fluoro-4-bromo-5-methyl-benzonitrile (2.75 mmol, 590 mg), AIBN (0.28 mmol, 45 mg) and NBS (3.58 mmol, 643 mg) under nitrogen atmosphere was added with CCl$_4$ (18 ml). The reaction was heated at 80° C. and stirred for 20 hours. Reaction was diluted with DCM, washed with NaHSO$_3$ 1M, brine, dried over sodium sulfate, filtered and evaporated to dryness. The crude was purified by flash column chromatography with eluent Hexane/AcOEt 95:5 affording the title compound as a yellow solid (388 mg, 48%).

Intermediate III: $^1$H NMR (400 MHz, CDCl$_3$) δ 7.73 (d, J=6.5 Hz, 1H), 7.52 (d, J=8.1 Hz, 1H), 4.54 (s, 2H).

The purification afforded also 4-bromo-5-(dibromomethyl)-2-fluorobenzonitrile intermediate IV.

Intermediate IV: $^1$H NMR (400 MHz, CDCl$_3$) δ 8.31 (d, J=6.4 Hz, 1H), 7.46 (d, J=7.9 Hz, 1H), 6.95 (s, 1H).

b) Synthesis of 4-bromo-2-fluoro-5-formylbenzonitrile [V; R$_2$=R$_5$=H; Hal=Br]

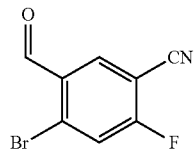

Under nitrogen atmosphere 4-bromo-5-(bromomethyl)-2-fluorobenzonitrile (0.31 mmol, 92 mg) was dissolved in acetonitrile (3 ml) and N-methylmorpholine N-oxide (1.24 mmol, 145 mg) was added slowly. The mixture was stirred for 6 hours at room temperature and evaporated to dryness. The crude was purified by flash column chromatography with eluent Hexane/AcOEt 85:15 affording the title compound as a white solid (49 mg, 70%).

The title compound can be prepared alternatively by reaction of compound IV in dimethylformamide as described in the following procedure.

4-Bromo-5-(dibromomethyl)-2-fluorobenzonitrile (2.68 mmol, 1000 mg) was dissolved in DMF (25 ml) and heated a 130° C. for 8 hours. The reaction mixture was diluted with DCM washed by brine, water, dried over sodium sulfate, filtered and evaporated to dryness affording the title compound (200 mg, 33%).

$^1$H NMR (400 MHz, CDCl$_3$) δ 10.26 (s, 1H), 8.20 (d, J=6.9 Hz, 1H), 7.60 (d, J=8.0 Hz, 1H).

$^{13}$C NMR (101 MHz, CDCl$_3$) δ 188.2, 166.4, 163.7, 135.3, 135.2, 132.9, 132.8, 131.1, 131.0, 122.6, 122.4, 112.2, 102.6, 102.4.

c) Synthesis of 3,5-difluoro-benzene Grignard Reagent [VI; Ar=3,5-difluorophenyl]

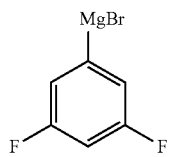

Under nitrogen atmosphere a mixture of Mg (1 mol, 24 g), I$_2$ (trace) and THF (600 ml) was stirred at 60° C. 1-Bromo-3,5-difluorobenzene (0.5 mol, 95 g) in THF (400 ml) was added dropwise keeping the temperature between 50° C. to 60° C. The resulting solution was left to room temperature with stirring and then used directly.

d) Synthesis of 4-bromo-5-[(3,5-difluorophenyl)-hydroxy-methyl]-2-fluorobenzonitrile [VII; R$_2$=R$_5$=H; Hal=Br; Ar=3,5-difluorophenyl]

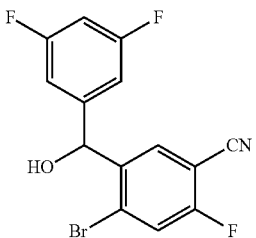 [SMILES: N#Cc1cc(C(O)c2cc(F)cc(F)c2)c(Br)cc1F]

A solution of 4-bromo-2-fluoro-5-formylbenzonitrile under nitrogen atmosphere (0.44 mmol, 101 mg) in dry THF (4 ml) was cooled to −15° C. A solution of 3,5-difluorobenzene Grignard reagent 0.5M in THF (0.48 mmol, 968 μl) was slowly added and the reaction was stirred for 2 hours. The reaction was diluted with a saturated aqueous solution of NH4Cl, diluted with AcOEt, washed with water, dried over sodium sulfate, filtered and evaporated to dryness.

The title compound as a white solid was used without further purification (130 mg, 90%).

$^1$H NMR (400 MHz, CDCl$_3$) δ 7.86 (d, J=6.8 Hz, 1H), 7.47 (d, J=8.1 Hz, 1H), 6.88 (dt, J=8.1, 3.3 Hz, 2H), 6.74 (tt, J=8.8, 2.3 Hz, 1H), 6.07 (s, 1H), 3.30 (bs, 1H).

$^{13}$C NMR (101 MHz, CDCl$_3$) δ 163.2 (dd, J=250.1, 12.6 Hz), 161.7 (d, J=266.5 Hz), 145.0 (t, J=8.4 Hz), 139.8 (d, J=3.8 Hz), 132.9, 128.57 (d, J=9.0 Hz), 121.4 (d, J=22.5 Hz), 113.3, 110.8-109.4 (m), 103.9 (t, J=25.3 Hz), 101.3 (d, J=15.4 Hz), 72.7 (t, J=2.1 Hz).

(ESI+) MS: m/z 340.7 (MH+).

e) Synthesis of 4-bromo-5-(3,5-difluorobenzyl)-2-fluorobenzonitrile [VIII; R$_2$=R$_5$=H; Hal=Br; Ar=3,5-difluorophenyl]

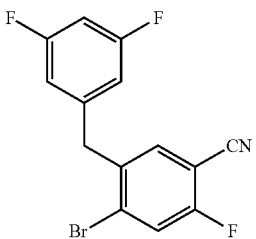 [SMILES: N#Cc1cc(Cc2cc(F)cc(F)c2)c(Br)cc1F]

Compound 4-bromo-5-[(3,5-difluorophenyl)-hydroxymethyl]-2-fluorobenzonitrile (0.386 mmol, 125 mg) was dissolved, under nitrogen atmosphere, in acetonitrile (4 ml). NaI (3.86 mmol, 580 mg) was added slowly. The addition of TMSCl (3.86 mmol, 490 μl) was performed slowly in small portions. The reaction was heated at 70° C. for 8 hours.

The crude was diluted with AcOEt, washed with NaHSO$_3$ 1M, with saturated aqueous solution of NaHCO$_3$, water, dried over sodium sulfate, filtered and evaporated to dryness.

The crude was purified by flash column chromatography with eluent Hex/AcOEt 8:2 affording the title compound as a white solid (25 mg, 20%).

¹H NMR (400 MHz, CDCl₃) δ 7.52 (d, J=8.2 Hz, 1H), 7.36 (d, J=6.6 Hz, 1H), 6.84-6.56 (m, 3H), 4.07 (s, 2H).

¹³C NMR (101 MHz, CDCl₃) δ 163.4 (dd, J=249.1, 12.6 Hz), 161.3 (d, J=262.5 Hz), 141.5 (t, J=9.1 Hz), 136.8 (d, J=3.9 Hz), 134.5, 131.0 (d, J=8.9 Hz), 121.7 (d, J=22.3 Hz), 113.2, 112.4-111.3 (m), 102.8 (t, J=25.2 Hz), 101.2 (d, J=15.3 Hz), 40.6 (t, J=2.0 Hz).

(ESI+) MS: m/z 324.5 (MH+).

f) Synthesis of 5-[(3,5-difluorophenyl)methyl]-2-fluoro-4-[4-[(4-methoxyphenyl)methoxy]phenyl] benzonitrile [X; R₂═R₅═H; R'₄=[4-[(4-methoxyphenyl)methoxy]phenyl]; Ar=3,5-difluorophenyl]

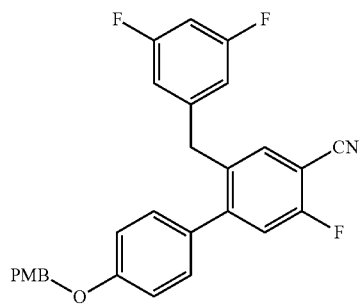

To a microwave vial were added 4-bromo-5-(3,5-difluorobenzyl)-2-fluorobenzonitrile (0.14 mmol, 46 mg), cesium carbonate (0.7 mmol, 228 mg), [4-[(4-methoxyphenyl)methoxy]phenyl] boronic acid (0.154 mmol, 40 mg) and tetrakis(triphenylphosphine)palladium (0.014 mmol, 16 mg). The vial was sealed under Argon atmosphere. A degassed solution of dioxane/water 3:1 was added to the vial (1.5 ml) and the mixture was heated at 100° C. for 90 minutes in a microwave reactor. The crude is diluted with DCM, washed with water, brine, dried over sodium sulfate, filtered and evaporated to dryness.

The crude was purified by flash column chromatography with eluent Hexane/AcOEt 9:1 affording the title compound as a white solid (48 mg, 68%).

¹H NMR (400 MHz, CDCl₃) δ 7.39 (dd, J=13.7, 7.6 Hz, 3H), 7.21-7.05 (m, 3H), 7.00 (d, J=8.8 Hz, 2H), 6.94 (d, J=8.7 Hz, 2H), 6.73-6.55 (m, 1H), 6.42 (d, J=6.0 Hz, 2H), 5.03 (s, 2H), 3.91 (s, 2H), 3.83 (s, 3H).

¹³C NMR (101 MHz, CDCl₃) δ 163.2 (dd, J=251.8, 12.7 Hz), 161.6 (d, J=257.3 Hz), 159.49 (d, J=50.9 Hz). 149.6, 149.5, 143.7, 134.9, 134.5 (d, J=3.9 Hz), 132.0, 129.9, 129.4, 128.6, 118.4 (d, J=19.2 Hz), 115.2, 114.2, 114.0, 112.9-111.0 (m), 102.3 (t, J=25.3 Hz), 70.1, 55.48, 38.0.

(ESI+) MS: m/z 459.6 (MH+).

g) Synthesis of 5-(3,5-difluorobenzyl)-6-(4-((4-methoxybenzyl)oxy)phenyl)-1H-indazol-3-amine [XI; R₂═R₅═H; R'₄=[4-[(4-methoxyphenyl)methoxy]phenyl]; Ar=3,5-difluorophenyl]

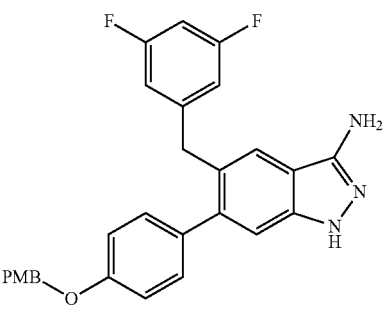

5-[(3,5-Difluorophenyl)methyl]-2-fluoro-4-[4-[(4-methoxyphenyl)methoxy]phenyl]benzonitrile (0.09 mmol, 41 mg) was dissolved in ethanol (1 ml) and hydrazine hydrate 50% (0.47 mmol, 950 µl) was added. The mixture was refluxed for 18 hours. After cooling to room temperature a precipitate was filtered providing the title compound as a white solid (34 mg, 80%).

¹H NMR (400 MHz, CDCl₃) δ 8.91 (s, 1H), 7.48-7.33 (m, 3H), 7.17 (s, 1H), 7.09 (d, J=8.7 Hz, 2H), 7.04-6.87 (m, 4H), 6.64-6.51 (m, 1H), 6.41 (d, J=6.3 Hz, 2H), 5.02 (s, 2H), 4.10 (s, 2H), 3.95 (s, 2H), 3.83 (s, 3H).

¹³C NMR (101 MHz, CDCl₃) δ 159.7, 158.3, 148.7, 142.7-142.0 (m), 142.0-141.3 (m), 134.0, 130.4, 129.4, 129.0, 120.4, 114.4 (d, J=43.7 Hz), 112.0-111.0 (m), 101.4 (t, J=25.3 Hz), 70.1, 55.5, 39.5.

(ESI-) MS: m/z 470.4 (M-H).

h) Synthesis of N-(5-(3,5-difluorobenzyl)-6-(4-((4-methoxybenzyl)oxy)phenyl)-1H-indazol-3-yl)-2,2,2-trifluoroacetamide [XII; R₂═R₅═H; R'₄=[4-[(4-methoxyphenyl)methoxy]phenyl]; Ar=3,5-difluorophenyl; P'=2,2,2-trifluoroacetyl]

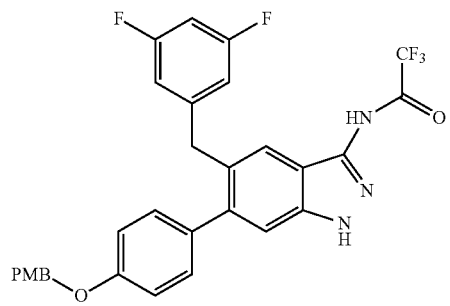

A cooled suspension of 5-(3,5-difluorobenzyl)-6-(4-((4-methoxybenzyl)oxy)phenyl)-1H-indazol-3-amine (0.31 mmol, 146 mg) in DCM (3 ml) under nitrogen atmosphere was slowly added respectively with TEA (0.49 mmol, 70 µl) and TFAA (0.93 mmol, 130 µl). After completion the solvent was removed and residue was dissolved with AcOEt, washed with saturated aqueous solution of NaHCO₃, water, dried over sodium sulfate, filtered and evaporated to dryness. The title compound was isolated as a white solid without further purification (180 mg, 99%).

¹H NMR (400 MHz, CDCl₃) δ 8.99 (s, 1H), 8.32 (s, 1H), 8.16 (s, 1H), 7.41 (d, J=8.7 Hz, 2H), 7.11 (d, J=8.8 Hz, 2H), 7.06-6.90 (m, 4H), 6.68-6.53 (m, 1H), 6.38 (dd, J=8.3, 2.2 Hz, 2H), 5.06 (s, 2H), 4.09 (s, 2H), 3.85 (s, 3H).

¹³C NMR (101 MHz, CDCl₃) δ 163.0 (dd, J=247.6, 12.1 Hz), 159.7, 158.9, 155.6, 147.0, 145.7, 144.4 (t, J=8.1 Hz), 140.6, 136.9, 132.3, 130.2, 129.4, 128.8, 125.6, 118.6, 117.1, 115.0, 114.2, 111.8-111.2 (m), 101.8 (t, J=25.3 Hz), 70.1, 55.5, 39.6.

(ESI−) MS: m/z 566.2 (M−H⁻).

i) Synthesis of N-[5-[(3,5-difluorophenyl)methyl]-6-[4-[(4-methoxyphenyl)methoxy]phenyl]-1-trityl-indazol-3-yl]-2,2,2-trifluoro-acetamide [XIII; R₂=R₅=H; R'₄=[4-[(4-methoxyphenyl)methoxy]phenyl]; Ar=3,5-difluorophenyl; P=Trityl; P'=2,2,2-trifluoroacetyl]

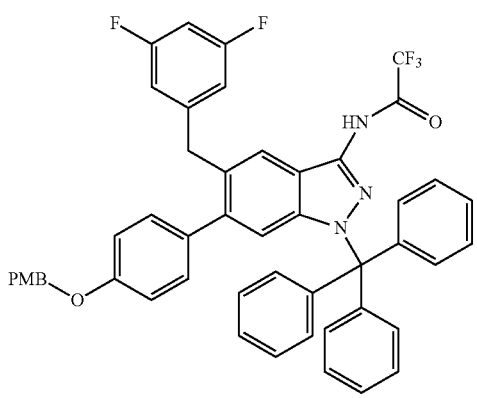

N-(5-(3,5-Difluorobenzyl)-6-(4-((4-methoxybenzyl)oxy)phenyl)-1H-indazol-3-yl)-2,2,2-trifluoroacetamide (0.31 mmol, 180 mg) was dissolved under nitrogen atmosphere in DCM (3 ml). TEA (0.74 mmol, 104 μl) was added followed by trityl chloride (0.37 mmol, 104 mg). Reaction was stirred at room temperature for 72 hours. The mixture was washed with saturated aqueous solution of NH4Cl, water, dried over sodium sulfate, filtered and evaporated to dryness.

The crude was purified by flash column chromatography with eluent DCM/Hex 6:4 affording the title compound as a white solid (162 mg, 65%).

¹H NMR (400 MHz, CDCl₃) δ 9.05 (s, 1H), 7.84 (s, 1H), 7.37 (d, J=8.7 Hz, 2H), 7.32-7.11 (m, 15H), 7.02-6.90 (m, 2H), 6.90-6.78 (m, 2H), 6.78-6.66 (m, 2H), 6.66-6.49 (m, 1H), 6.49-6.34 (m, 2H), 6.30 (s, 1H), 4.98 (s, 2H), 3.96 (s, 2H), 3.84 (s, 3H).

¹³C NMR (101 MHz, CDCl₃) δ 162.9 (dd, J=247.6, 12.9 Hz), 159.6, 158.3, 155.4, 155.1, 154.7, 154.9 (q, J=37.7 Hz), 145.6 (t, J=8.8 Hz), 142.2, 141.9, 141.5, 136.1, 133.6, 131.1, 130.3, 130.3, 129.4, 129.0, 128.1, 127.9, 127.7, 123.8, 117.1, 115.7, 114.3, 114.2, 111.93-110.9 (m), 101.3 (t, J=25.4 Hz), 79.0, 70.0, 55.4, 39.4.

(ESI+) MS m/z: 809.6 (M⁺).

j) Synthesis of 5-[(3,5-difluorophenyl)methyl]-6-[4-[(4-methoxyphenyl)methoxy]phenyl]-1-trityl-indazol-3-amine [XIV; R₂=R₅=H; R'₄=[4-[(4-methoxyphenyl)methoxy]phenyl]; Ar=3,5-difluorophenyl; P=Trityl]

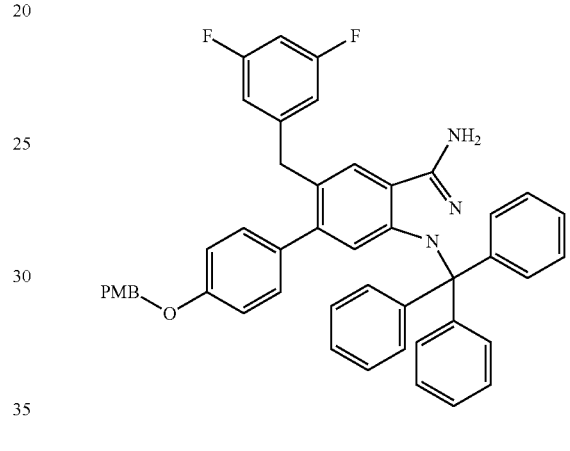

N-[5-[(3,5-difluorophenyl)methyl]-6-[4-[(4-methoxyphenyl)methoxy]phenyl]-1-trityl-indazol-3-yl]-2,2,2-trifluoro-acetamide (0.2 mmol, 162 mg) was dissolved in methanol (2 ml), TEA (0.6 mmol, 83 μl) was added and the mixture was stirred at 70° C. for 18 hours.

Solvent was removed and the crude purified by flash column chromatography with eluent DCM/Hex 97:3 affording the title compound as a white solid (120 mg, 85%).

¹H NMR (400 MHz, CDCl₃) δ 7.46-7.32 (m, 8H), 7.32-7.17 (m, 10H), 7.01-6.92 (m, 2H), 6.92-6.76 (m, 4H), 6.59 (tt, J=9.0, 2.3 Hz, 1H), 6.43 (dd, J=8.5, 2.3 Hz, 2H), 6.22 (s, 1H), 4.99 (s, 2H), 4.05 (s, 2H), 3.88 (s, 2H), 3.85 (s, 3H).

¹³C NMR (101 MHz, CDCl₃) δ 163.0 (dd, J=247.6, 13.0 Hz), 159.6, 158.1, 147.1, 145.8 (t, J=8.8 Hz), 143.3, 142.5, 140.5, 134.2, 130.4, 130.1, 129.4, 129.0, 128.8, 128.1, 127.6, 127.4, 127.1, 120.1, 116.8, 115.7, 114.3, 114.2, 112.1-111.2 (m), 101.3 (t, J=25.5 Hz), 77.7, 70.0, 55.5, 39.2.

(ESI+) MS: m/z 736.6 (MNa⁺).

k) Synthesis of N-[5-[(3,5-difluorophenyl)methyl]-6-[4-[(4-methoxyphenyl)methoxy]phenyl]-1-trityl-indazol-3-yl]-4-(4-methylpiperazin-1-yl)-2-[tetrahydropyran-4-yl-(2,2,2-trifluoroacetyl)amino]benzamide [XVI; $R_2=R_5=H$; $R'_4=[4-[(4-methoxyphenyl)methoxy]phenyl]$; Ar=3,5-difluorophenyl; P=Trityl; $R'_6$=4-(4-methylpiperazin-1-yl)-2-(2,2,2-trifluoro-N-(tetrahydropyran-4-yl)-acetamido)phenyl]

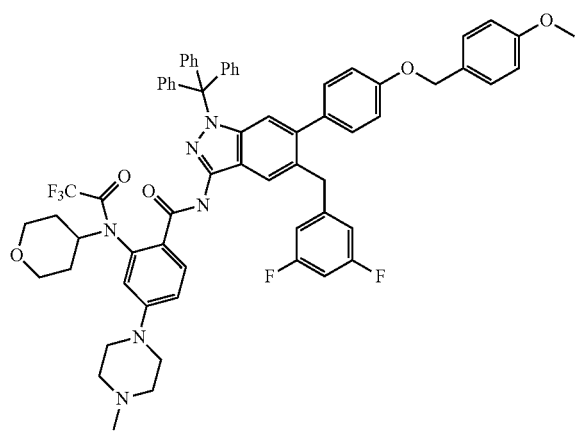 [SMILES: COc1ccc(COc2ccc(-c3cc4c(cc3Cc3cc(F)cc(F)c3)c(NC(=O)c3ccc(N5CCN(C)CC5)cc3N(C(=O)C(F)(F)F)C3CCOCC3)nn4C(c3ccccc3)(c3ccccc3)c3ccccc3)cc2)cc1]

Under nitrogen atmosphere 5-[(3,5-difluorophenyl)methyl]-6-[4-[(4-methoxyphenyl)methoxy]phenyl]-1-trityl-indazol-3-amine (0.11 mmol, 80 mg) was dissolved in THF (400 μl). DMAP (0.011 mmol, 1.5 mg) and DIPEA (0.67 mmol, 117 μl) were added respectively. To the mixture a solution of compound XV (0.11 mmol) dissolved in DCM (400 μl) was added. Reaction was warmed up to 50° C., stirred for 1 hour and quenched with water, diluted with DCM, washed with NaOH 1M, brine, water, dried over sodium sulfate, filtered and evaporated to dryness. The crude was purified by flash column chromatography with eluent DCM/MeOH/NH4OH 96:4:0.1 affording the title compound as a brown solid (50 mg, 40%).

$^1$H NMR (400 MHz, CDCl$_3$) δ 8.44 (s, 1H), 7.69 (d, J=8.8 Hz, 1H), 7.63 (s, 1H), 7.36 (d, J=8.6 Hz, 2H), 7.19 (bs, 15H), 7.03-6.88 (m, 2H), 6.83 (d, J=8.6 Hz, 3H), 6.73 (d, J=8.6 Hz, 2H), 6.62 (d, J=2.0 Hz, 1H), 6.52 (tt, J=9.0, 2.2 Hz, 1H), 6.38 (d, J=6.5 Hz, 2H), 6.24 (s, 1H), 4.96 (s, 2H), 4.65 (ddd, J=12.0, 8.3, 3.6 Hz, 1H), 4.08-3.94 (m, 1H), 3.89 (d, J=16.2 Hz, 2H), 3.82 (s, 3H), 3.75 (d, J=8.1 Hz, 1H), 3.50 (t, J=11.3 Hz, 1H), 3.43-3.21 (m, 5H), 2.68-2.49 (m, 4H), 2.37 (s, 3H), 2.11 (d, J=11.5 Hz, 1H), 1.78-1.57 (m, 2H), 1.33-1.12 (m, 1H).

$^{13}$C NMR (101 MHz, CDCl$_3$) δ 164.2, 162.82 (dd, J=247.4, 12.9 Hz), 159.6, 158.1, 153.0, 145.8 (t, J=9.0 Hz), 142.6, 141.8, 140.8, 138.8, 137.0, 134.0, 130.9, 130.4, 130.2, 129.7, 129.4, 129.0, 127.8, 127.5, 123.8, 122.1, 118.5, 118.0, 117.6, 115.5, 115.1, 114.3, 114.1, 114.1, 112.0-111.1 (m), 101.2 (t, J=25.3 Hz), 78.5, 70.0, 67.3, 56.0, 55.4, 54.6, 47.4, 46.2, 39.4, 31.5, 29.6.

(ESI+) MS: m/z 1111.6 (MH$^+$).

l) Synthesis of N-[5-[(3,5-difluorophenyl)methyl]-6-(4-hydroxyphenyl)-1H-indazol-3-yl]-4-(4-methylpiperazin-1-yl)-2-(tetrahydropyran-4-ylamino)benzamide [(Ia); $R_2=R_5=H$; $R_4$=4-hydroxyphenyl; Ar=3,5-difluorophenyl; $R_6$=4-(4-methylpiperazin-1-yl)-2-(tetrahydropyran-4-ylamino)phenyl]

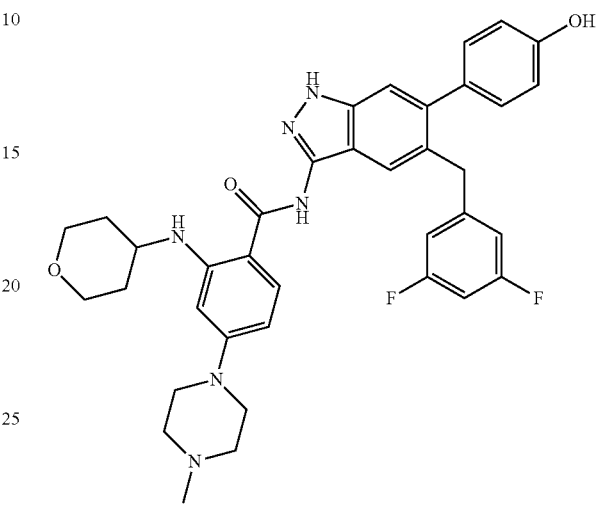

Compound N-[5-[(3,5-difluorophenyl)methyl]-6-[4-[(4-methoxyphenyl)methoxy]phenyl]-1-trityl-indazol-3-yl]-4-(4-methylpiperazin-1-yl)-2-[tetrahydropyran-4-yl-(2,2,2-trifluoroacetyl)amino]benzamide (0.034 mmol, 38 mg) was cooled to 0° C. and dissolved with a DCM/TFA solution 10:1 (1 ml). The mixture was stirred at room temperature for 18 hours. Solvents were evaporated and the crude was purified by flash column chromatography with eluent DCM/MeOH/NH4OH 9:1:0.1 affording N-[5-[(3,5-difluorophenyl)methyl]-6-(4-hydroxyphenyl)-1H-indazol-3-yl]-4-(4-methylpiperazin-1-yl)-2-[tetrahydropyran-4-yl-(2,2,2-trifluoroacetyl)amino]benzamide as a brown solid (10 mg, 40%). This compound was dissolved in MeOH (0.5 ml), TEA (0.04 mmol, 5 μl) was added and the mixture was stirred at room temperature for 18 hours.

Solvent was evaporated and the crude was purified by flash column chromatography with eluent DCM/MeOH/NH4OH 95:5:0.1 affording the title compound as a white solid (4 mg, 47%).

$^1$H NMR (400 MHz, CD$_3$OD) δ $^1$H NMR 7.75 (d, J=8.8 Hz, 1H), 7.65 (s, 1H), 7.25 (s, 1H), 6.98 (d, J=8.4 Hz, 2H), 6.77 (d, J=8.4 Hz, 2H), 6.58-6.62 (m, 1H), 6.40 (d, J=6.8 Hz, 2H), 6.32 (dd, J=9.2 Hz, 2.0 Hz, 1H), 6.22 (d, J=1.6 Hz, 1H), 4.00 (s, 2H), 3.89 (m, 2H), 3.66 (m, 1H), 3.54 (m, 2H), 3.35 (s, 4H), 2.63 (d, J=4.8 Hz, 4H), 2.38 (s, 3H), 2.02 (d, J=10.4 Hz, 2H), 1.48-1.55 (m, 2H).

$^{13}$C NMR (101 MHz, CD$_3$OD) δ 171.1, 165.5, 165.3, 162.9, 157.9, 156.4, 152.1, 147.7, 143.8, 134.0, 131.9, 131.8, 131.5, 129.9, 128.7, 128.0, 123.6, 117.9, 115.8, 112.4 (m), 106.5, 104.4, 101.7 (t, J=25.4 Hz), 98.1, 67.4, 55.9, 46.1, 40.6, 34.1.

(ESI+) MS: m/z 653.7 (MH$^+$).

Example 3 can be alternatively prepared by Method B as follows:

Example 3 (Method B): Synthesis of N-(5-[(3,5-difluorophenyl]methyl]-6-(4-hydroxyphenyl)-1H-indazol-3-yl)-4-(4-methylpiperazin-1-yl)-2-((tetrahydropyran-4-yl)amino)benzamide [(Ia); R$_2$=R$_5$=H; R$_4$=4-hydroxy-phenyl; Ar=3,5-difluorophenyl; R$_{6=4}$-(4-methylpiperazin-1-yl)-2-(tetrahydropyran-4-yl)phenyl]

a) Synthesis of 6-bromo-5[(3,5-difluorophenyl)methyl]-1H-indazol-3-amine [XVIII; R$_2$=R$_5$=H; Hal=Br; Ar=3,5-difluorophenyl]

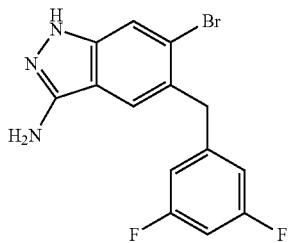

To a solution of intermediate VIII (0.014 mol, 4.6 g) in ethanol (50 ml) was added hydrazine hydrate (0.14 mol, 14 ml). The mixture was refluxed for 18 hours. After cooling to room temperature a precipitate was collected by filtration. The title compound was obtained as a white solid (4.0 g, 97%).

$^1$H NMR (400 MHz, CDCl$_3$) δ 9.09 (s, 1H), 7.60 (s, 1H), 7.33 (s, 1H), 6.63-6.71 (m, 3H), 4.16 (s, 2H), 4.13 (s, 2H).
(ESI+) MS: m/z 339.1 (MH$^+$).

b) Synthesis of N-[6-bromo-5-[(3,5-difluorophenyl)methyl]-1H-indazol-3-yl]-2,2,2-trifluoro-acetamide [XIX; R$_2$=R$_5$=H; Hal=Br; Ar=3,5-difluorophenyl; P'=2,2,2-trifluoroacetyl]

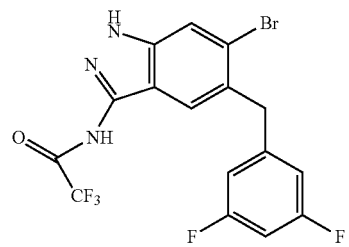

Under nitrogen atmosphere to a solution of 6-bromo-5-[(3,5-difluorophenyl)methyl]-1H-indazol-3-amine (0.19 mol, 72 g) in DCM (500 ml) was added TEA (0.304 mol, 31 g) at 0° C. TFAA (0.228 mol, 48 g) was then added slowly. The mixture was stirred to room temperature for 2 h. When the reaction was complete the solvent was removed and the residue was dissolved with AcOEt. The solution was washed with saturated NaHCO$_3$ solution and water. The organic phase was dried over sodium sulfate and evaporated to dryness. The title compound without further purification was obtained as a white solid (3.7 g, 87%).

$^1$H NMR (400 MHz, MeOD) δ 7.83 (s, 1H), 7.78 (s, 1H), 6.74-6.86 (m, 3H), 4.25 (s, 2H).
(ESI+) MS: m/z 435.0 (MH$^+$).

c) Synthesis of N-[6-bromo-5-[(3,5-difluorophenyl)methyl]-1-trityl-indazol-3-yl]-2,2,2-trifluoro-acetamide [XX; R$_2$=R$_5$=H; Hal=Br; Ar=3,5-difluorophenyl; P'=2,2,2-trifluoroacetyl; P=Trityl]

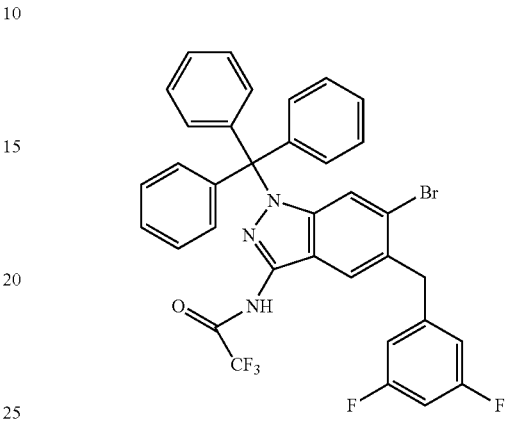

Under nitrogen atmosphere to a solution of N-[6-bromo-5-[(3,5-difluorophenyl)methyl]-1H-indazol-3-yl]-2,2,2-trifluoro-acetamide (8.5 mmol, 3.7 g) in DCM (20 ml) was added TEA (17 mmol, 1.8 g). Trityl chloride (13 mmol, 3.6 g) was added dropwise. The mixture was stirred at room temperature for 2 hours. When the reaction was completed, the mixture was washed with saturated NH$_4$Cl solution and water. The organic phase was dried over sodium sulfate and evaporated to dryness. The residue was purified by flash column chromatography with eluent Hex/AcOEt 5:1 to afford the title compound as a white solid (3.6 g, 63%).

$^1$H NMR (400 MHz, CDCl$_3$) δ 8.85 (s, 1H), 7.91 (s, 1H), 7.16-7.33 (m, 15H), 6.59-6.68 (m, 3H), 4.09 (s, 2H).

d) Synthesis of 6-bromo-5-[(3,5-difluorophenyl)methyl]-1-trityl-indazol-3-amine [XXI; R$_2$=R$_5$=H; Hal=Br; Ar=3,5-difluorophenyl; P=Trityl]

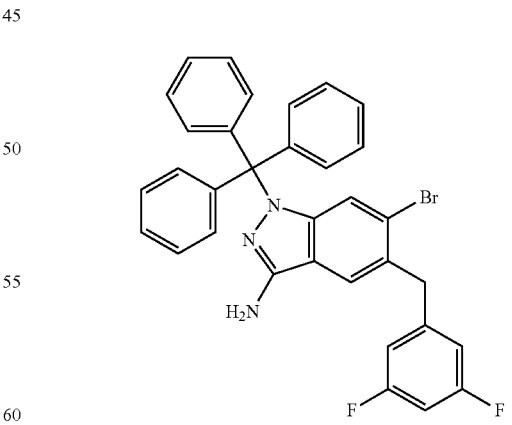

To a solution of N-[6-bromo-5-[(3,5-difluorophenyl)methyl]-1-trityl-indazol-3-yl]-2,2,2-trifluoro-acetamide (5.3 mmol, 3.6 g) in methanol (10 ml) was added TEA (1.6 mmol, 1.6 g). The mixture was stirred at 70° C. for 18 h. The solvent was removed and the residue was purified by flash column chromatography (Hex/AcOEt 3:1) to afford the title compound as a white solid (2.8 g, 92%).

$^{1}$H NMR (400 MHz, DMSO-d$_{6}$) δ 7.25-7.33 (m, 15H), 7.15 (s, 1H), 6.64-7.67 (m, 3H), 6.45 (s, 1H), 4.04 (s, 2H), 4.00 (s, 2H).

e) Synthesis of N-[6-bromo-5-[(3,5-difluorophenyl)methyl]-1-trityl-indazol-3-yl]-4-(4-methylpiperazin-1-yl)-2-[tetrahydropyran-4-yl-(2,2,2-trifluoroacetyl)amino]benzamide [XXII; R$_{2}$=R$_{5}$=H; Hal=Br; Ar=3,5-difluorophenyl; P=Trityl; R'$_{6}$=4-(4-methyl-piperazin-1-yl)-2-(2,2,2-trifluoro-N-(tetrahydropyran-4-yl)-acetamido)phenyl]

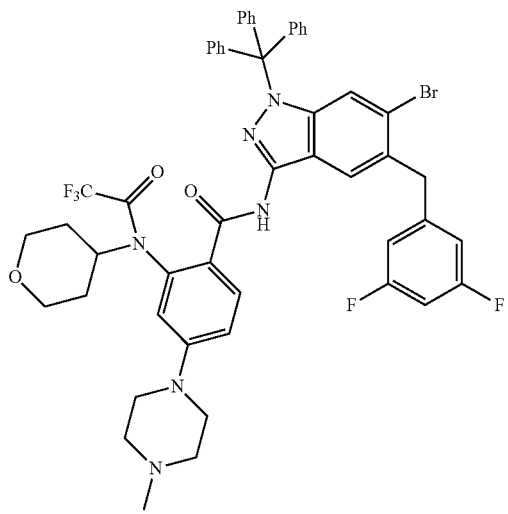 [SMILES: CN1CCN(c2ccc(C(=O)Nc3nn(C(c4ccccc4)(c4ccccc4)c4ccccc4)c4cc(Br)c(Cc5cc(F)cc(F)c5)cc34)c(N(C(=O)C(F)(F)F)C3CCOCC3)c2)CC1]

To a solution of 6-bromo-5-[(3,5-difluorophenyl)methyl]-1-trityl-indazol-3-amine under nitrogen atmosphere (4.8 mmol, 2.8 g) in dry THF (20 ml) was added DMAP (0.48 mmol, 60 mg) and DIPEA (29 mmol, 3.7 g). Intermediate 4-(4-methylpiperazin-4-ium-1-yl)-2-[tetrahydropyran-4-yl-(2,2,2-trifluoroacetyl)amino]benzoyl chloride (2 eq.) was added in portions. The resulting mixture was immediately warmed up to 50° C. and stirred for 1 h. After the reaction was completed, the mixture was partitioned between water and DCM. The organic phase was washed by NaOH solution (1M), brine and water. The resulting solution was dried over sodium sulfate and evaporated to dryness. The residue was purified by flash column chromatography with eluent AcOEt/MeOH 20:1 to afford the title compound as a white solid (2.6 g, 62%).

$^{1}$H NMR (400 MHz, CDCl$_{3}$) δ 8.21 (s, 1H), 7.79 (s, 1H), 7.67 (d, J=8.8 Hz, 1H), 7.28-7.30 (m, 9H), 7.20-7.24 (m, 6H), 6.89 (dd, J=10.8 Hz, 2.4 Hz, 1H), 6.74 (d, J=6.4 Hz, 2H), 6.60-6.64 (m, 1H), 6.52 (s, 1H), 4.60-4.67 (m, 1H), 4.08 (s, 2H), 3.95-3.99 (m, 1H), 3.79-3.83 (m, 1H), 3.48-3.53 (m, 1H), 3.39-3.42 (m, 1H), 3.34 (t, J=5.2 Hz, 4H), 2.59 (t, J=4.8 Hz, 4H), 2.38 (s, 3H), 1.65-1.76 (m, 2H), 1.24-1.31 (m, 2H).

f) Synthesis of N-[5-[(3,5-difluorophenyl)methyl]-6-(4-hydroxyphenyl)-1-trityl-indazol-3-yl]-4-(4-methylpiperazin-1-yl)-2-(tetrahydropyran-4-ylamino)benzamide [XXIII; R$_{2}$=R$_{5}$=H; Ar=3,5-difluorophenyl; P=Trityl; R$_{4}$=4-hydroxy-phenyl; R$_{6}$=4-(4-methylpiperazin-1-yl)-2-(tetrahydropyran-4-ylamino)phenyl]

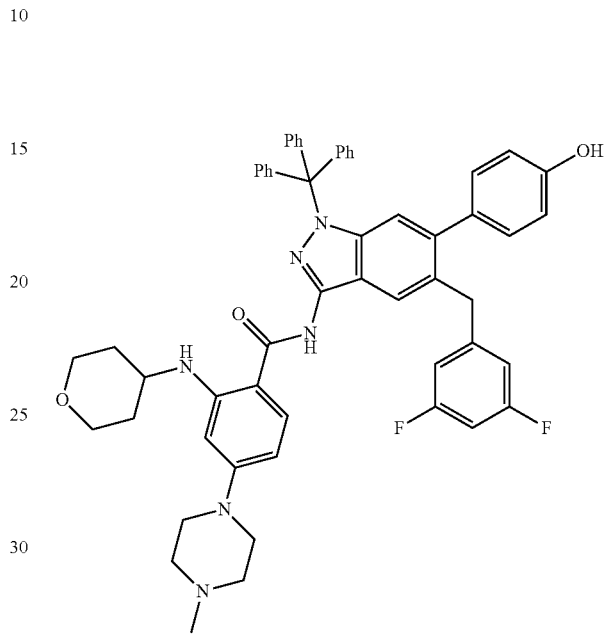

To a round bottom flask under nitrogen atmosphere was added N-[6-bromo-5-[(3,5-difluorophenyl)methyl]-1-trityl-indazol-3-yl]-4-(4-methylpiperazin-1-yl)-2-[tetrahydropyran-4-yl-(2,2,2-trifluoroacetyl)amino]benzamide (2.7 mmol, 2.6 g), cesium carbonate (13.5 mmol, 4.4 g), 4-hydroxyphenyl boronic acid (5.4 mmol, 0.75 g) and Pd(PPh$_{3}$)$_{4}$ (0.27 mmol, 312 mg). In another flask was prepared a degassed solution of dioxane/water 3:1 which was then added to the above flask (16 ml) and stirred over 5 minutes in order to dissolve the suspension. The mixture was stirred at 100° C. overnight. The mixture was partitioned between water and DCM. The organic phase was washed with water and brine. The resulting solution was dried over sodium sulfate and evaporated to dryness. The residue was purified by flash column chromatography with eluent AcOEt/MeOH 30:1 to afford the title compound as a white solid (1.8 g, 75%).

$^{1}$H NMR (400 MHz, CDCl$_{3}$) δ 8.27 (s, 1H), 8.15 (d, J=7.2 Hz, 1H), 7.74 (s, 1H), 7.48 (d, J=8.8 Hz, 1H), 7.24 (s, 15H), 6.64 (s, 4H), 6.47-6.53 (m, 1H), 6.35-6.38 (m, 2H), 6.18-6.21 (m, 2H), 6.08 (s, 1H), 4.98-4.03 (m, 2H), 3.88 (s, 2H), 3.52-3.58 (m, 3H), 3.32 (t, J=4.8 Hz, 4H), 2.59 (t, J=4.8 Hz, 4H), 2.37 (s, 3H), 1.58-1.68 (m, 2H), 1.24-1.28 (m, 2H).

g) Synthesis of N-(5-[(3,5-difluorophenyl)methyl)-6-(4-hydroxyphenyl)-1H-indazol-3-yl)-4-(4-methyl-piperazin-1-yl)-2-((tetrahydropyran-4-yl)amino)benzamide [(Ia); R$_2$=R$_5$=H; R$_4$=4-hydroxyphenyl; Ar=3,5-difluorophenyl; R$_6$=4-(4-methylpiperazin-1-yl)-2-(tetrahydropyran-4-ylamino)phenyl]

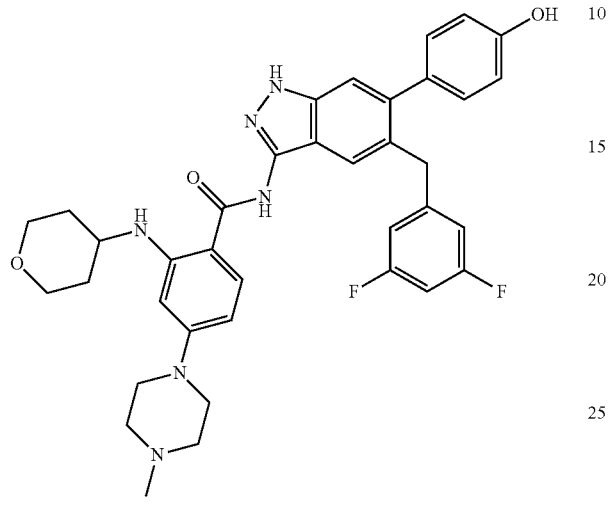

N-[5-[(3,5-difluorophenyl)methyl]-6-(4-hydroxyphenyl)-1-trityl-indazol-3-yl]-4-(4-methylpiperazin-1-yl)-2-(tetrahydropyran-4-ylamino)benzamide (5.9 mmol, 5.3 g) was dissolved in a HO/MeOH solution (5M, 10 ml) at 0° C. The mixture was stirred at room temperature for 3 h. After the reaction is complete the mixture was partitioned between water and DCM. The organic phase was washed with NaHCO3 solution (1M), brine and water. The resulting solution was dried over sodium sulfate and evaporated to dryness. The residue was purified by flash column chromatography with eluent AcOEt/MeOH 10:1 to afford the title compound as a yellow solid (2.6 g, 68%).

Examples from compound 4 to compound 31 having formula (Ia) were prepared by Method B via Suzuki coupling on intermediate XXII N-[6-bromo-5-[(3,5-difluorophenyl)methyl]-1-trityl-indazol-3-yl]-4-(4-methylpiperazin-1-yl)-2-[tetrahydropyran-4-yl-(2,2,2-trifluoroacetyl)amino]benzamide and final removal of protective group P on intermediate XXIII in agreement with the following General procedures:

General procedure for Suzuki coupling on intermediate XXII: in a microwave vial containing intermediate XXII (1 eq.), corresponding boronic acid (2 eq.), Cs$_2$CO$_3$ (5 eq.) and dioxane/water (3:1, 2.5 ml), was added Pd(PPh3)4 (0.05 eq.) under argon atmosphere. The mixture was heated to 100° C. under microwave irradiation and stirred for 90 minutes. The solvent was removed and the residue was purified by flash column chromatography with a gradient eluent from DCM/MeOH 100:1 to 40:1 affording compounds of general formula XXIII.

General procedure for removal of protective group P from intermediate XXIII: in a round bottom flask containing intermediate XXIII (1 eq.) in 2 ml of methanol HO/MeOH (5M, 1.0 ml). The mixture was stirred at room temperature for 30 minutes. The solvent was removed and the residue was purified by preparative HPLC to afford the title compound.

Example 4 (Method B): synthesis of N-[5-[(3,5-difluorophenyl)methyl]-6-(3-hydroxyphenyl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=3-hydroxyphenyl; R$_{6=4}$-(4-methylpiperazin-1-yl)-2-(tetrahydropyran-4-ylamino)phenyl]

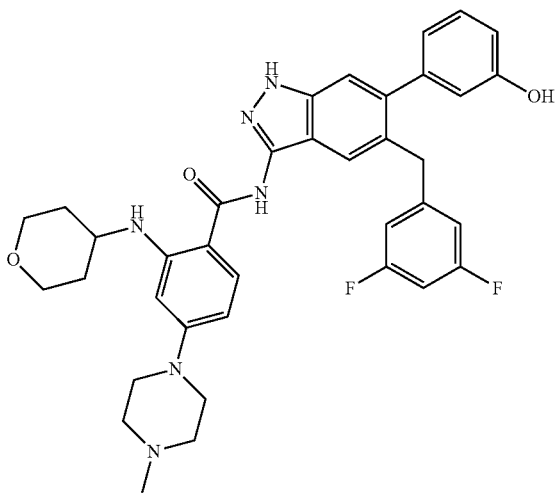 [SMILES: CN1CCN(c2ccc(C(=O)Nc3n[nH]c4cc(-c5cccc(O)c5)c(Cc5cc(F)cc(F)c5)cc34)c(NC3CCOCC3)c2)CC1]

$^1$H NMR (400 MHz, CD$_3$OD) δ 7.75 (d, J=8.8 Hz, 1H), 7.66 (s, 1H), 7.26 (s, 1H), 7.16 (t, J=8.4 Hz, 1H), 6.77 (dd, J=8.4 Hz, 2.1 Hz, 1H), 6.64 (m, 3H), 6.41 (d, J=6.8 Hz, 2H), 6.34 (dd, J=8.4 Hz, 2.1 Hz, 1H), 6.22 (m, 1H), 4.02 (s, 2H), 3.94 (m, 2H), 3.61 (m, 1H), 3.58 (td, J=11 Hz, 2.4 Hz, 2H), 3.30 (s, 4H), 2.65 (d, J=4.7 Hz, 4H), 2.39 (s, 3H), 2.05 (m, 2H), 1.53 (m, 2H).

(ESI+) MS: m/z 653.3 (MH$^{-1}$).

Example 5 (Method B): synthesis of N-[5-[(3,5-difluorophenyl)methyl]-6-(4-hydroxy-2-methyl-phenyl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=4-hydroxy-2-methyl-phenyl; R$_6$=4-(4-methylpiperazin-1-yl)-2-(tetrahydropyran-4-ylamino)phenyl]

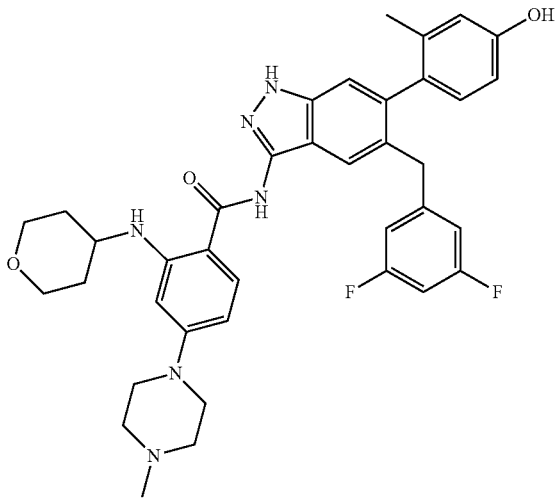 [SMILES: Cc1cc(O)ccc1-c1cc2[nH]nc(NC(=O)c3ccc(N4CCN(C)CC4)cc3NC3CCOCC3)c2cc1Cc1cc(F)cc(F)c1]

$^{1}$H NMR (400 MHz, DMSO-d$_6$) δ 12.60 (s, 1H), 10.17 (s, 1H), 9.36 (s, 1H), 8.34 (d, J=8.2 Hz, 1H), 7.80 (d, J=8.4 Hz, 1H), 7.57 (s, 1H), 7.09 (s, 1H), 6.91 (m, 1H), 6.65 (d, J=8.4 Hz, 1H), 6.41 (m, 1H), 6.39 (dd, J=8.4 Hz, 2.3 Hz, 2H), 6.26 (dd, J=8.2 Hz, 2.2 Hz, 1H), 6.13 (m, 1H), 3.86 (m, 3H), 3.71 (m, 2H), 3.49 (td, J=11 Hz, 2.1 Hz, 2H), 3.37 (s, 2H), 3.34 (m, 4H), 3.26 (m, 4H), 2.43 (s, 3H), 1.95 (m, 2H), 1.75 (s, 3H).

(ESI+) MS: m/z 667.3 (MH$^{-1}$).

Example 6 (Method B): synthesis of N-[5-[(3,5-difluorophenyl)methyl]-6-(2-fluoro-4-hydroxy-phenyl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=4-hydroxy-2-fluoro-phenyl; R$_6$=4-(4-methylpiperazin-1-yl)-2-(tetrahydropyran-4-ylamino)phenyl]

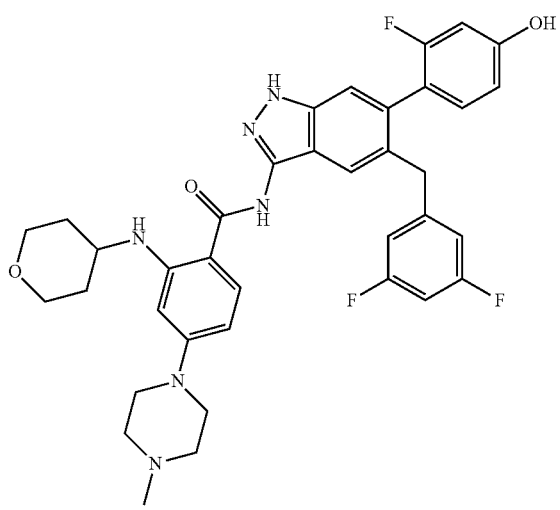 [SMILES: CN1CCN(c2ccc(C(=O)Nc3n[nH]c4cc(-c5ccc(O)cc5F)c(Cc5cc(F)cc(F)c5)cc34)c(NC3CCOCC3)c2)CC1]

$^{1}$H NMR (400 MHz, DMSO-d$_6$) δ 12.69 (s, 1H), 10.18 (s, 1H), 9.98 (s, 1H), 8.33 (s, J=8.3 Hz, 1H), 7.82 (s, J=8.4 Hz, 1H), 7.57 (s, 1H), 7.21 (s, 1H), 6.98 (t, J=8.2 Hz, 1H), 6.93 (t, J=8.2 Hz, 1H), 6.64 (m, 2H), 6.44 (d, J=8.2 Hz, 2H), 6.23 (dd, J=8.4 Hz, 2.1 Hz, 1H), 6.13 (m, 1H), 3.89 (m, 2H), 3.83 (m, 2H), 3.79 (m, 1H), 3.51 (m, 2H), 3.38 (m, 4H), 2.67 (m, 4H), 2.17 (s, 3H), 1.88 (m, 2H), 1.33 (2H).

(ESI+) MS: m/z 671.3 (MH$^{-1}$).

Example 7 (Method B): synthesis of N-[5-[(3,5-difluorophenyl)methyl]-6-(5-hydroxy-2-methyl-phenyl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=2-methyl-5-hydroxy-phenyl; R$_6$=4-(4-methylpiperazin-1-yl)-2-(tetrahydropyran-4-ylamino)phenyl]

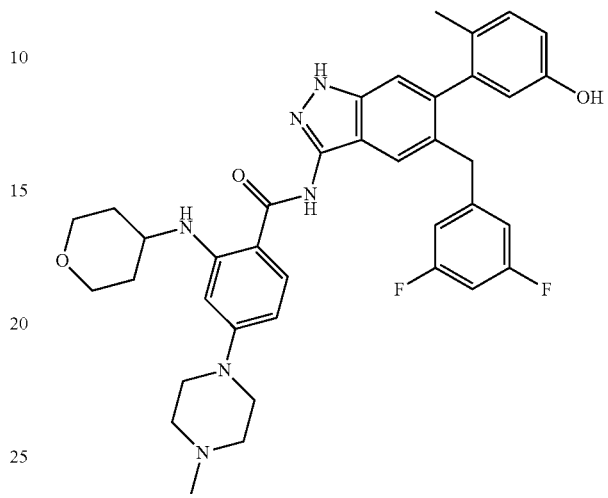

$^{1}$H NMR (400 MHz, DMSO-d$_6$) δ 12.64 (s, 1H), 10.18 (s, 1H), 9.24 (s, 1H), 8.34 (d, J=8.4 Hz, 1H), 7.82 (d, J=8.7 Hz, 1H), 7.58 (s, 1H), 7.11 (s, 1H), 7.05 (d, J=8.7 Hz, 1H), 6.92 (m, 1H), 6.71 (dd, J=8.4 Hz, 2.4 Hz, 1H), 6.44 (m, 3H), 6.23 (dd, J=8.4 Hz, 2.4 Hz, 1H), 6.13 (s, 1H), 3.80 (m, 3H), 3.71 (m, 2H), 3.51 (m, 2H), 3.33 (m, 4H), 2.44 (m, 4H), 2.23 (s, 3H), 1.95 (m, 2H), 1.72 (s, 3H), 1.35 (m, 2H).

(ESI+) MS: m/z 667.3 (MH$^{-1}$).

Example 8 (Method B): synthesis of N-[5-[(3,5-difluorophenyl)methyl]-6-(2-fluoro-5-hydroxy-phenyl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=2-fluoro-5-hydroxy-phenyl; R$_6$=4-(4-methylpiperazin-1-yl)-2-(tetrahydropyran-4-ylamino)phenyl]

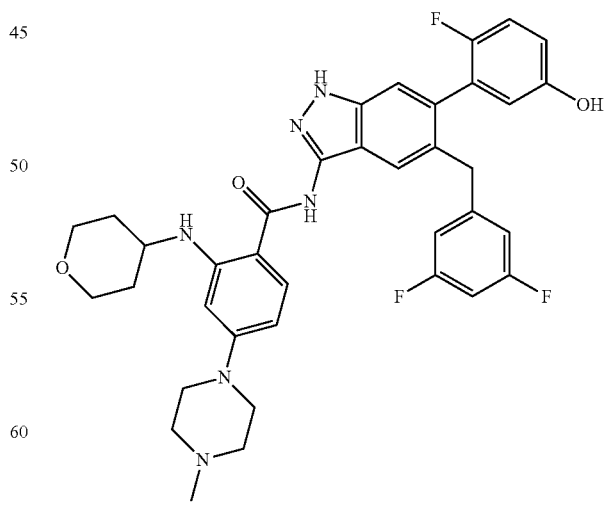

$^{1}$H NMR (400 MHz, CD$_3$OD) δ 7.77 (d, J=9.2 Hz, 1H), 7.69 (s, 1H), 7.28 (s, 1H), 6.96 (t, J=9.2 Hz, 1H), 6.76 (m, 1H), 6.61 (m, 1H), 6.47 (m, 1H), 6.50 (dd, J=8.1 Hz, 1.9 Hz, 1H), 6.37 (m, 2H), 6.13 (s, 1H), 3.93 (m, 4H), 3.71 (m, 1H), 3.61 (td, J=8.1 Hz, 1.9 Hz, 2H), 3.34 (m, 4H), 2.61 (m, 4H), 2.36 (s, 3H), 2.04 (m, 2H), 1.52 (m, 2H).

(ESI+) MS: m/z 671.3 (MH⁻¹).

Example 9 (Method B): synthesis of N-[5-[(3,5-difluorophenyl)methyl]-6-[4-hydroxy-2-(trifluoromethyl)phenyl]-1H-indazol-3-yl]-4-(4-methylpiperazin-1-yl)-2-(tetrahydropyran-4-ylamino)benzamide [(Ia); R₂=R₅=H; Ar=3,5-difluorophenyl; R₄=4-hydroxy-2-trifluoromethyl-phenyl; R₆=4-(4-methylpiperazin-1-yl)-2-(tetrahydropyran-4-ylamino)phenyl]

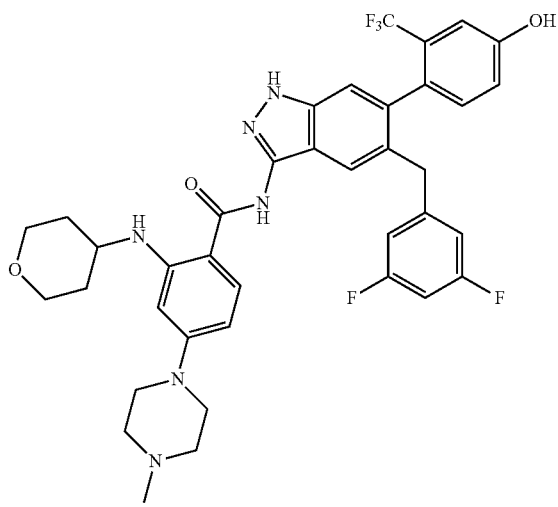 [SMILES: CN1CCN(c2ccc(C(=O)Nc3n[nH]c4cc(-c5ccc(O)cc5C(F)(F)F)c(Cc5cc(F)cc(F)c5)cc34)c(NC3CCOCC3)c2)CC1]

¹H NMR (400 MHz, DMSO-d₆) δ 12.66 (s, 1H), 10.20 (d, J=8.5 Hz, 2H), 8.33 (d, J=8.5 Hz, 1H), 7.82 (d, J=8.3 Hz, 1H), 7.52 (s, 1H), 7.16 (d, J=8.3 Hz, 2H), 7.01 (s, 2H), 6.94 (m, 1H), 6.48 (d, J=8.3 Hz, 2H), 6.25 (d, J=8.5 Hz, 1H), 6.13 (s, 1H), 3.84 (m, 3H), 3.68 (m, 2H), 3.48 (td, J=9.7 Hz, 2.3 Hz, 2H), 3.29 (m, 4H), 2.44 (m, 4H), 2.22 (s, 3H), 1.91 (m, 2H), 1.35 (m, 2H).

(ESI+) MS: m/z 721.3 (MH⁻¹).

Example 10 (Method B): synthesis of N-[6-(2-aminopyrimidin-5-yl)-5-[(3,5-difluorophenyl)methyl]-1H-indazol-3-yl]-4-(4-methylpiperazin-1-yl)-2-(tetrahydropyran-4-ylamino)benzamide [(Ia); R₂=R₅=H; Ar=3,5-difluorophenyl; R₄=6-(2-aminopyrimidin-5-yl); R₆=4-(4-methylpiperazin-1-yl)-2-(tetrahydropyran-4-ylamino)phenyl]

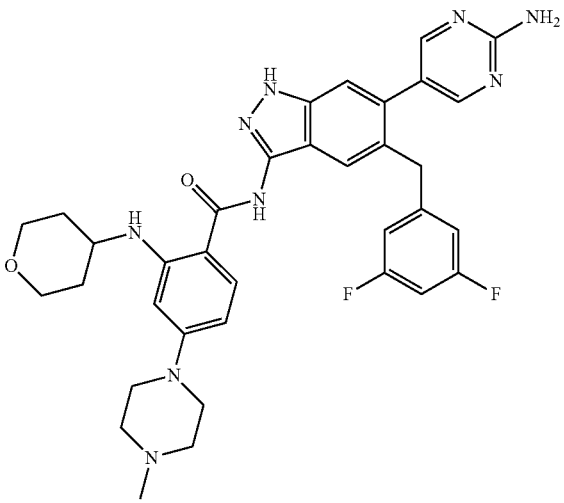 [SMILES: CN1CCN(c2ccc(C(=O)Nc3n[nH]c4cc(-c5cnc(N)nc5)c(Cc5cc(F)cc(F)c5)cc34)c(NC3CCOCC3)c2)CC1]

¹H NMR (400 MHz, DMSO-d₆) δ 12.73 (s, 1H), 10.19 (s, 1H), 8.33 (s, J=8.5 Hz, 1H), 8.08 (s, 2H), 7.82 (d, J=8.3 Hz, 1H), 7.55 (s, 1H), 7.27 (s, 1H), 6.94 (m, 1H), 6.72 (s, 2H), 6.57 (dd, J=8.3 Hz, 2H), 6.24 (dd, J=8.5 Hz, 1H), 6.12 (s, 1H), 4.03 (s, 2H), 3.82 (m, 2H), 3.67 (m, 1H), 3.48 (td, J=10.2 Hz, 2.4 Hz, 2H), 3.33 (m, 4H), 2.38 (m, 4H), 2.22 (s, 3H), 1.94 (m, 2H), 1.32 (m, 2H).

(ESI+) MS: m/z 654.3 (MH⁻¹).

Example 11 (Method B): synthesis of N-[6-(6-amino-3-pyridyl)-5-[(3,5-difluorophenyl)methyl]-1H-indazol-3-yl]-4-(4-methylpiperazin-1-yl)-2-(tetrahydropyran-4-ylamino)benzamide [(Ia); R₂=R₅=H; Ar=3,5-difluorophenyl; R₄=6-(6-amino-3-pyridyl); R₆=4-(4-methylpiperazin-1-yl)-2-(tetrahydropyran-4-ylamino)phenyl]

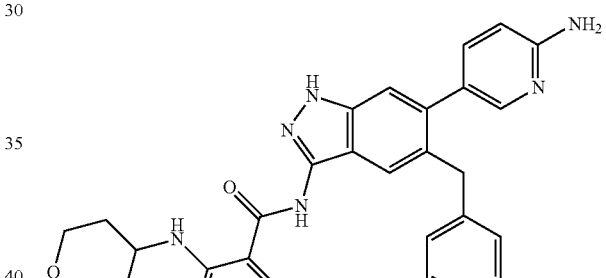

¹H NMR (400 MHz, CD₃OD) δ 7.74 (d, J=8.8 Hz, 1H), 7.67 (s, 1H), 7.61 (d, J=2 Hz, 1H), 7.27 (m, 2H), 6.58 (m, 2H), 6.44 (d, J=8.8 Hz, 2H), 6.32 (d, J=9.2 Hz, 1H), 6.20 (s, 1H), 4.03 (m, 2H), 3.92 (m, 2H); 3.67 (m, 1H), 3.56 (t, J=11 Hz, 2H), 3.32 (m, 4H), 2.58 (m, 4H), 2.33 (s, 3H), 2.02 (m, 2H), 1.51 (m, 2H).

(ESI+) MS: m/z 653.3 (MH⁺).

Example 12 (Method B): synthesis of N-[6-(5-amino-3-pyridyl)-5-[(3,5-difluorophenyl)methyl]-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=6-(5-amino-3-pyridyl); R$_6$=4-(4-methylpiperazin-1-yl)-2-(tetrahydropyran-4-ylamino)phenyl]

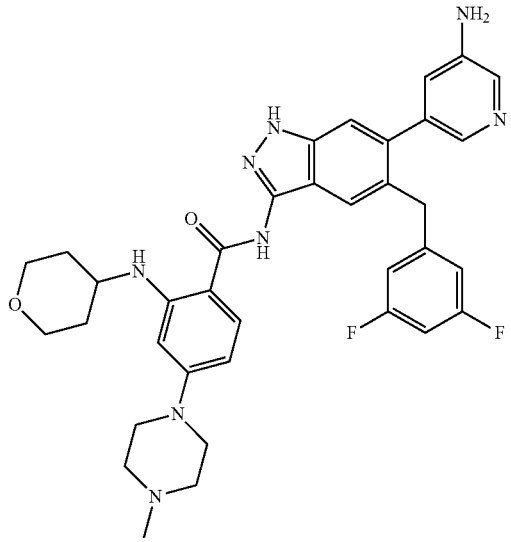 [SMILES: CN1CCN(c2ccc(C(=O)Nc3n[nH]c4cc(-c5cncc(N)c5)c(Cc5cc(F)cc(F)c5)cc34)c(NC3CCOCC3)c2)CC1]

$^1$H NMR (400 MHz, CD$_3$OD) δ 7.91 (d, J=2 Hz, 1H), 7.76 (d, J=8.8 Hz, 1H), 7.71 (s, 1H), 7.50 (s, 1H), 7.28 (s, 1H), 6.91 (d, J=2 Hz, 1H), 6.60 (m, 1H), 6.40 (m, 2H), 6.32 (d, J=8.8 Hz, 1H), 6.21 (s, 1H), 4.02 (m, 2H), 3.91 (m, 2H), 3.68 (m, 1H), 3.59 (td, J=11 Hz, 2.4 Hz, 2H), 3.53 (m, 4H), 2.58 (m, 4H), 2.34 (s, 3H), 2.02 (m, 2H), 1.49 (m, 2H).
(ESI+) MS: m/z 653.4 (MH$^{-1}$).

Example 13 (Method B): synthesis of N-[5-[(3,5-difluorophenyl)methyl]-6-[3-(hydroxymethyl)phenyl]-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=3-hydroxymethyl-phenyl; R$_6$=4-(4-methylpiperazin-1-yl)-2-(tetrahydropyran-4-ylamino)phenyl]

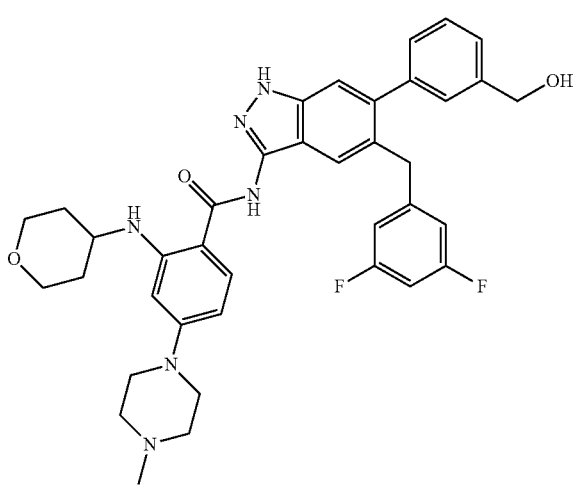 [SMILES: CN1CCN(c2ccc(C(=O)Nc3n[nH]c4cc(-c5cccc(CO)c5)c(Cc5cc(F)cc(F)c5)cc34)c(NC3CCOCC3)c2)CC1]

$^1$H NMR (400 MHz, CD$_3$OD) δ 7.68 (d, J=8.8 Hz, 1H), 7.59 (s, 1H), 7.25 (m, 2H), 7.24 (s, 1H), 7.07 (bs, 1H), 6.98 (m, 1H), 6.51 (tt, 1H), 6.31 (m, 2H), 6.25 (dd, J=8.8 Hz, 2.4 Hz, 1H), 6.13 (bs, 1H), 4.50 (s, 2H), 3.92 (s, 2H), 3.85 (dt, 2H), 3.61 (m, 1H), 3.47 (td, J=12 Hz, 2.4 Hz, 2H), 3.25 (m, 4H), 2.51 (m, 4H), 2.26 (s, 3H), 1.95 (m, 2H), 1.44 (m, 2H).

(ESI+) MS: m/z 667.3 (MH$^{-1}$).

Example 14 (Method B): synthesis of N-[6-(6-amino-4-methyl-3-pyridyl)-5-[(3,5-difluorophenyl)methyl]-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=6-(6-amino-4-methyl-3-pyridyl); R$_6$=4-(4-methylpiperazin-1-yl)-2-(tetrahydropyran-4-ylamino)phenyl]

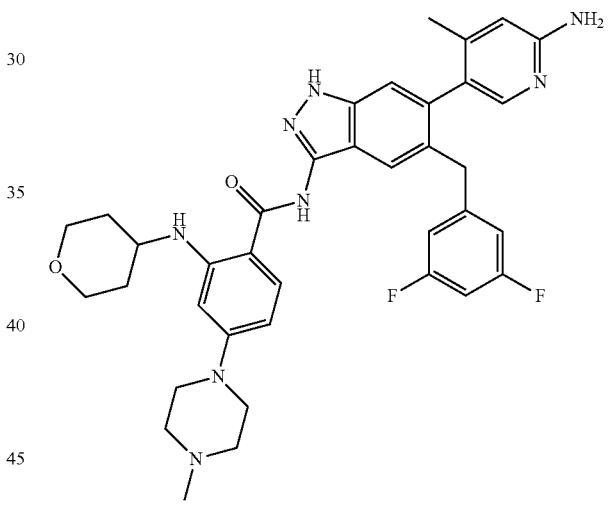

$^1$H NMR (400 MHz, DMSO-d$_6$) δ 12.64 (s, 1H), 10.17 (s, 1H); 8.33 (d, J=7.6 Hz, 1H), 7.82 (d, J=9.2 Hz, 1H), 7.57 (s, 1H), 7.49 (s, 1H), 7.13 (s, 1H), 6.95 (t, J=8.8 Hz, 1H), 6.47 (d, J=7.6 Hz, 2H), 6.32 (s, 1H), 6.25 (d, J=9.2 Hz, 1H), 6.13 (s, 1H), 5.85 (s, 2H), 3.79 (m, 3H), 3.73 (m, 2H), 3.51 (t, J=10.8 Hz, 2H), 3.26 (bs, 4H), 2.43 (bs, 4H), 2.22 (s, 3H), 1.94 (m, 2H), 1.71 (s, 3H), 1.44 (m, 2H).

(ESI+) MS: m/z 667.4 (MH$^{-1}$).

Example 15 (Method B): synthesis of N-[5-[(3,5-difluorophenyl)methyl]-6-[1-(2-hydroxy-1,1-dimethyl-ethyl)pyrazol-4-yl]-1H-indazol-3-yl]-4-(4-methylpiperazin-1-yl)-2-(tetrahydropyran-4-ylamino)benzamide [(Ia); $R_2$=$R_5$=H; Ar=3,5-difluorophenyl; $R_4$=1-(2-hydroxy-1,1-dimethyl-ethyl)pyrazol-4-yl; $R_6$=4-(4-methylpiperazin-1-yl)-2-(tetrahydropyran-4-ylamino)phenyl]

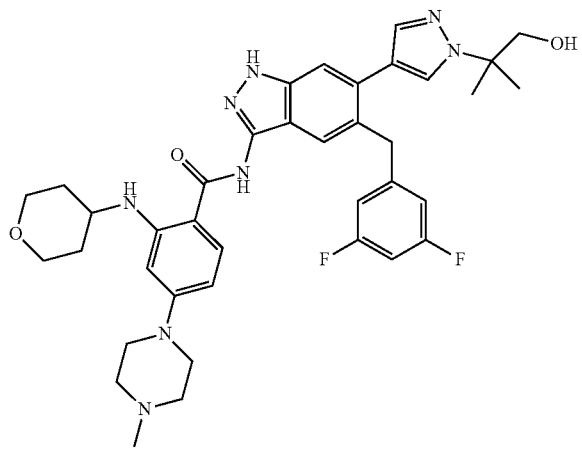 [SMILES: CN1CCN(c2ccc(C(=O)Nc3n[nH]c4cc(-c5cnn(C(C)(C)CO)c5)c(Cc5cc(F)cc(F)c5)cc34)c(NC3CCOCC3)c2)CC1]

$^1$H NMR (400 MHz, DMSO-$d_6$) δ 12.58 (s, 1H), 10.10 (s, 1H), 8.27 (d, J=7.6 Hz, 1H), 7.76 (m, 2H), 7.47 (m, 2H), 7.30 (s, 1H), 6.90 (t, J=9.2 Hz, 1H), 6.58 (d, J=7.6 Hz, 2H), 6.19 (d, J=1.6 Hz, 1H), 6.08 (s, 1H), 4.95 (m, 1H), 4.10 (s, 2H), 3.76 (m, 2H), 3.62 (m, 1H), 3.60 (m, 2H), 3.43 (t, J=10 Hz, 2H), 3.21 (bs, 4H), 2.38 (bs, 4H), 2.28 (s, 3H), 1 89 (m, 2H), 1.38 (s, 6H), 1.32 (m, 2H).

(ESI+) MS: m/z 350.3 (MH$^+$/2).

Example 16 (Method B): synthesis of N-[5-[(3,5-difluorophenyl)methyl]-6-(2-oxo-1H-pyridin-4-yl)-1H-indazol-3-yl]-4-(4-methylpiperazin-1-yl)-2-(tetrahydropyran-4-ylamino)benzamide [(Ia); $R_2$=$R_5$=H; Ar=3,5-difluorophenyl; $R_4$=2-oxo-1H-pyridin-4-yl; $R_6$=4-(4-methylpiperazin-1-yl)-2-(tetrahydropyran-4-ylamino)phenyl]

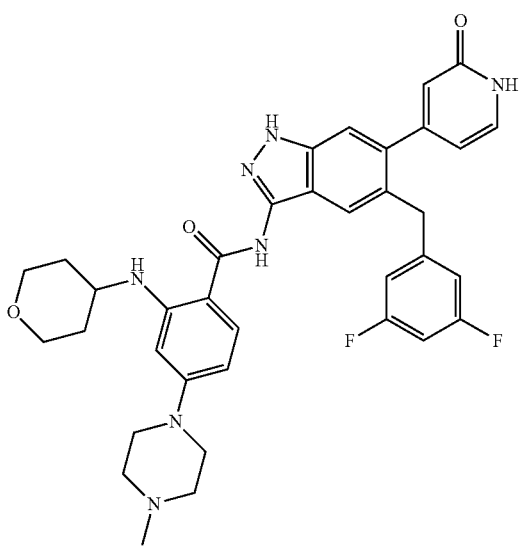 [SMILES: CN1CCN(c2ccc(C(=O)Nc3n[nH]c4cc(-c5cc[nH]c(=O)c5)c(Cc5cc(F)cc(F)c5)cc34)c(NC3CCOCC3)c2)CC1]

$^1$H NMR (400 MHz, DMSO-$d_6$) δ 12.77 (s, 1H), 11.63 (bs, 1H), 10.19 (s, 1H), 8.31 (d, J=8 Hz, 1H), 7.81 (d, J=9.2 Hz, 1H), 7.54 (s, 1H), 7.38 (d, J=6.4 Hz, 1H), 7.27 (s, 1H), 6.97 (m, 1H), 6.65 (d, J=6.4 Hz, 2H), 6.24 (d, J=8 Hz, 1H), 6.12 (m, 3H), 4.05 (s, 2H), 3.82 (m, 2H), 3.68 (m, 1H), 3.48 (t, J=10 Hz, 2H), 3.22 (bs, 4H), 2.43 (bs, 4H), 2.38 (s, 3H), 1.87 (m, 2H), 1.31 (m, 2H).

(ESI+) MS: m/z 654.2 (MH+).

Example 17 (Method B): synthesis of N-[5-[(3,5-difluorophenyl)methyl]-6-(3H-imidazo [4,5-b]pyridin-6-yl)-1H-indazol-3-yl]-4-(4-methylpiperazin-1-yl)-2-(tetrahydropyran-4-ylamino)benzamide [(Ia); $R_2$=$R_5$=H; Ar=3,5-difluorophenyl; $R_4$=3H-imidazo[4,5-b]pyridin-6-yl; $R_6$=4-(4-methylpiperazin-1-yl)-2-(tetrahydropyran-4-ylamino)phenyl]

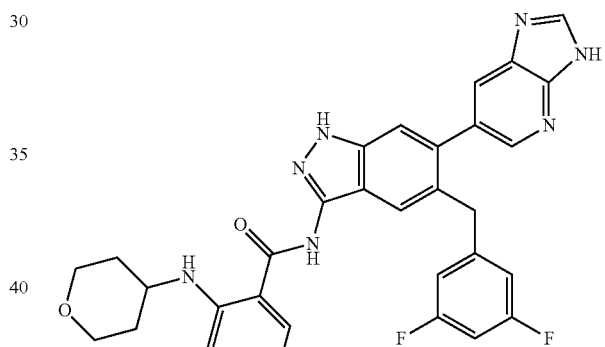
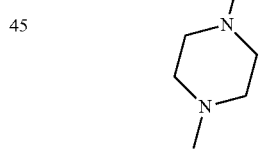

$^1$H NMR (400 MHz, CD$_3$OD) δ 8.43 (s, 1H), 8.18 (bs, 1H), 7.78 (m, 3H), 7.39 (s, 1H), 6.59 (tt, J=11.6 Hz, 6.8 Hz, 1H), 6.35 (m, 3H), 6.23 (d, J=2.2 Hz, 1H), 4.03 (s, 2H), 3.95 (m, 2H), 3.70 (m, 1H), 3.61 (td, J=10 Hz, J=2.2 Hz, 2H), 3.36 (m, 4H), 2.62 (m, 4H), 2.36 (s, 3H), 2.05 (m, 2H), 1.53 (m, 2H).

(ESI+) MS: m/z 678.3 (MH$^{-1}$).

Example 18 (Method B): synthesis of N-[5-[(3,5-difluorophenyl)methyl]-6-(1H-pyrazol-4-yl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=1H-pyrazol-4-yl; R$_6$=4-(4-methylpiperazin-1-yl)-2-(tetrahydropyran-4-ylamino)phenyl]

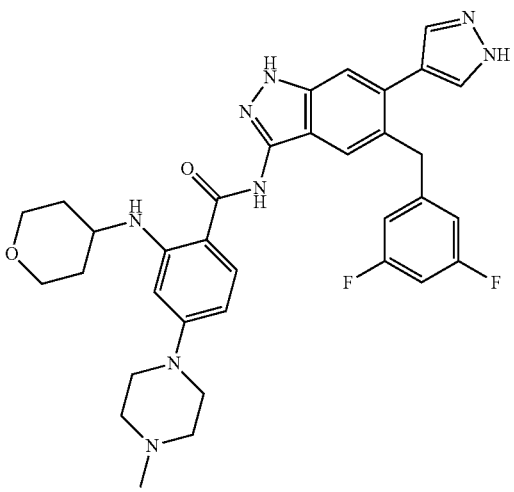 [SMILES: CN1CCN(c2ccc(C(=O)Nc3n[nH]c4cc(-c5cn[nH]c5)c(Cc5cc(F)cc(F)c5)cc34)c(NC3CCOCC3)c2)CC1]

$^1$H NMR (400 MHz, CD$_3$OD) δ 7.75 (d, J=8.8 Hz, 1H), 7.65 (s, 1H), 7.58 (bs, 1H), 7.56 (bs, 1H), 7.50 (s, 1H), 6.64 (tt, J=11.4 Hz, 6.4 Hz, 1H), 6.54 (d, J=6.4 Hz, 2H), 6.33 (d, J=8.8 Hz, 1H), 6.21 (d, J=2 Hz, 1H), 4.13 (s, 2H), 3.92 (m, 2H), 3.73 (m, 1H), 3.54 (td, J=10 Hz, J=2.2 Hz, 2H), 3.32 (m, 4H), 2.59 (m, 4H), 2.35 (s, 3H), 2.03 (m, 2H), 1.46 (m, 2H).

(ESI+) MS: m/z 627.3 (MH$^{-1}$).

Example 19 (Method B): synthesis of N-[5-[(3,5-difluorophenyl)methyl]-6-(3-fluoro-5-hydroxy-phenyl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=3-fluoro-5-hydroxy-phenyl; R$_6$=4-(4-methylpiperazin-1-yl)-2-(tetrahydropyran-4-ylamino)phenyl]

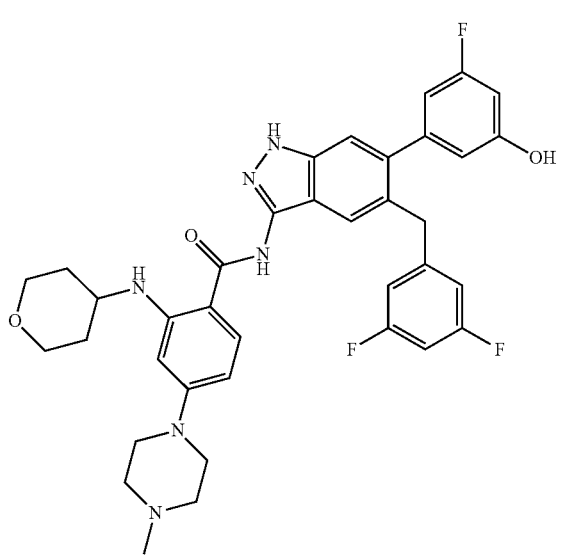 [SMILES: CN1CCN(c2ccc(C(=O)Nc3n[nH]c4cc(-c5cc(O)cc(F)c5)c(Cc5cc(F)cc(F)c5)cc34)c(NC3CCOCC3)c2)CC1]

$^1$H NMR (400 MHz, CD$_3$OD) δ 7.76 (d, J=8.4 Hz, 1H), 7.67 (s, 1H), 7.27 (s, 1H), 6.50 (m, 1H), 6.48-6.40 (m, 4H), 6.34 (m, 2H), 6.22 (s, 1H), 4.02 (s, 2H), 3.91 (m, 2H), 3.71 (m, 1H), 3.68 (td, J=11 Hz, J=2.2 Hz, 2H), 3.38 (m, 4H), 2.62 (m, 4H), 2.37 (s, 3H), 2.04 (m, 2H), 1.45 (m, 2H).

(ESI+) MS: m/z 671.3 (MH$^{-1}$).

Example 20 (Method B): synthesis of N-[5-[(3,5-difluorophenyl)methyl]-6-[4-(methylcarbamoyl)phenyl]-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=4-(methylcarbamoyl)phenyl; R$_6$=4-(4-methylpiperazin-1-yl)-2-(tetrahydropyran-4-ylamino)phenyl]

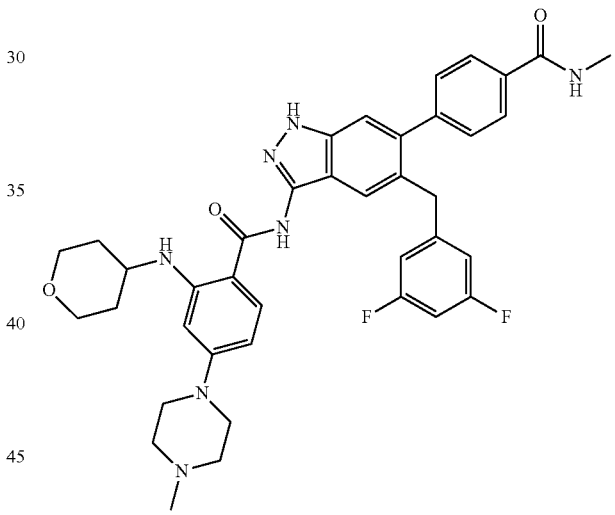

$^1$H NMR (400 MHz, DMSO-d$_6$) δ 12.73 (s, 1H), 10.20 (s, 1H), 8.49 (m, 1H), 8.33 (m, 1H), 7.88 (d, J=8.4 Hz, 2H), 7.82 (d, J=8.8 Hz, 1H), 7.57 (s, 1H), 7.36 (d, J=8.4 Hz, 2H), 7.26 (s, 1H), 6.91 (m, 1H), 6.49 (d, J=6.8 Hz, 2H), 6.25 (d, J=6.8 Hz, 1H), 6.13 (bs, 1H), 4.00 (s, 2H), 3.85 (m, 2H), 3.81 (m, 1H), 3.51 (td, J=10 Hz, J=2.2 Hz, 2H), 3.25 (m, 4H), 2.81 (d, J=4.4 Hz, 3H), 2.24 (m, 3H), 1.94 (m, 2H), 1.36 (m, 2H).

(ESI+) MS: m/z 694.4 (MH$^{-1}$).

Example 21 (Method B): synthesis of N-[5-[(3,5-difluorophenyl)methyl]-6-(4-hydroxy-3-methyl-phenyl)-1H-indazol-3-yl]-4-(4-methylpiperazin-1-yl)-2-(tetrahydropyran-4-ylamino)benzamide [(Ia); $R_2=R_5=H$; Ar=3,5-difluorophenyl; $R_4$=4-hydroxy-3-methyl-phenyl; $R_6$=4-(4-methylpiperazin-1-yl)-2-(tetrahydropyran-4-ylamino)phenyl]

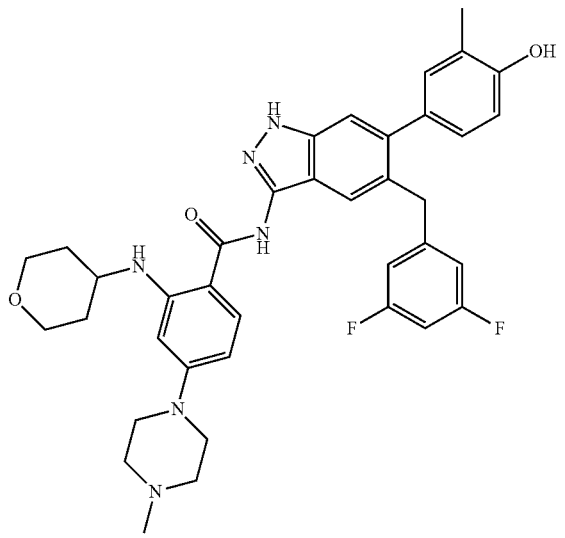 [SMILES: Cc1cc(-c2cc3[nH]nc(NC(=O)c4ccc(N5CCN(C)CC5)cc4NC4CCOCC4)c3cc2Cc2cc(F)cc(F)c2)ccc1O]

$^1$H NMR (400 MHz, DMSO-d$_6$) δ 12.61 (s, 1H), 10.15 (s, 1H), 9.38 (s, 1H), 8.34 (d, J=7.2 Hz, 1H) 7.81 (d, J=9.2 Hz, 1H), 7.51 (s, 1H), 7.17 (s, 1H), 6.94-6.86 (m, 4H), 6.52 (d, J=7.2 Hz, 2H), 6.25 (dd, J=9.2 Hz, 2 Hz, 1H), 6.13 (dd, J=1.6 Hz, 1H), 3.97 (s, 2H), 3.81 (dt, J=12 Hz, 3.6 Hz, 2H), 3.68 (m, 1H), 3.47 (td, J=10 Hz, J=2.2 Hz, 2H), 3.30 (m, 4H), 2.44 (m, 4H), 2.22 (s, 3H), 2.11 (s, 3H), 1.91 (m, 2H), 1.34 (m, 2H).
(ESI+) MS: m/z 667.3 (MH$^{-1}$).

Example 22 (Method B): synthesis of N-[5-[(3,5-difluorophenyl)methyl]-6-(6-hydroxy-3-pyridyl)-1H-indazol-3-yl]-4-(4-methylpiperazin-1-yl)-2-(tetrahydropyran-4-ylamino)benzamide [(Ia); $R_2=R_5=H$; Ar=3,5-difluorophenyl; $R_4$=6-hydroxy-3-pyridyl; $R_6$=4-(4-methylpiperazin-1-yl)-2-(tetrahydropyran-4-ylamino)phenyl]

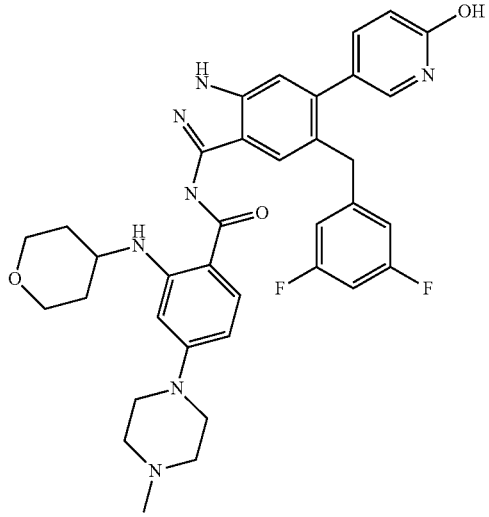

$^1$H NMR (400 MHz, CD$_3$OD) δ 7.67 (d, J=8.4 Hz, 1H), 7.63 (s, 1H), 7.39 (dd, J=9.2 Hz, 2.4 Hz, 1H), 7.23 (s, 1H), 7.04 (dd, J=2.4 Hz, 1H), 6.58 (m, 1H), 6.45-6.41 (m, 3H), 6.25 (dd, J=9.2 Hz, 2 Hz, 1H), 6.13 (dd, J=1.6 Hz, 1H), 3.96 (s, 2H), 3.84 (m, 2H), 3.58 (m, 1H), 3.49 (td, J=11 Hz, J=2.2 Hz, 2H), 3.25 (m, 4H), 2.52 (m, 4H), 2.27 (s, 3H), 1.95 (m, 2H), 1.44 (m, 2H).

(ESI+) MS: m/z 654.2 (MH$^{-1}$).

Example 23 (Method B): synthesis of N-[5-[(3,5-difluorophenyl)methyl]-6-phenyl-1H-indazol-3-yl]-4-(4-methylpiperazin-1-yl)-2-(tetrahydropyran-4-ylamino)benzamide [(Ia); $R_2=R_5=H$; Ar=3,5-difluorophenyl; $R_4$=phenyl; $R_6$=4-(4-methylpiperazin-1-yl)-2-(tetrahydropyran-4-ylamino)phenyl]

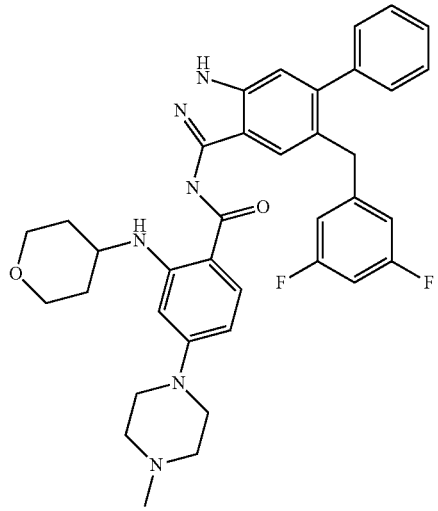

$^1$H NMR (400 MHz, DMSO-d$_6$) δ 12.70 (s, 1H), 10.19 (s, 1H), 8.34 (d, J=7.6 Hz, 1H), 7.82 (d, J=8.8 Hz, 1H), 7.56 (s, 1H), 7.44-7.38 (m, 3H), 7.26-7.23 (m, 3H), 6.90 (m, 1H), 6.45 (m, 2H), 6.25 (dd, J=8.8 Hz, 2 Hz, 1H), 6.13 (d, J=2 Hz, 1H), 4.00 (s, 2H), 3.83 (m, 2H), 3.69 (m, 1H), 3.51 (td, J=11 Hz, J=2.2 Hz, 2H), 3.30 (m, 4H), 2.44 (m, 4H), 2.22 (s, 3H), 1.95 (m, 2H), 1.35 (m, 2H).

(ESI+) MS: m/z 637.4 (MH$^{-1}$).

Example 24 (Method B): synthesis of N-[5-[(3,5-difluorophenyl)methyl]-6-(3-methoxyphenyl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=3-methoxy-phenyl; R$_6$=4-(4-methylpiperazin-1-yl)-2-(tetrahydropyran-4-ylamino)phenyl]

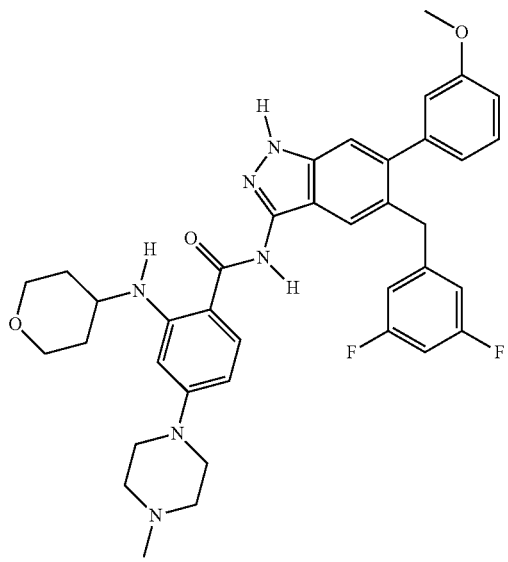 [SMILES: COc1cccc(-c2cc3[nH]nc(NC(=O)c4ccc(N5CCN(C)CC5)cc4NC4CCOCC4)c3cc2Cc2cc(F)cc(F)c2)c1]

$^1$H NMR (400 MHz, MeOD) δ 7.80 (d, J=J=7.6 Hz, 1H), 7.69 (s, 1H), 7.29-7.25 (m, 2H), 6.92 (dd, J=8.8 Hz, 2 Hz, 1H), 6.77 (d, J=7.6 Hz, 1H), 6.65-6.59 (m, 2H), 6.39 (d, J=8.8 Hz, 2H), 6.34 (dd, J=8.8 Hz, 2 Hz, 1H), 6.23 (d, J=2 Hz, 1H), 4.00 (s, 2H), 3.95 (m, 2H), 3.67 (sb, 4H), 3.61 (td, J=11 Hz, J=2.2 Hz, 2H), 3.35 (m, 4H), 2.62 (m, 4H), 2.36 (s, 3H), 2.05 (m, 2H), 1.52 (m, 2H).
(ESI+) MS: m/z 667.5 (MH$^+$).

Example 25 (Method B): synthesis of N-[5-[(3,5-difluorophenyl)methyl]-6-(3-fluoro-4-hydroxy-phenyl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=3-fluoro-4-hydroxy-phenyl; R$_6$=4-(4-methylpiperazin-1-yl)-2-(tetrahydropyran-4-ylamino)phenyl]

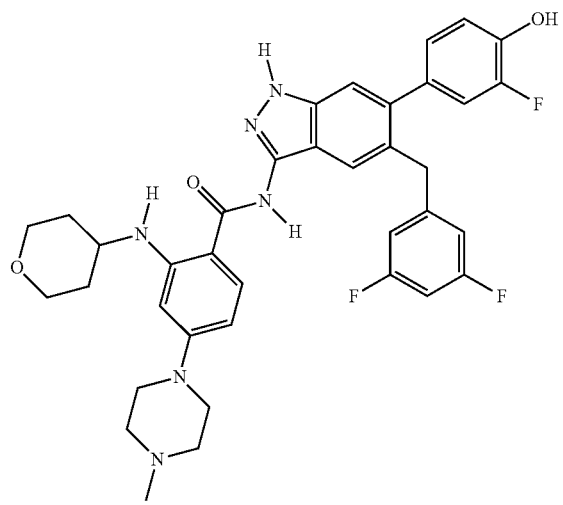 [SMILES: CN1CCN(c2ccc(C(=O)Nc3n[nH]c4cc(-c5ccc(O)c(F)c5)c(Cc5cc(F)cc(F)c5)cc34)c(NC3CCOCC3)c2)CC1]

$^1$H NMR (400 MHz, DMSO-d$_6$) δ 12.69 (s, 1H), 10.20 (s, 1H), 9.94 (s, 1H), 8.34 (dd, J=7.6 Hz, 1H), 7.83 (d, J=9.2 Hz, 1H), 7.52 (s, 1H), 7.21 (s, 1H), 7.02-6.87 (m, 4H), 6.52 (d, J=7.6 Hz, 2H), 6.26 (d, J=9.2 Hz, 1H), 6.14 (s, 1H), 4.00 (s, 2H), 3.82 (m, 2H), 3.68 (m, 1H), 3.48 (td, J=10 Hz, J=2.1 Hz, 2H), 3.25 (m, 4H), 2.52 (m, 4H), 2.48 (s, 3H), 1.93 (m, 2H), 1.32 (m, 2H).

(ESI+) MS: m/z 671.3 (MH$^+$).

Example 26 (Method B): synthesis of N-[5-[(3,5-difluorophenyl)methyl]-6-(1H-indazol-5-yl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=1H-indazol-5-yl; R$_6$=4-(4-methylpiperazin-1-yl)-2-(tetrahydropyran-4-ylamino)phenyl]

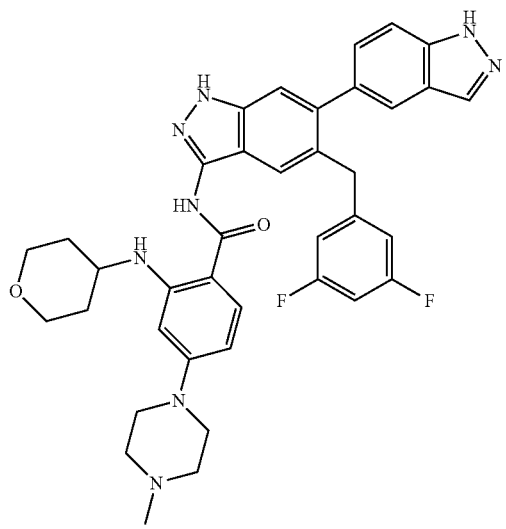 [SMILES: CN1CCN(c2ccc(C(=O)Nc3n[nH]c4cc(-c5ccc6[nH]ncc6c5)c(Cc5cc(F)cc(F)c5)cc34)c(NC3CCOCC3)c2)CC1]

$^1$H NMR (400 MHz, DMSO-d$_6$) δ 13.14 (s, 1H), 12.68 (s, 1H), 10.19 (s, 1H), 8.35 (d, J=7.6 Hz, 1H), 8.08 (s, 1H), 7.83 (d, J=8.8 Hz, 1H), 7.61-7.55 (m, 3H), 7.24 (s, 1H), 7.22 (d, J=1.2 Hz, 1H), 6.89 (t, J=2.4 Hz, 1H), 6.45 (d, J=7.6 Hz, 2H), 6.25 (d, J=8.8 Hz, 1H), 6.13 (s, 1H), 4.00 (s, 2H), 3.82 (m, 2H), 3.69 (m, 1H), 3.51 (t, J=9.6 Hz, 2H), 3.27 (bs, 4H), 2.48 (m, 4H), 2.23 (s, 3H), 1.94 (m, 2H), 1.35 (m, 2H).

(ESI+) MS: m/z 677.3 (MH$^+$).

Example 27 (Method B): synthesis of N-[5-[(3,5-difluorophenyl)methyl]-6-(pyrimidin-5-yl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=6-pyrimidin-5-yl; R$_6$=4-(4-methylpiperazin-1-yl)-2-(tetrahydropyran-4-ylamino)phenyl]

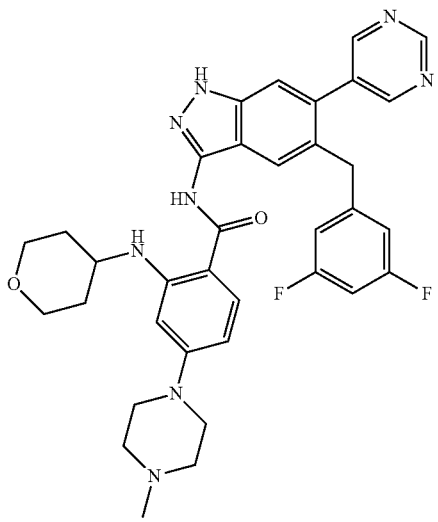 [SMILES: CN1CCN(c2ccc(C(=O)Nc3n[nH]c4cc(-c5cncnc5)c(Cc5cc(F)cc(F)c5)cc34)c(NC3CCOCC3)c2)CC1]

$^1$H NMR (400 MHz, DMSO-d$_6$) δ 12.87 (s, 1H), 10.24 (s, 1H), 9.14 (s, 1H), 8.69 (s, 2H), 8.33 (d, J=7.6 Hz, 1H), 7.83 (d, J=9.2 Hz, 1H), 7.67 (s, 1H), 7.39 (s, 1H), 6.96 (m, 1H), 6.47 (d, J=7.6 Hz, 2H), 6.26 (d, J=9.2 Hz, 1H), 6.13 (d, J=2 Hz, 1H), 4.04 (s, 2H), 3.83 (m, 2H), 3.69 (m, 1H), 3.48 (t, J=9.6 Hz, 2H), 3.27 (m, 4H), 2.51 (m, 4H), 2.22 (s, 3H), 1.92 (m, 2H), 1.37 (m, 2H).
(ESI+) MS: m/z 639.3 (MH$^{-1}$).

Example 28 (Method B): synthesis of N-[5-[(3,5-difluorophenyl)methyl]-6-(3-oxoisoindolin-5-yl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=3-oxoisoindolin-5-yl; R$_6$=4-(4-methylpiperazin-1-yl)-2-(tetrahydropyran-4-ylamino)phenyl]

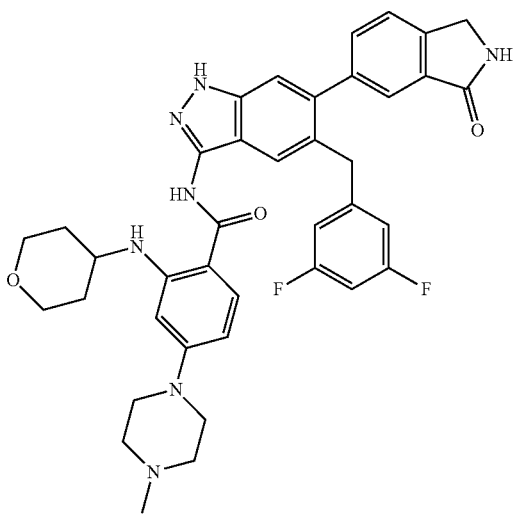 [SMILES: CN1CCN(c2ccc(C(=O)Nc3n[nH]c4cc(-c5ccc6c(c5)C(=O)NC6)c(Cc5cc(F)cc(F)c5)cc34)c(NC3CCOCC3)c2)CC1]

$^1$H NMR (400 MHz, DMSO-d$_6$) δ 12.73 (s, 1H), 10.13 (s, 1H), 8.64 (s, 1H), 8.33 (d, J=7.6 Hz, 1H), 7.82 (d, J=9.2 Hz, 1H), 7.62 (d, J=7.6 Hz, 1H), 7.56 (s, 1H), 7.49 (m, 2H), 7.46 (s, 1H), 6.90 (m, 1H), 6.49 (d, J=7.6 Hz; 2H), 6.25 (d, J=9.2 Hz, 1.6 Hz, 1H), 6.13 (s, 1H), 4.43 (s, 2H), 3.98 (s, 2H), 3.82 (m, 2H), 3.68 (m, 1H), 3.52 (t, J=9.6 Hz, 2H), 3.33 (m, 4H), 2.44 (m, 4H), 2.19 (s, 3H), 1.87 (m, 2H), 1.38 (m, 2H).
(ESI+) MS: m/z 692.4 (MH$^{-1}$).

Example 29 (Method B): synthesis of N-[5-[(3,5-difluorophenyl)methyl]-6-(1H-pyrrolo[2,3-b]pyridin-5-yl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=1H-pyrrolo[2,3-b]pyridin-5-yl; R$_6$=4-(4-methylpiperazin-1-yl)-2-(tetrahydropyran-4-yl)phenyl]

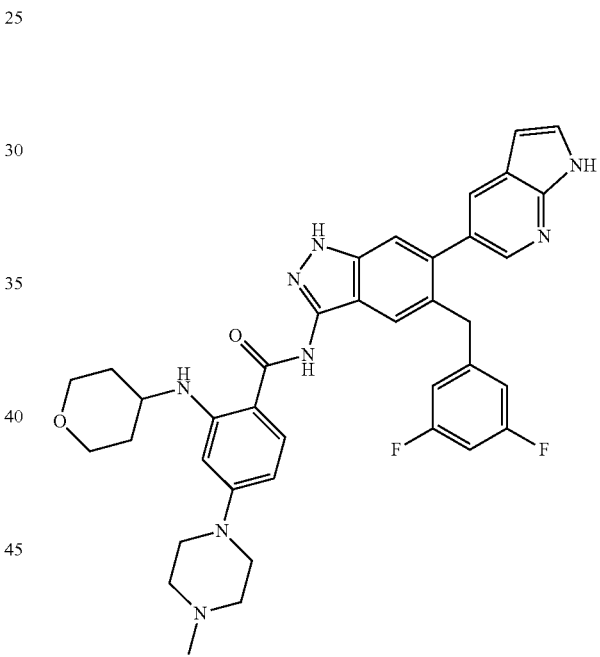

$^1$H NMR (400 MHz, DMSO-d$_6$) δ 12.63 (s, 1H), 11.67 (s, 1H), 10.18 (s, 1H), 8.34 (d, J=7.6 Hz, 1H), 8.053 (d, J=2 Hz, 1H), 7.82 (m, 2H), 7.56 (s, 1H), 7.52 (m, 1H), 7.31 (s, 1H), 6.90 (m, 1H), 6.46 (m, 3H), 6.25 (d, J=7.6 Hz, 2 Hz, 1H), 6.13 (s, 1H), 4.03 (s, 2H), 3.83 (m, 2H), 3.69 (m, 1H), 3.49 (t, J=9.6 Hz, 2H), 3.27 (m, 4H), 2.50 (m, 4H), 2.43 (s, 3H), 1.97 (m, 2H), 1.36 (m, 2H).
(ESI+) MS: m/z 676.3 (MH$^+$).

Example 30 (Method B): synthesis of N-[5-[(3,5-difluorophenyl)methyl]-6-(4-pyridyl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=4-pyridyl; R$_{6=4}$-(4-methylpiperazin-1-yl)-2-(tetrahydropyran-4-ylamino)phenyl]

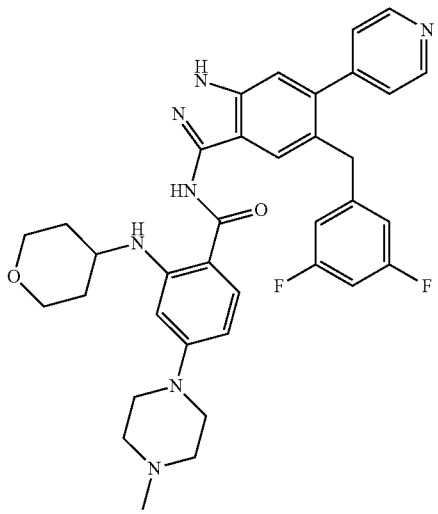

$^1$H NMR (400 MHz, DMSO-d$_6$) δ 12.81 (s, 1H), 10.23 (s, 1H), 8.60-8.58 (m, 2H), 8.33 (d, J=8.0 Hz, 1H), 7.82 (d, J=9.2 Hz, 1H), 7.61 (s, 1H), 7.31-7.29 (m, 3H), 6.96-6.91 (m, 1H), 6.49 (d, J=6.8 Hz, 2H), 6.24 (dd, J=8.8 Hz, 2.0 Hz, 1H), 6.13 (d, J=2.0 Hz, 1H), 4.03 (s, 2H), 3.83-3.79 (m, 2H), 3.69-3.67 (m, 1H), 3.51-3.46 (m, 2H), 3.27-3.25 (m, 4H), 2.44-2.42 (m, 4H), 2.23 (s, 3H), 1.94-1.92 (m, 2H), 1.38-1.29 (m, 2H).
(ESI+) MS: m/z 638.3 (MH$^+$).

Example 31 (Method B): synthesis of N-[5-[(3,5-difluorophenyl)methyl]-6-(3-pyridyl)-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=3-pyridyl; R$_{6=4}$-(4-methylpiperazin-1-yl)-2-(tetrahydropyran-4-ylamino)phenyl]

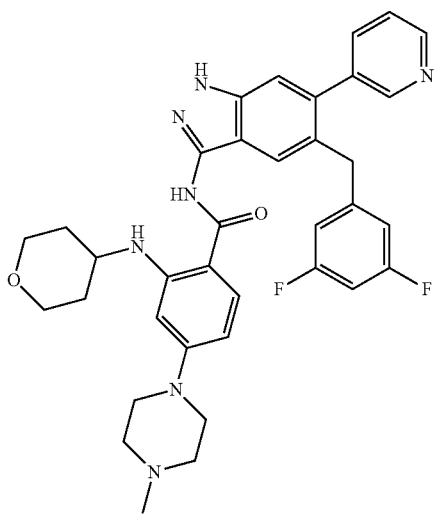

$^1$H NMR (400 MHz, DMSO-d$_6$) δ 12.79 (s, 1H), 10.23 (s, 1H), 8.58-8.56 (m, 1H), 8.43 (d, J=2.0 Hz, 1H), 8.33 (d, J=7.6 Hz, 1H), 7.82 (d, J=9.2 Hz, 1H), 7.70-7.67 (m, 1H), 7.61 (s, 1H), 7.44-7.41 (m, 1H), 7.30 (s, 1H), 6.95-6.90 (m, 1H), 6.46-6.44 (m, 2H), 6.24 (dd, J=8.8 Hz, 2.0 Hz, 1H), 6.13 (d, J=1.2 Hz, 1H), 4.01 (s, 2H), 3.84-3.79 (m, 2H), 3.71-3.66 (m, 1H), 3.51-3.46 (m, 2H), 3.28-3.25 (m, 4H), 2.44-2.42 (m, 4H), 2.22 (s, 3H), 1.95-1.92 (m, 2H), 1.38-1.33 (m, 2H).
(ESI+) MS: m/z 638.3 (MH$^+$).

Example 32 (Method B): synthesis of N-[5-[(3,5-difluorophenyl)methyl]-6-[4-(1-hydroxy-1-methyl-ethyl)phenyl]-1H-indazol-3-yl]-4-(4-methylpiperazin-1-yl)-2-(tetrahydropyran-4-ylamino)benzamide [(Ia); R$_2$=R$_5$=H; Ar=3,5-difluorophenyl; R$_4$=[4-(1-hydroxy-1-methyl-ethyl)phenyl]; R$_{6=4}$-(4-methylpiperazin-1-yl)-2-(tetrahydropyran-4-ylamino)phenyl]

a) Synthesis of N-[6-bromo-5-[(3,5-difluorophenyl)methyl]-1H-indazol-3-yl]-4-(4-methylpiperazin-1-yl)-2-[tetrahydropyran-4-yl-(2,2,2-trifluoroacetyl)amino]benzamide [XXIIa; R$_2$=R$_5$=H; Ar=3,5-difluorophenyl; Hal=Br; R'$_6$=4-(4-methylpiperazin-1-yl)-2-(2,2,2-trifluoro-N-(tetrahydropyran-4-yl)-acetamido)phenyl]

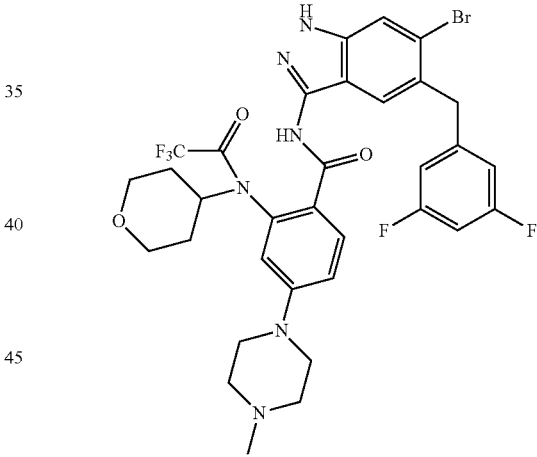

The solution of N-[6-bromo-5-[(3,5-difluorophenyl)methyl]-1-trityl-indazol-3-yl]-4-(4-methylpiperazin-1-yl)-2-[tetrahydropyran-4-yl-(2,2,2-trifluoroacetyl)amino]benzamide (250 mg) in TFA was stirred at room temperature for 1 hour. The solvent was removed under vacuum. The residue was purified by flash column chromatography with eluent DCM/MeOH/NH$_4$OH 40:1:0.5 to afford the title compound as brown foam (130 mg, 69%).

$^1$H NMR (400 MHz, CD$_3$OD) δ 7.75 (d, J=8.8 Hz, 1H), 7.68 (s, 1H), 7.58 (s, 1H), 7.03 (dd, J=8.8 Hz, 2.4 Hz, 1H), 6.78 (d, J=2.4 Hz, 1H), 6.69-6.62 (m, 3H), 4.51-4.41 (m, 1H), 4.12 (s, 2H), 3.85-3.83 (m, 1H), 3.73-3.70 (m, 1H), 3.38-3.35 (m, 1H), 3.33-3.27 (m, 5H), 2.58-2.55 (m, 4H), 2.30 (s, 3H), 1.94-1.89 (m, 2H), 1.70-1.66 (m, 1H), 1.58-1.54 (m, 1H).
(ESI+) MS: m/z 736.2 (MH$^+$).

b) Synthesis of N-[5-[(3,5-difluorophenyl)methyl]-6-[4-(1-hydroxy-1-methyl-ethyl)phenyl]-1H-indazol-3-yl]-4-(4-methylpiperazin-1-yl)-2-(tetrahydropyran-4-ylamino)benzamide [(Ia); $R_2=R_5=H$; Ar=3,5-difluorophenyl; $R_4$=[4-(1-hydroxy-1-methyl-ethyl)phenyl]; $R_6$=4-(4-methylpiperazin-1-yl)-2-(tetrahydropyran-4-ylamino)phenyl]

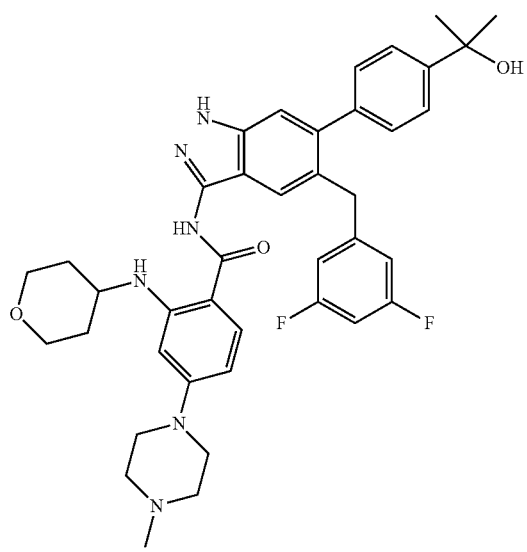

To a mixture of N-[6-bromo-5-[(3,5-difluorophenyl)methyl]-1H-indazol-3-yl]-4-(4-methylpiperazin-1-yl)-2-[tetrahydropyran-4-yl-(2,2,2-trifluoroacetyl)amino]benzamide (130 mg, 0.18 mmol), boronic acid (140 mg, 0.45 mmol), $Cs_2CO_3$ (1M, 0.50 ml) in dioxane (2.5 ml) was added Pd(dppf)$Cl_2$ (30 mg) under argon atmosphere. The mixture was heated to 120'C in a sealed tube and stirred for 60 minutes. The solvent was removed and the residue was purified by flash column chromatography with a gradient eluent from DCM:MeOH 100:1 to 40:1 and preparative HPLC to afford the title compound as white solid (30 mg, 24%).

$^1$H NMR (400 MHz, DMSO-$d_6$) δ 12.68 (s, 1H), 10.18 (s, 1H), 8.35-8.33 (m, 1H), 7.81 (d, J=9.2 Hz, 1H), 7.54 (s, 1H), 7.51 (s, 1H), 7.49 (s, 1H), 7.23 (s, 1H), 7.19 (s, 1H), 7.17 (s, 1H), 6.92-6.87 (m, 1H), 6.44-6.42 (m, 2H), 6.24 (dd, J=8.0 Hz, 1.9 Hz, 1H), 6.13 (d, J=2.0 Hz, 1H), 5.06 (s, 1H), 4.00 (s, 2H), 3.83-3.79 (m, 2H), 3.70-3.66 (m, 1H), 3.52-3.46 (m, 2H), 3.27-3.23 (m, 4H), 2.44-2.43 (m, 4H), 2.22 (s, 3H), 1.95-1.92 (m, 2H), 1.47 (s, 6H), 1.38-1.29 (m, 2H).

(ESI+) MS: m/z 695.3 (MH$^+$).

Example 33 (Method B): synthesis of N-[5-[(3,5-difluorophenyl)methyl]-6-(4-hydroxyphenyl)-1H-indazol-3-yl]-4-(4-methylpiperazin-1-yl)benzamide [(Ia); $R_2=R_5=H$; Ar=3,5-difluorophenyl; $R_4$=4-hydroxy-phenyl; $R_6$=4-(4-methylpiperazin-1-yl)phenyl]

a) Synthesis of N-[6-bromo-5-[(3,5-difluorophenyl)methyl]-1-trityl-indazol-3-yl]-4-(4-methylpiperazin-1-yl)benzamide [XXII; $R_2=R_5=H$; Hal=Br; Ar=3,5-difluorophenyl; P=Trityl; $R_6$=4-(4-methylpiperazin-1-yl)-2-phenyl]

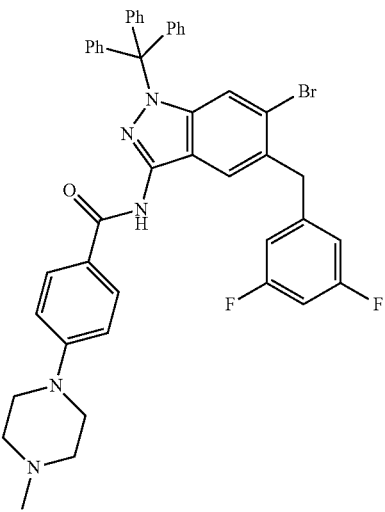 [SMILES: CN1CCN(c2ccc(C(=O)Nc3nn(C(c4ccccc4)(c4ccccc4)c4ccccc4)c4cc(Br)c(Cc5cc(F)cc(F)c5)cc34)cc2)CC1]

To a solution of 6-bromo-5-[(3,5-difluorophenyl)methyl]-1-trityl-indazol-3-amine under nitrogen atmosphere (1 mmol, 0.58 g) in THF (10 ml) was added DMAP (0.1 mmol, 20 mg) and DIPEA (6 mmol, 0.6 g); 4-(4-methylpiperazin-4-ium-1-yl)benzoyl chloride (3 eq.) was added in portions. The resulting mixture was immediately warmed up to 50° C. and stirred for 1 h. After the reaction was completed, the mixture was partitioned between water and DCM. The organic phase was washed with NaOH solution (1M), brine and water. The resulting solution was dried over sodium sulfate and evaporated to dryness. The residue was purified by flash column chromatography with eluent AcOEt/MeOH 20:1 to afford the title compound as a white solid (300 mg, 38%).

$^1$H NMR (400 MHz, CDCl$_3$) δ 8.47 (s, 1H), 8.09-8.10 (m, 1H), 7.82 (d, J=8.8 Hz, 2H), 7.23-7.32 (m, 15H), 6.92 (d, J=8.0 Hz, 2H), 6.65-6.67 (m, 2H), 6.56-6.62 (m, 1H), 6.55 (s, 1H), 4.11 (s, 2H), 3.33-3.36 (m, 4H), 2.54-2.58 (m, 4H), 2.36 (s, 3H).

(ESI+) MS: m/z 782.3 (MH$^+$).

b) Synthesis of N-[5-[(3,5-difluorophenyl)methyl]-6-(4-hydroxyphenyl)-1-trityl-indazol-3-yl]-4-(4-methylpiperazin-1-yl)benzamide [XXIII; R$_2$=R$_5$=H; R$_4$=4-hydroxyphenyl; Ar=3,5-difluorophenyl; P=Trityl; R$_6$=4-(4-methylpiperazin-1-yl)-2-phenyl]

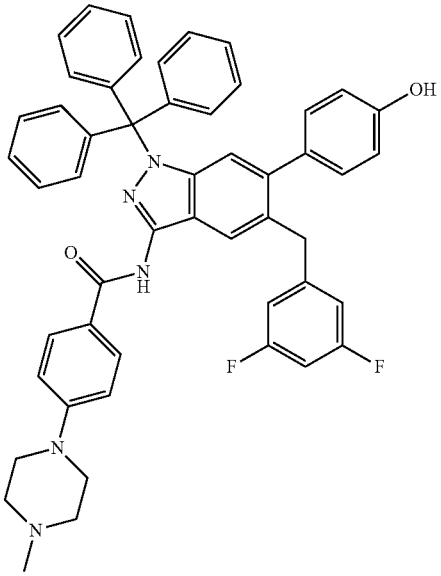 [SMILES: CN1CCN(c2ccc(C(=O)Nc3nn(C(c4ccccc4)(c4ccccc4)c4ccccc4)c4cc(-c5ccc(O)cc5)c(Cc5cc(F)cc(F)c5)cc34)cc2)CC1]

To a round bottom flask under nitrogen atmosphere containing N-[6-bromo-5-[(3,5-difluorophenyl)methyl]-1-trityl-indazol-3-yl]-4-(4-methylpiperazin-1-yl)benzamide (0.26 mmol, 200 mg), cesium carbonate (424 mg, 1.3 mmol), 4-hydroxy-phenyl boronic acid (71 mg, 0.52 mmol) in a mixture dioxane/water (3:1, 3.0 ml), was added Pd(PPh$_3$)$_4$ (50 mg, 0.043 mmol) under argon atmosphere. The mixture was stirred at 100° C. under microwave irradiation for 90 minutes. The mixture was partitioned between water and DCM. The organic phase was washed with water and brine. The resulting solution was dried over sodium sulfate and evaporated to dryness. The residue was purified by flash column chromatography with a gradient eluent from DCM/MeOH 100:1 to DCM/MeOH 40:1 affording the title compound as brown foam (150 mg, 73%).

c) Synthesis of N-[5-[(3,5-difluorophenyl)methyl]-6-(4-hydroxyphenyl)-1H-indazol-3-yl]-4-(4-methylpiperazin-1-yl)benzamide [(Ia); R$_2$=R$_5$=H; Ar=3,5-difluorophenyl; R$_4$=4-hydroxy-phenyl; R$_6$=4-(4-methylpiperazin-1-yl)phenyl]

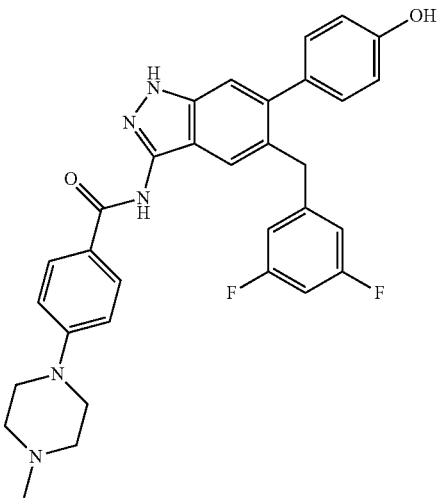 [SMILES: CN1CCN(c2ccc(C(=O)Nc3n[nH]c4cc(-c5ccc(O)cc5)c(Cc5cc(F)cc(F)c5)cc34)cc2)CC1]

A solution of N-[5-[(3,5-difluorophenyl)methyl]-6-(4-hydroxyphenyl)-1-trityl-indazol-3-yl]-4-(4-methylpiperazin-1-yl)benzamide (150 mg, 0.19 mmol) in TFA (2 ml) was stirred for 60 minutes at room temperature. The solvent was removed and the residue was purified by preparative HPLC to afford the title compound as a white solid (47 mg, 45%).

$^1$H NMR (400 MHz, DMSO-d$_6$) δ 12.68 (s, 1H), 10.47 (s, 1H), 9.49 (s, 1H), 7.97 (d, J=8.8 Hz, 2H), 7.63 (s, 1H), 7.19 (s, 1H), 7.02 (m, 4H), 6.92 (m, 1H), 6.78 (d, J=8.8 Hz, 2H), 6.43 (m, 2H), 4.01 (s, 2H), 3.31 (m, 4H), 2.46 (m, 4H), 2.23 (s, 3H).

(ESI+) MS: m/z 554.3 (MH$^+$).

Analogously to Example 33 the following Examples 34, 35, 36 and 37 were prepared in agreement with Method B:

Example 34 (Method B): synthesis of N-[5-[(3,5-difluorophenyl)methyl]-6-(4-hydroxy-2-methyl-phenyl)-1H-indazol-3-yl]-4-(4-methylpiperazin-1-yl)benzamide [(Ia); R$_2$=R$_5$=H; Ar=3,5-difluorophenyl; R$_4$=4-hydroxy-2-methyl-phenyl; R$_6$=4-(4-methylpiperazin-1-yl)phenyl]

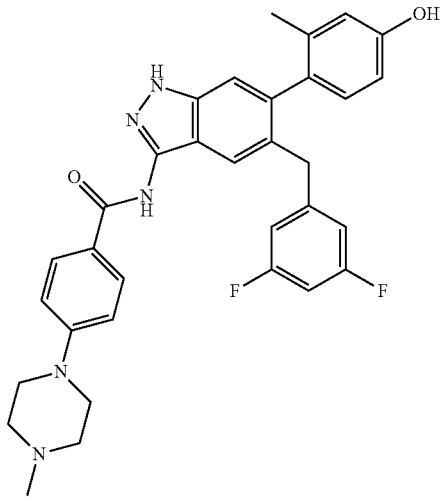 [SMILES: Cc1cc(O)ccc1-c1cc2[nH]nc(NC(=O)c3ccc(N4CCN(C)CC4)cc3)c2cc1Cc1cc(F)cc(F)c1]

$^1$H NMR (400 MHz, DMSO-d$_6$) δ 12.64 (s, 1H), 10.46 (s, 1H), 9.34 (s, 1H), 7.98 (d, J=8.8 Hz, 2H), 7.68 (s, 1H), 7.10 (s, 1H), 7.03 (d, J=8.8 Hz, 2H), 6.90 (m, 1H), 6.78 (d, J=8 Hz, 1H), 6.57 (m, 3H), 6.35 (d, J=6.8 Hz, 1H), 3 89 (d, J=14.8 Hz, 1H), 3.72 (d, J=14.8 Hz, 1H), 3.30 (m, 4H), 2.44 (m, 4H), 2.23 (s, 3H), 1.72 (s, 3H).

(ESI+) MS: m/z 568.3 (MH$^+$).

Example 35 (Method B): synthesis of N-[5-[(3,5-difluorophenyl)methyl]-6-(1H-indazol-5-yl)-1H-indazol-3-yl]-4-(4-methylpiperazin-1-yl)benzamide [(Ia); R$_2$=R$_5$=H; Ar=3,5-difluorophenyl; R$_4$=1H-indazol-3-yl; R$_6$=4-(4-methylpiperazin-1-yl)phenyl]

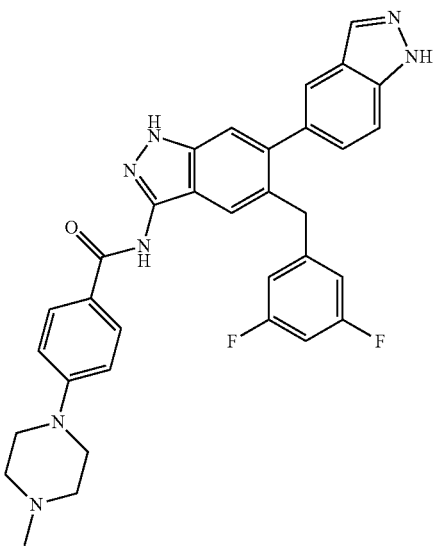 [SMILES: CN1CCN(c2ccc(C(=O)Nc3n[nH]c4cc(-c5ccc6[nH]ncc6c5)c(Cc5cc(F)cc(F)c5)cc34)cc2)CC1]

<sup>1</sup>H NMR (400 MHz, DMSO-d$_6$) δ 13.06 (s, 1H), 12.67 (s, 1H), 10.43 (s, 1H), 7 99 (s, 1H), 7.91 (d, J=9.2 Hz, 2H), 7.60 (s, 1H), 7.51 (s, 1H), 7.48 (d, J=8.4 Hz, 1H), 7.22 (s, 1H), 7.14 (d, J=8.4 Hz, 1H), 6.96 (d, J=8.8 Hz, 2H), 6.79 (m, 1H), 6.30 (d, J=6.8 Hz, 2H), 3.95 (s, 2H), 3.24 (m, 4H), 2.39 (m, 4H), 2.15 (s, 3H).

(ESI+) MS: m/z 578.3 (MH$^+$).

Example 36 (Method B): synthesis of N-[6-(2-aminopyrimidin-5-yl)-5-[(3,5-difluorophenyl)methyl]-1H-indazol-3-yl]-4-(4-methylpiperazin-1-yl)benzamide [(Ia); R$_2$=R$_5$=H; Ar=3,5-difluorophenyl; R$_4$=2-aminopyrimidin-5-yl; R$_6$=4-(4-methylpiperazin-1-yl)phenyl

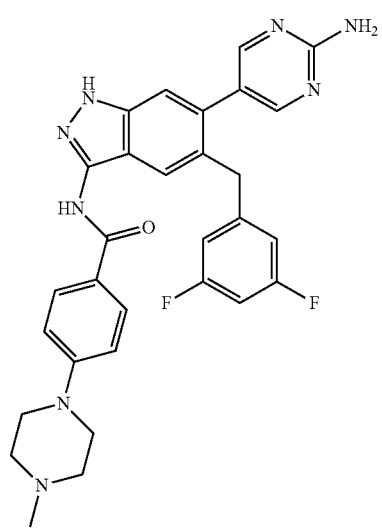 [SMILES: CN1CCN(c2ccc(C(=O)Nc3n[nH]c4cc(-c5cnc(N)nc5)c(Cc5cc(F)cc(F)c5)cc34)cc2)CC1]

<sup>1</sup>H NMR (400 MHz, DMSO-d$_6$) δ 12.77 (s, 1H), 10.49 (s, 1H), 8.05 (s, 2H), 7.97 (d, J=8.8 Hz, 2H), 7.68 (s, 1H), 7.27 (s, 1H), 7.02 (d, J=8.8 Hz, 2H), 6.93 (m, 1H), 6.69 (s, 2H), 6.50 (d, J=6.4 Hz, 2H), 4.04 (s, 2H), 3.29 (m, 4H), 2.49 (m, 4H), 2.23 (s, 3H).

(ESI+) MS: m/z 555.3 (MH$^+$).

Example 37 (Method B): synthesis of N-[5-[(3,5-difluorophenyl)methyl]-6-(4-hydroxy-3-methyl-phenyl)-1H-indazol-3-yl]-4-(4-methylpiperazin-1-yl)benzamide [(Ia); R$_2$=R$_5$=H; Ar=3,5-difluorophenyl; R$_4$=4-hydroxy-3-methyl-phenyl; R$_6$=4-(4-methylpiperazin-1-yl)phenyl

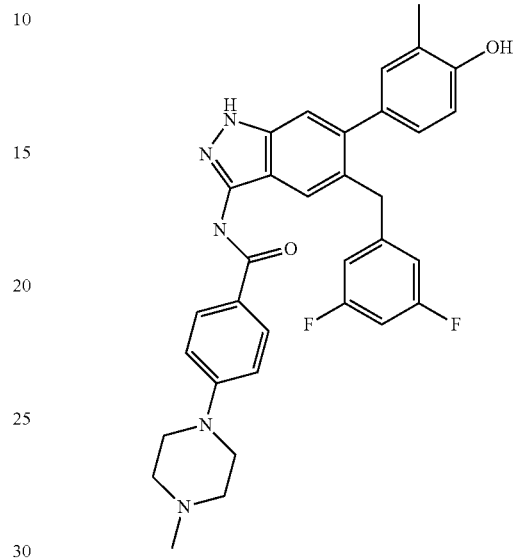

<sup>1</sup>H NMR (400 MHz, DMSO-d$_6$) δ 12.67 (s, 1H), 10.47 (s, 1H), 9.38 (s, 1H), 7.97 (d, J=8.8 Hz, 2H), 7.63 (s, 1H), 7.18 (s, 1H), 7.02 (d, J=9.2 Hz, 2H), 6.94-6.90 (m, 1H), 6.86-6.84 (m, 2H), 6.79-6.77 (m, 1H), 6.45 (d, J=6.8 Hz, 2H), 4.00 (s, 2H), 3.32-3.29 (m, 4H), 2.50-2.46 (m, 4H), 2.24 (s, 3H), 2.10 (s, 3H).

(ESI+) MS: m/z 568.2 (MH$^+$).

Example 38 (Method B): synthesis of N-[5-[(3-fluorophenyl)methyl]-6-(4-hydroxyphenyl)-1H-indazol-3-yl]-4-(4-methylpiperazin-1-yl)-2-(tetrahydropyran-4-ylamino)benzamide [(Ia); R$_2$=R$_5$=H; Ar=3-fluorophenyl; R$_4$=4-hydroxy-phenyl; R$_6$=4-(4-methylpiperazin-1-yl)-2-(tetrahydropyran-4-ylamino)phenyl]

a) Synthesis of 3-fluorobenzene Grignard Reagent

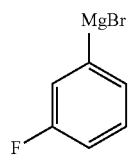

Under nitrogen atmosphere a mixture of Mg (0.114 mol, 2.7 g), 12 (trace) and THF (80 ml) was stirred at 60° C. A solution of 1-bromo-3-fluoro-benzene (0.057 mol, 10 g) in dry THF (30 ml) was added dropwise keeping the temperature between 50° C. to 60° C. After the addition the solution was left to room temperature with stirring and then used directly in the next step.

b) Synthesis of 4-bromo-2-fluoro-5-[(3-fluorophenyl)-hydroxy-methyl]benzonitrile [VII; $R_2=R_5=H$; Hal=Br; Ar=3-fluorophenyl]

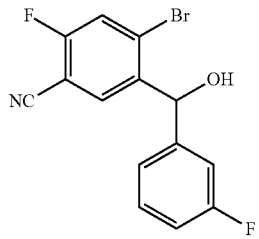 [SMILES: N#Cc1cc(C(O)c2cccc(F)c2)c(Br)cc1F]

A solution of 4-bromo-2-fluoro-5-formylbenzonitrile (0.053 mol, 12 g) under nitrogen atmosphere in THF (100 ml) was slowly added to 3-fluorobenzene Grignard reagent (0.058 mol, 115 ml, 0.5M in THF) at −15° C. The mixture was stirred for 2 h at the same temperature. After the reaction was completed, the resulting mixture was quenched with saturated $NH_4Cl$ solution and extracted with AcOEt. The organic phase was dried over sodium sulfate and evaporated to dryness. The residue was purified by flash column chromatography with eluent Ether/AcOEt 10:1 to afford the title compound as a white solid (12 g, 70%).

$^1$H NMR (400 MHz, $CDCl_3$) δ 7.92 (d, J=6.4 Hz, 1H), 7.46 (d, J=8.4 Hz, 1H), 7.30-7.35 (m, 1H), 7.00-7.13 (m, 3H), 6.08-6.09 (m, 1H).

c) Synthesis of 4-bromo-2-fluoro-5-[(3-fluorophenyl)methyl]benzonitrile [VIII; $R_2=R_5=H$; Hal=Br; Ar=3-fluorophenyl]

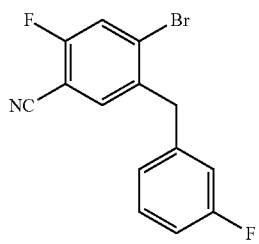 [SMILES: N#Cc1cc(Cc2cccc(F)c2)c(Br)cc1F]

To a solution of 4-bromo-2-fluoro-5-[(3-fluorophenyl)-hydroxy-methyl]benzonitrile (0.037 mol, 12 g) in $CH_3CN$ (200 ml) was added NaI (0.37 mol, 55 g). The mixture was warmed up to 70° C. TMSCl (0.37 mol, 40 g) was added slowly over 8 h under nitrogen atmosphere. After the addition, the reaction was completed. The mixture was partitioned between water and DCM. The organic phase was washed with $NaHSO_3$ (1M), saturated $NaHCO_3$ solution and brine. The resulting solution was dried over sodium sulfate and evaporated to dryness. The residue was purified by flash column chromatography with eluent PE/AcOEt 10:1 to afford the title compound as a white solid (4 g, 35%).

$^1$H NMR (400 MHz, $CDCl_3$) δ 7.51 (d, J=8.4 Hz, 1H), 7.32 (d, J=6.8 Hz, 1H), 6.92-7.00 (m, 2H), 6.83-6.86 (m, 2H), 4.08 (s, 2H).

d) Synthesis of 6-bromo-5-[(3-fluorophenyl)methyl]-1H-indazol-3-amine [XVIII; $R_2=R_5=H$; Hal=Br; Ar=3-fluorophenyl]

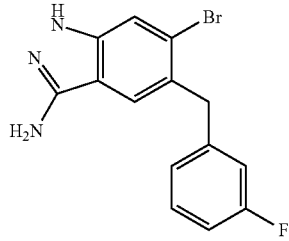

To a solution of 4-bromo-2-fluoro-5-[(3-fluorophenyl)methyl]benzonitrile (6.5 mmol, 2 g) in ethanol (10 ml) was added hydrazine hydrate 80% (65 mmol, 4 ml). The mixture was refluxed over 18 h. The mixture was partitioned between water and DCM. The organic phase was dried over sodium sulfate and evaporated to dryness. The title compound was obtained as a white solid and used without further purification in the following reaction (1.6 g, 77%).

$^1$H NMR (400 MHz, $CDCl_3$) δ 9.06 (s, 1H), 7.59 (s, 1H), 7.29 (s, 1H), 7.23-7.27 (m, 1H), 6.86-6.98 (m, 3H), 4.18 (s, 2H), 4.10 (s, 2H).

(ESI+) MS: m/z 320.1 ($MH^+$).

e) Synthesis of N-[6-bromo-5-[(3-fluorophenyl)methyl]-1H-indazol-3-yl]-2,2,2-trifluoro-acetamide [XIX; $R_2=R_5=H$; Hal=Br; Ar=3-fluorophenyl; P'=2,2,2-trifluoroacetyl]

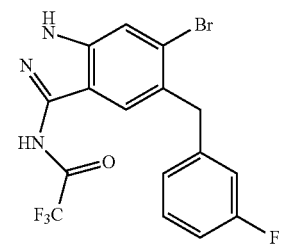

Under nitrogen atmosphere to a solution of 6-bromo-5-[(3-fluorophenyl)methyl]-1H-indazol-3-amine (5 mmol, 1.6 g) in DCM (20 ml) was added TEA (10 mmol, 1 g) at 0° C. TFAA (7.5 mmol, 1.58 g) was then added carefully. After the reaction was complete, the solvent was removed and the residue was dissolved with AcOEt. The solution was washed with saturated $NaHCO_3$ solution. The organic phase was dried over sodium sulfate and evaporated to dryness. The title compound was obtained as a yellow oil and used in the following reaction without further purification (1.8 g, 77%).

$^1$H NMR (400 MHz, MeOD) δ 7.81 (s, 1H), 7.74 (s, 1H), 7.25-7.31 (m, 1H), 7.00-7.02 (m, 1H), 6.89-6.92 (m, 2H), 4.23 (s, 2H).

(ESI+) MS: m/z 416.0 ($MH^+$).

f) Synthesis of N-[6-bromo-5-[(3-fluorophenyl) methyl]-1-trityl-indazol-3-yl]-2,2,2-trifluoro-acetamide [XX; R$_2$=R$_5$=H; Hal=Br; Ar=3-fluorophenyl; P'=2,2,2-trifluoroacetyl; P=Trityl]

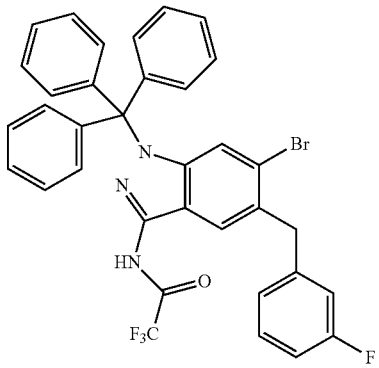 [SMILES: N=C(NC(=O)C(F)(F)F)c1cc(Cc2cccc(F)c2)c(Br)cc1NC(c1ccccc1)(c1ccccc1)c1ccccc1]

Under nitrogen atmosphere to a solution of N-[6-bromo-5-[(3-fluorophenyl)methyl]-1H-indazol-3-yl]-2,2,2-trifluoro-acetamide (4.3 mmol, 1.8 g) in DCM were added TEA (8.6 mmol, 0.86 g) and trityl chloride (6.45 mmol, 1.8 g). The mixture was stirred for 2 h at room temperature. After the reaction was completed, the mixture was washed with saturated NH$_4$Cl solution. The organic phase was dried over sodium sulfate and evaporated to dryness. The residue was purified by flash column chromatography with eluent PE/AcOEt 5:1 to afford the title compound as a white solid (1.4 g, 50%).

$^1$H NMR (400 MHz, CClD$_3$) δ 8.75 (s, 1H), 7.89 (s, 1H), 7.14-7.34 (m, 15H), 6.97 (d, J=8.0 Hz, 1H), 6.84-6.90 (m, 2H), 6.58 (s, 1H), 4.11 (s, 2H).
(ESI+) MS: m/z 680.2 (MNa$^+$).

g) Synthesis of 6-bromo-5-[(3-fluorophenyl) methyl]-1-trityl-indazol-3-amine [XXI; R$_2$=R$_5$=H; Hal=Br; Ar=3-fluorophenyl; P=Trityl]

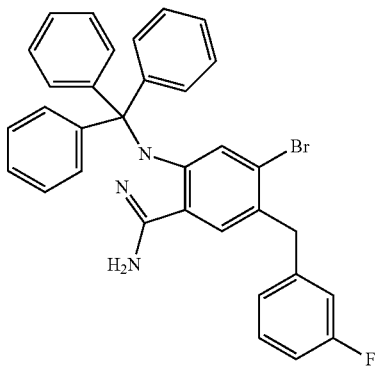 [SMILES: N=C(N)c1cc(Cc2cccc(F)c2)c(Br)cc1NC(c1ccccc1)(c1ccccc1)c1ccccc1]

To a solution of N-[6-bromo-5-[(3-fluorophenyl)methyl]-1-trityl-indazol-3-yl]-2,2,2-trifluoro-acetamide (2.1 mmol, 1.4 g) in MeOH (10 ml) was added TEA (6.3 mmol, 0.63 g). The mixture was stirred for 18 h at 60° C. The solvent was removed and the residue was purified by flash column chromatography with eluent PE/AcOEt 3:1 to afford the title compound as a white solid (1 g, 85%).

$^1$H NMR (400 MHz, CD$_3$Cl) δ 7.22-7.33 (m, 15H), 7.18-7.20 (m, 1H), 7.11 (s, 1H), 6.83-6.96 (m, 3H), 6.45 (s, 1H), 4.06 (s, 2H), 3.97 (s, 2H).

h) Synthesis of N-[6-bromo-5-[(3-fluorophenyl) methyl]-1-trityl-indazol-3-yl]-4-(4-methylpiperazin-1-yl)-2-[tetrahydropyran-4-yl-(2,2,2-trifluoroacetyl) amino]benzamide [XXII; R$_2$=R$_5$=H; Hal=Br; Ar=3-fluorophenyl; P=Trityl; R'$_6$=4-(4-methylpiperazin-1-yl)-2-(2,2,2-trifluoro-N-(tetrahydropyran-4-yl)-acetamido)phenyl]

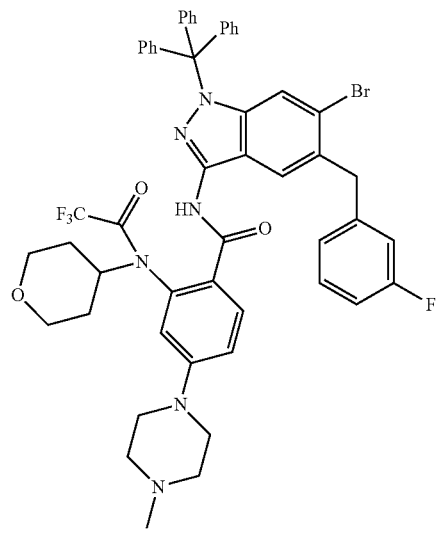 [SMILES: CN1CCN(c2ccc(C(=O)Nc3nn(C(c4ccccc4)(c4ccccc4)c4ccccc4)c4cc(Br)c(Cc5cccc(F)c5)cc34)c(N(C(=O)C(F)(F)F)C3CCOCC3)c2)CC1]

Under nitrogen atmosphere to a solution of 6-bromo-5-[(3-fluorophenyl)methyl]-1-trityl-indazol-3-amine (1.8 mmol, 1 g) in THF (10 ml) was added DMAP (0.18 mmol, 22 mg) and DIPEA (10.8 mmol, 1.1 g); 4-(4-methylpiperazin-4-ium-1-yl)-2-[tetrahydropyran-4-yl-(2,2,2-trifluoroacetyl)amino]benzoyl chloride (2.7 eq.) was then added in portions. The resulting mixture was immediately warmed up to 50° C. for 1 h. After the reaction was completed, the mixture was partitioned between water and DCM. The organic phase was washed by NaOH solution (1M), brine and water. The resulting solution was dried over sodium sulfate and evaporated to dryness. The residue was purified by flash column chromatography with eluent AcOEt/MeOH 20:1 to afford the title compound as a white solid (700 mg, 40%).

$^1$H NMR (400 MHz, CDCl$_3$) δ 8.23 (s, 1H), 7.75 (s, 1H), 7.66 (d, J=8.8 Hz, 1H), 7.14-7.34 (m, 15H), 7.03 (d, J=7.6 Hz, 1H), 6.85-6.91 (m, 3H), 6.62 (d, J=1.6 Hz, 1H), 6.53 (d, J=3.6 Hz, 1H), 4.59-4.65 (m, 1H), 4.10 (s, 2H), 3.95-3.98 (m, 1H), 3.77-3.81 (m, 1H), 3.47-3.52 (m, 1H), 3.29-3.40 (m, 5H), 2.58 (t, J=4.8 Hz, 4H), 2.37 (s, 3H), 1.64-1.72 (m, 2H), 1.22-1.31 (m, 2H).

i) Synthesis of N-[5-[(3-fluorophenyl)methyl]-6-(4-hydroxyphenyl)-1-trityl-indazol-3-yl]-4-(4-methyl-piperazin-1-yl)-2-(tetrahydropyran-4-ylamino)benzamide [XXIII; $R_2$=$R_5$=H; Ar=3-fluorophenyl; P=Trityl; $R_4$=4-hydroxy-phenyl; $R_6$=4-(4-methyl-piperazin-1-yl)-2-(tetrahydropyran-4-ylamino)-phenyl]

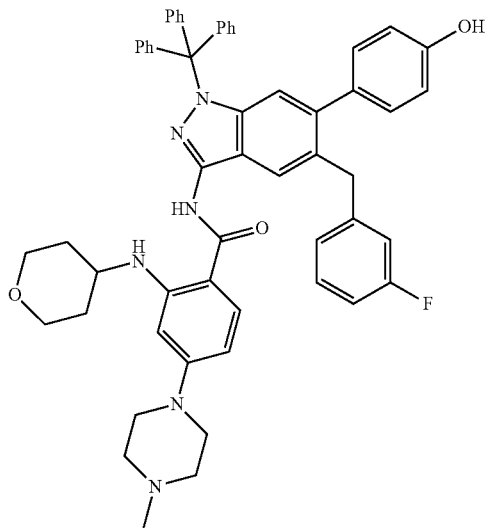 [SMILES: CN1CCN(c2ccc(C(=O)Nc3nn(C(c4ccccc4)(c4ccccc4)c4ccccc4)c4cc(-c5ccc(O)cc5)c(Cc5cccc(F)c5)cc34)c(NC3CCOCC3)c2)CC1]

To a mixture of N-[6-bromo-5-[(3-fluorophenyl)methyl]-1-trityl-indazol-3-yl]-4-(4-methylpiperazin-1-yl)-2-[tetrahydropyran-4-yl-(2,2,2-trifluoroacetyl)amino]benzamide (200 mg, 0.21 mmol), 4-hydroxyphenylboronic acid (58 mg, 0.42 mmol), $Cs_2CO_3$ (350 mg, 1.1 mmol) in a mixture dioxane/water (3:1, 3.0 ml) was added Pd(PPh$_3$)$_4$ (50 mg) under argon atmosphere. The mixture was heated to 100° C. under microwave irradiation and stirred for 90 minutes. The solvent was removed and the residue was purified by silica gel column with a gradient eluent from DCM:MeOH 100:1 to 40:1 affording the title compound as brown foam (140 mg, 77%).

j) Synthesis of N-[5-[(3-fluorophenyl)methyl]-6-(4-hydroxyphenyl)-1H-indazol-3-yl]-4-(4-methylpiperazin-1-yl)-2-(tetrahydropyran-4-ylamino)benzamide [(Ia); $R_2$=$R_5$=H; Ar=3-fluorophenyl; $R_4$=4-hydroxy-phenyl; $R_6$=4-(4-methylpiperazin-1-yl)-2-(tetrahydropyran-4-ylamino)-phenyl]

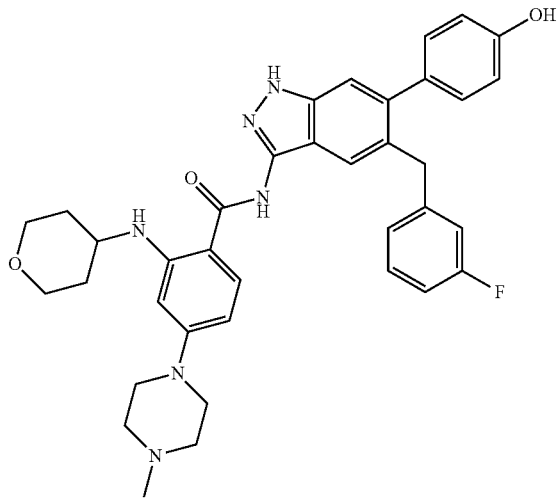 [SMILES: CN1CCN(c2ccc(C(=O)Nc3n[nH]c4cc(-c5ccc(O)cc5)c(Cc5cccc(F)c5)cc34)c(NC3CCOCC3)c2)CC1]

A solution of N-[5-[(3-fluorophenyl)methyl]-6-(4-hydroxyphenyl)-1-trityl-indazol-3-yl]-4-(4-methylpiperazin-1-yl)-2-(tetrahydropyran-4-ylamino)benzamide in TFA (2 ml) was stirred for 1 hour minutes at room temperature. The solvent was removed and the residue was purified by preparative HPLC to afford the title compound as a white solid (40 mg, 40%).

$^1$H NMR (400 MHz, DMSO-d$_6$) δ 12.60 (s, 1H), 10.14 (s, 1H), 9.49 (s, 1H), 8.33 (d, J=7.6 Hz, 1H), 7.80 (d, J=9.2 Hz, 1H), 7.48 (s, 1H), 7.19 (m, 2H); 7.14 (d, J=8.4 Hz, 2H), 6.87 (m, 1H), 6.77 (d, J=8.4 Hz, 2H), 6.71 (d, J=7.6 Hz, 1H), 6.63 (d, J=9.2 Hz, 1H), 6.23 (d, J=9.2 Hz, 1H), 6.12 (s, 1H), 3.98 (s, 2H), 3.83 (m, 2H), 3.67 (m, 1H), 3.51 (t, J=9.6 Hz, 2H), 3.28 (m, 4H), 2.44 (m, 4H), 2.18 (s, 3H), 1.89 (m, 2H), 1.33 (m, 2H).

(ESI+) MS: m/z 635.3 (MH$^+$).

Analogously to Example 38 the following Examples 39, 40 and 41 were prepared in agreement with Method B:

Example 39 (Method B): synthesis of N-[6-(3-fluoro-4-hydroxy-phenyl)-5-[(3-fluorophenyl)methyl]-1H-indazol-3-yl]-4-(4-methylpiperazin-1-yl)-2-(tetrahydropyran-4-ylamino)benzamide [(Ia); $R_2$=$R_5$=H; Ar=3-fluorophenyl; $R_4$=3-fluoro-4-hydroxy-phenyl; $R_6$=4-(4-methylpiperazin-1-yl)-2-(tetrahydropyran-4-ylamino)phenyl]

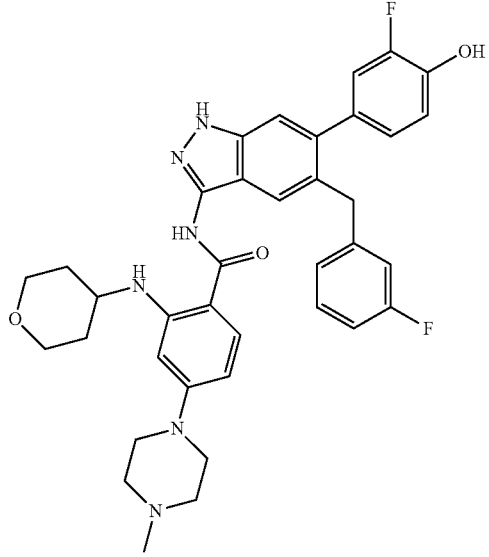 [SMILES: CN1CCN(c2ccc(C(=O)Nc3n[nH]c4cc(-c5ccc(O)c(F)c5)c(Cc5cccc(F)c5)cc34)c(NC3CCOCC3)c2)CC1]

$^1$H NMR (400 MHz, DMSO-d$_6$) δ 12.65 (s, 1H), 10.16 (s, 1H), 9.92 (s, 1H), 8.33-8.31 (m, 1H), 7.80 (d, J=9.2 Hz, 1H), 7.50 (s, 1H), 7.21 (s, 1H), 7.19-7.15 (m, 1H), 7.02-6.86 (m, 4H), 6.72-6.70 (m, 1H), 6.65-6.62 (m, 1H), 6.23 (dd, J=9.2 Hz, 2.0 Hz, 1H), 6.12 (d, J=2.0 Hz, 1H), 3.99 (s, 2H), 3.83-3.79 (m, 2H), 3.69-3.67 (m, 1H), 3.52-3.46 (m, 2H), 3.27-3.24 (m, 4H), 2.44-2.42 (m, 4H), 2.22 (s, 3H), 1.94-1.91 (m, 2H), 1.38-1.33 (m, 2H).

(ESI+) MS: m/z 653.3 (MH$^+$).

Example 40 (Method B): synthesis of N-[6-(2-fluoro-4-hydroxy-phenyl)-5-[(3-fluorophenyl)methyl]-1H-indazol-3-yl]-4-(4-methylpiperazin-1-yl)-2-(tetrahydropyran-4-ylamino)benzamide [(Ia); $R_2=R_5=H$; Ar=3-fluorophenyl; $R_4$=2-fluoro-4-hydroxy-phenyl; $R_6$=4-(4-methylpiperazin-1-yl)-2-(tetrahydropyran-4-ylamino)phenyl]

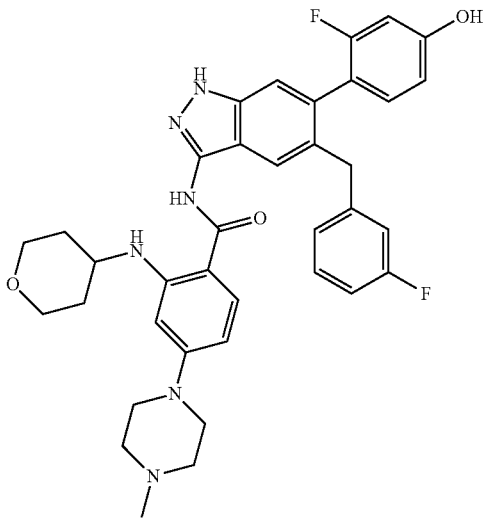 [SMILES: CN1CCN(c2ccc(C(=O)Nc3n[nH]c4cc(-c5ccc(O)cc5F)c(Cc5cccc(F)c5)cc34)c(NC3CCOCC3)c2)CC1]

$^1$H NMR (400 MHz, DMSO-$d_6$) δ 12.66 (s, 1H), 10.16 (s, 1H), 9.97 (s, 1H), 8.32-8.31 (m, 1H), 7.80 (d, J=9.2 Hz, 1H), 7.52 (s, 1H), 7.21 (s, 1H), 7.18-7.12 (m, 1H), 7.01-6.95 (m, 1H), 6.91-6.86 (m, 1H), 6.67-6.55 (m, 4H), 6.23 (dd, J=8.4 Hz, 1.6 Hz, 1H), 6.12 (d, J=2.4 Hz, 1H), 3.88 (s, 2H), 3.83-3.80 (m, 2H), 3.72-3.66 (m, 1H), 3.52-3.46 (m, 2H), 3.28-3.23 (m, 4H), 2.44-2.40 (m, 4H), 2.22 (s, 3H), 1.95-1.91 (m, 2H), 1.39-1.31 (m, 2H).

(ESI+) MS: m/z 653.3 (MH$^+$).

Example 41 (Method B): synthesis of N-[6-(2-aminopyrimidin-5-yl)-5-[(3-fluorophenyl)methyl]-1H-indazol-3-yl]-4-(4-methylpiperazin-1-yl)benzamide [(Ia); $R_2=R_5=H$; Ar=3-fluorophenyl; $R_4$=2-aminopyrimidin-5-yl; $R_6$=4-(4-methylpiperazin-1-yl)phenyl]

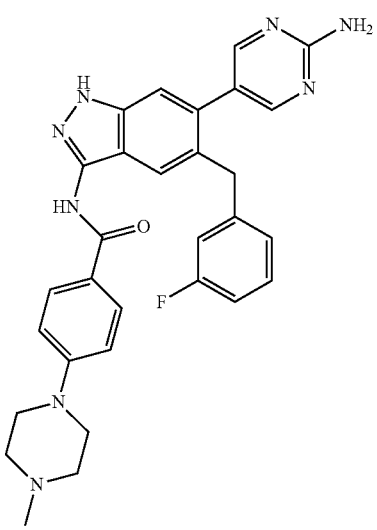 [SMILES: CN1CCN(c2ccc(C(=O)Nc3n[nH]c4cc(-c5cnc(N)nc5)c(Cc5cccc(F)c5)cc34)cc2)CC1]

$^1$H NMR (400 MHz, DMSO-$d_6$) δ 12.76 (s, 1H), 10.49 (s, 1H), 8.05 (s, 2H), 7.96 (d, J=8.8 Hz, 2H), 7.67 (s, 1H), 7.27 (s, 1H), 7.22-7.16 (m, 1H), 7.01 (d, J=9.2 Hz, 2H), 6.93-6.88 (m, 1H), 6.69-6.67 (m, 3H), 6.62 (d, J=10.0 Hz, 1H), 4.03 (s, 2H), 3.32-3.29 (m, 4H), 2.50-2.44 (m, 4H), 2.23 (s, 3H).

(ESI+) MS: m/z 537.4 (MH$^+$).

Example 42 (Method B): synthesis of N-[6-(3-fluoro-4-hydroxy-phenyl)-5-[(3-fluorophenyl)methyl]-1H-indazol-3-yl]-2-(2-methoxyethylamino)-4-(4-methylpiperazin-1-yl)benzamide [(Ia); $R_2=R_5=H$; Ar=3-fluorophenyl; $R_4$=3-fluoro-4-hydroxy-phenyl; $R_6$=4-(4-methylpiperazin-1-yl)-2-(2-methoxyethylamino)phenyl]

a) Synthesis of N-[6-bromo-5-[(3-fluorophenyl)methyl]-1-trityl-indazol-3-yl]-2-[2-methoxyethyl-(2,2,2-trifluoroacetyl)amino]-4-(4-methylpiperazin-1-yl)benzamide [XXII; $R_2=R_5=H$; Ar=3-fluorophenyl; Hal=Br; P=Trityl; R'$_6$=[2-[2-methoxyethyl-(2,2,2-trifluoroacetyl)amino]-4-(4-methylpiperazin-1-yl)phenyl]

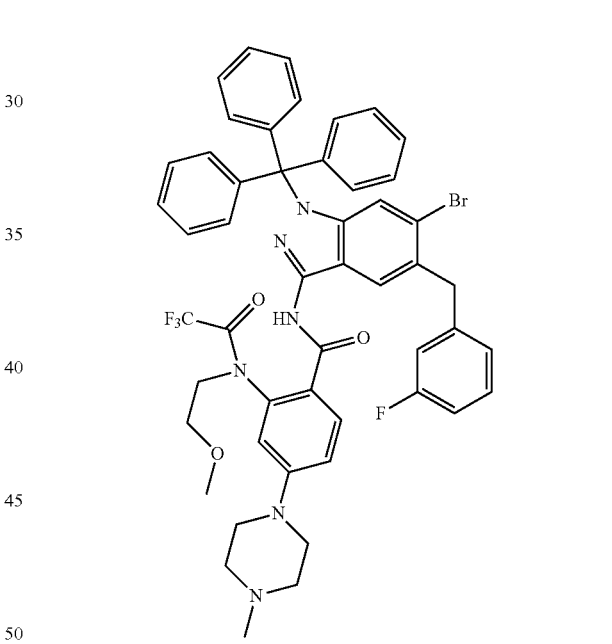

Under nitrogen atmosphere, to a solution of 6-bromo-5-[(3-fluorophenyl)methyl]-1-trityl-indazol-3-amine (1 mmol, 0.56 g) in THF (10 ml) was added DMAP (0.1 mmol, 12 mg) and DIPEA (6 mmol, 0.77 g). 2-[2-methoxyethyl-(2,2,2-trifluoroacetyl)amino]-4-(4-methylpiperazin-1-yl)benzoyl chloride (2.5 eq.) was added in portions. The resulting mixture was immediately warmed up to 50° C. and stirred for 1 h. After the reaction was completed, the mixture was partitioned between water and DCM. The organic phase was washed with NaOH solution (1M), brine and water. The resulting solution was dried over sodium sulfate and evaporated to dryness. The residue was purified by flash column chromatography with eluent AcOEt/MeOH 20:1 to afford the title compound as a white solid (120 mg, 13%).

b) Synthesis of N-[5-[(3-fluorophenyl)methyl]-6-(3-fluoro-4-hydroxyphenyl)-1-trityl-indazol-3-yl]-2-[2-methoxyethylamino]-4-(4-methylpiperazin-1-yl)benzamide [XXIII; $R_2$=$R_5$=H; Ar=3-fluorophenyl; $R_4$=3-fluoro-4-hydroxy-phenyl; P=Trityl; $R_6$=4-(4-methylpiperazin-1-yl)-2-(2-methoxyethylamino)phenyl]

c) Synthesis of N-[6-(3-fluoro-4-hydroxy-phenyl)-5-[(3-fluorophenyl)methyl]-1H-indazol-3-yl]-2-(2-methoxyethylamino)-4-(4-methylpiperazin-1-yl)benzamide [(Ia); $R_2$=$R_5$=H; Ar=3-fluorophenyl; $R_4$=3-fluoro-4-hydroxy-phenyl; $R_6$=4-(4-methylpiperazin-1-yl)-2-(2-methoxyethylamino)phenyl]

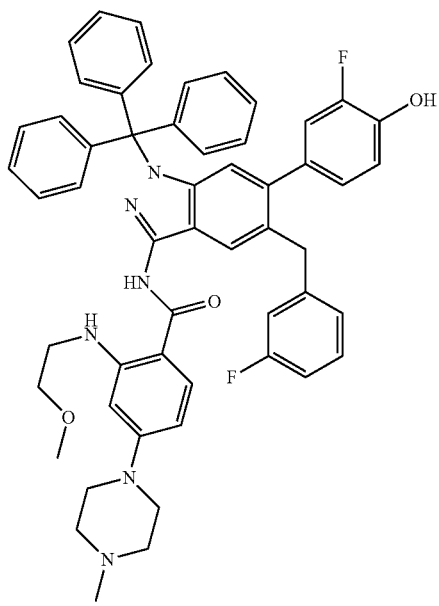 [SMILES: COCCNc1cc(N2CCN(C)CC2)ccc1C(=O)NC(=N)c1cc(Cc2cccc(F)c2)c(-c2ccc(O)c(F)c2)cc1NC(c1ccccc1)(c1ccccc1)c1ccccc1]

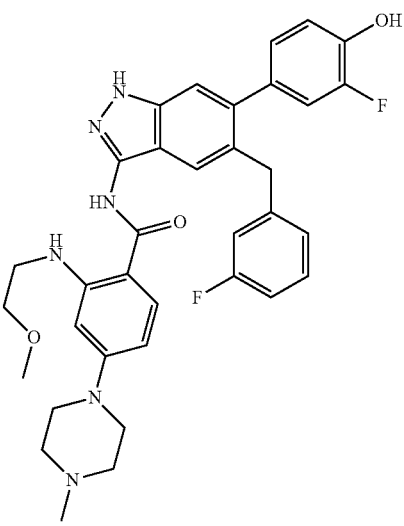 [SMILES: COCCNc1cc(N2CCN(C)CC2)ccc1C(=O)Nc1n[nH]c2cc(-c3ccc(O)c(F)c3)c(Cc3cccc(F)c3)cc12]

To a round bottom flask was added N-[6-bromo-5-[(3-fluorophenyl)methyl]-1-trityl-indazol-3-yl]-2-[2-methoxyethyl-(2,2,2-trifluoroacetyl)amino]-4-(4-methylpiperazin-1-yl)benzamide (0.13 mmol, 120 mg), cesium carbonate (0.65 mmol, 211 mg), 3-fluoro-4-hydroxyphenyl boronic acid (0.26 mmol, 36 mg) and Pd(PPh$_3$)$_4$ (0.0065 mmol, 8 mg). In another flask was prepared a degassed solution of dioxane/water 3:1 which was added to the above flask (4 ml) and stirred over 5 minutes. The mixture was stirred at 100° C. overnight under nitrogen atmosphere. The mixture was partitioned between water and DCM. The organic phase was washed with water and brine. The resulting solution was dried over sodium sulfate and evaporated to dryness. The residue was purified by flash column chromatography with eluent AcOEt/MeOH 30:1 to afford the title compound as yellow solid (68 mg, 62%).

N-[5-[(3-fluorophenyl)methyl]-6-(3-fluoro-4-hydroxy-phenyl)-1-trityl-indazol-3-yl]-2-[2-methoxyethylamino]-4-(4-methylpiperazin-1-yl)benzamide (0.08 mmol, 68 mg) was dissolved in a HCl/MeOH solution (5M, 2 ml) at 0° C. The mixture was stirred at room temperature for 3 h. The mixture was partitioned between water and DCM. The organic phase was washed with NaHCO$_3$ solution (1M), brine and water. The resulting solution was dried over sodium sulfate and evaporated to dryness. The residue was purified by flash column chromatography with eluent AcOEt/MeOH 15:1 to afford the title compound as yellow solid (20 mg, 41%).

$^1$H NMR (400 MHz, CD$_3$OD) δ 7.77 (d, J=8.8 Hz, 1H), 7.70 (s, 1H), 7.27 (s, 1H), 7.12 (m, 1H), 6.91-6.80 (m, 5H), 6.70 (m, 1H), 6.60 (m, 1H), 6.36 (m, 1H), 6.22 (s, 1H), 4.04 (s, 2H), 3.65 (m, 2H), 3.49 (m, 1H), 3.38 (m, 8H), 2.62 (m, 4H), 2.38 (s, 3H).

(ESI+) MS: m/z 627.1 (MH$^{-1}$).

Example 43 (Method D): Synthesis of 3-[3-amino-5-[(3,5-difluorophenyl)methyl]-1H-indazol-6-yl]-4-methyl-phenol [(Ic); R$_2$=R$_5$=H; Ar=3,5-difluorophenyl; R$_4$=5-hydroxy-2-methyl-phenyl]

a) Synthesis of 3-[3-amino-5-[(3,5-difluorophenyl)methyl]-1-trityl-indazol-6-yl]-4-methyl-phenol [XXXIVa; R$_2$=R$_5$=H; Ar=3,5-difluorophenyl; P=Trityl; R$_4$=2-methyl-5-hydroxy-phenyl]

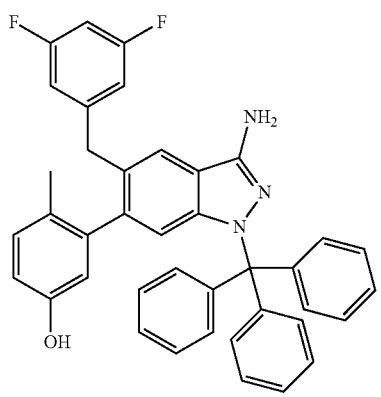 [SMILES: Cc1ccc(O)cc1-c1cc2c(cc1Cc1cc(F)cc(F)c1)c(N)nn2C(c1ccccc1)(c1ccccc1)c1ccccc1]

To a round bottom flask were added N-[6-bromo-5-[(3,5-difluorophenyl)methyl]-1-trityl-indazol-3-yl]-2,2,2-trifluoro-acetamide (0.5 mmol, 340 mg), cesium carbonate (2.5 mmol, 812 mg), boronic acid (1 mmol, 152 mg) and Pd(PPh$_3$)$_4$ (0.1 mmol, 116 mg). In another flask was prepared a degassed solution of dioxane/water 3:1 which was then added to the flask (4 ml) and stirred over 5 minutes. The mixture was reacted at 100° C. overnight under nitrogen atmosphere. The crude was diluted with DCM, washed with water, brine, dried over sodium sulfate, filtered and evaporated to dryness. The crude was purified by flash column chromatography with eluent AcOEt/MeOH 30:1 affording the title compound as white solid (160 mg, 53%).

b) Synthesis of 3-[3-amino-5-[(3,5-difluorophenyl)methyl]-1H-indazol-6-yl]-4-methyl-phenol [(Ic); R$_2$=R$_5$=H; Ar=3,5-difluorophenyl; R$_4$=2-methyl-5-hydroxy-phenyl]

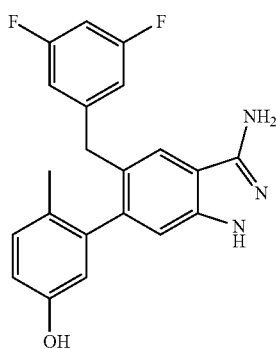 [SMILES: Cc1ccc(O)cc1-c1cc(N)c(C(=N)N)cc1Cc1cc(F)cc(F)c1]

3-[3-amino-5-[(3,5-difluorophenyl)methyl]-1-trityl-indazol-6-yl]-4-methyl-phenol (0.26 mmol, 160 mg) was cooled to 0° C. and dissolved with a 5M HCl/MeOH solution (2 ml). The mixture was stirred at room temperature over 3 h. The mixture was diluted with water and DCM, washed with NaHCO$_3$ 1M, brine, water, dried over sodium sulfate, filtered and evaporated to dryness. The residue was purified by flash column chromatography with eluent AcOEt/MeOH 10:1 to afford the title compound as yellow solid (52 mg, 55%).

$^1$H NMR (400 MHz, DMSO-d$_6$) δ 11.31 (s, 1H), 9.19 (s, 1H), 7.60 (s, 1H), 7.03 (d, J=8.4 Hz, 1H), 6.94 (tt, 1H), 6.87 (s, 1H), 6.69 (dd, J=8.4 Hz, 2.4 Hz, 1H), 6.44 (m, 3H), 5.32 (s, 2H), 3.82 (d, J=14.8 Hz, 1H), 3.66 (d, J=14.8 Hz, 1H), 1.71 (s, 3H).

(ESI+) MS: m/z 366.1 (MH$^+$).

Example 44 (Method D): synthesis of 4-[3-amino-5-[(3,5-difluorophenyl)methyl]-1H-indazol-6-yl]phenol [(Ic); R$_2$=R$_5$=H; Ar=3,5-difluorophenyl; R$_4$=4-hydroxy-phenyl]

a) Synthesis of 5-[(3,5-difluorophenyl)methyl]-2-fluoro-4-(4-hydroxyphenyl)benzonitrile [XXXIV; R$_2$=R$_5$=H; Ar=3,5-difluorophenyl; R$_4$=4-hydroxy-phenyl]

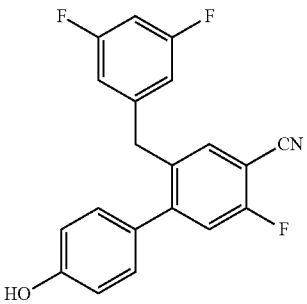 [SMILES: N#Cc1cc(Cc2cc(F)cc(F)c2)c(-c2ccc(O)cc2)cc1F]

To a microwave vial were added 4-bromo-5-(3,5-difluorobenzyl)-2-fluorobenzonitrile (0.4 mmol, 90 mg), cesium carbonate (2 mmol, 650 mg), boronic acid (0.4 mmol, 55 mg) and tetrakis(triphenylphosphine)palladium (0.02 mmol, 20 mg). The vial was sealed under argon atmosphere. In another flask was prepared a degassed solution of dioxane/water 3:1 which was added to the vial (2 ml) and stirred for 5 minutes. The mixture was reacted at 100° C. for 60 minutes under microwave irradiation. The crude was diluted with DCM, washed with water, brine, dried over sodium sulfate, filtered and evaporated to dryness.

The crude was purified by flash column chromatography with eluent Hexane/AcOEt 8:2 affording the title compound as a yellow solid (21 mg, 30%).

$^1$H NMR (400 MHz, CDCl$_3$) δ 7.85 (s, J=8.4 Hz, 1H), 7.63-6.80 (m, 5H), 6.67 (t, J=7.4 Hz, 1H), 6.49-6.27 (m, 2H), 3.95 (s, 2H).

b) Synthesis of 4-[3-amino-5-[(3,5-difluorophenyl)methyl]-1H-indazol-6-yl]phenol [(Ic); R$_2$=R$_5$=H; Ar=3,5-difluorophenyl; R$_4$=4-hydroxy-phenyl]

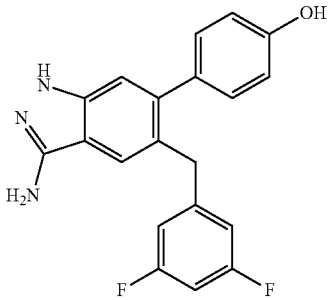

5-[(3,5-difluorophenyl)methyl]-2-fluoro-4-(4-hydroxyphenyl)benzonitrile (0.06 mmol, 21 mg) and hydrazine hydrate 50% (0.3 mmol, 600 µl) were dissolved in ethanol (600 µl). The mixture was stirred at 60° C. for 18 hours. After cooling to room temperature the solvents were removed and the crude was purified by flash column chromatography with eluent DCM/MeOH 95:5 affording the title compound as yellow solid (6 mg, 30%).

$^1$H NMR (400 MHz, CDCl$_3$) δ 8.86 (s, 1H), 7.37 (s, 1H), 7.16 (s, 1H), 7.04 (d, J=8.6 Hz, 2H), 6.82 (d, J=8.6 Hz, 2H), 6.61-6.48 (m, 1H), 6.47-6.33 (m, 2H), 4.12 (d, J=7.1 Hz, 2H), 3.95 (s, 2H).

In the same manner the following compounds can be prepared as described in Scheme 2 (Method B) using the common intermediate (XV) prepared starting from 2-[tetrahydropyran-4-yl-(2,2,2-trifluoroacetyl)amino]-4-[4-(2,2,2-trifluoroacetyl)piperazin-1-yl]benzoic acid described in WO2009013126:

| No. | Chemical Name |
|---|---|
| 45 | N-[5-[(3,5-difluorophenyl)methyl]-6-(4-hydroxyphenyl)-1H-indazol-3-yl]-4-piperazin-1-yl-2-(tetrahydropyran-4-ylamino)benzamide; |
| 46 | N-[5-[(3,5-difluorophenyl)methyl]-6-(3-hydroxyphenyl)-1H-indazol-3-yl]-4-piperazin-1-yl-2-(tetrahydropyran-4-ylamino)benzamide; |
| 47 | N-[5-[(3,5-difluorophenyl)methyl]-6-(5-hydroxy-2-methyl-phenyl)-1H-indazol-3-yl]-4-piperazin-1-yl-2-(tetrahydropyran-4-ylamino)benzamide; |
| 48 | N-[5-[(3,5-difluorophenyl)methyl]-6-(4-hydroxy-2-methyl-phenyl)-1H-indazol-3-yl]-4-piperazin-1-yl-2-(tetrahydropyran-4-ylamino)benzamide; |
| 49 | N-[5-(3-fluorophenyl)methyl]-6-(4-hydroxyphenyl)-1H-indazol-3-yl]-4-piperazin-1-yl-2-(tetrahydropyran-4-ylamino)benzamide; |
| 50 | N-[5-[(3,5-difluorophenyl)methyl]-6-(4-hydroxyphenyl)-1H-indazol-3-yl]-4-piperazin-1-yl-benzamide; |
| 51 | N-[5-[(3,5-difluorophenyl)methyl]-6-(2-oxo-1H-pyridin-4-yl)-1H-indazol-3-yl]-4-piperazin-1-yl-2-(tetrahydropyran-4-ylamino)benzamide; |
| 52 | N-[5-[(3,5-difluorophenyl)methyl]-6-[1-(2-hydroxy-1,1-dimethyl-ethyl)pyrazol-4-yl]-1H-indazol-3-yl]-4-piperazin-1-yl-2-(tetrahydropyran-4-ylamino)benzamide; |
| 53 | N-[5-[(3,5-difluorophenyl)methyl]-6-(1H-pyrazol-4-yl)-1H-indazol-3-yl]-4-piperazin-1-yl-2-(tetrahydropyran-4-ylamino)benzamide; |
| 54 | N-[5-[(3,5-difluorophenyl)methyl]-6-(2-fluoro-4-hydroxy-phenyl)-1H-indazol-3-yl]-4-piperazin-1-yl-2-(tetrahydropyran-4-ylamino)benzamide; |
| 55 | N-[5-[(3,5-difluorophenyl)methyl]-6-(4-hydroxy-2-methyl-phenyl)-1H-indazol-3-yl]-4-piperazin-1-yl-benzamide; |
| 56 | N-[5-[(3,5-difluorophenyl)methyl]-6-(1H-indazol-5-yl)-1H-indazol-3-yl]-4-piperazin-1-yl-benzamide; |
| 57 | N-[5-[(3,5-difluorophenyl)methyl]-6-(3-fluoro-5-hydroxy-phenyl)-1H-indazol-3-yl]-4-piperazin-1-yl-2-(tetrahydropyran-4-ylamino)benzamide; |
| 58 | N-[5-[(3,5-difluorophenyl)methyl]-6-(2-fluoro-5-hydroxy-phenyl)-1H-indazol-3-yl]-4-piperazin-1-yl-2-(tetrahydropyran-4-ylamino)benzamide; |
| 59 | N-[6-(2-aminopyrimidin-5-yl)-5-[(3,5-difluorophenyl)methyl]-1H-indazol-3-yl]-4-piperazin-1-yl-2-(tetrahydropyran-4-ylamino)benzamide; |
| 60 | N-[5-[(3,5-difluorophenyl)methyl]-6-(3H-imidazo[4,5-b]pyridin-6-yl)-1H-indazol-3-yl]-4-piperazin-1-yl-2-(tetrahydropyran-4-ylamino)benzamide; |
| 61 | N-[6-(5-amino-3-pyridyl)-5-[(3,5-difluorophenyl)methyl]-1H-indazol-3-yl]-4-piperazin-1-yl-2-(tetrahydropyran-4-ylamino)benzamide; |
| 62 | N-[6-(6-amino-3-pyridyl)-5-[(3,5-difluorophenyl)methyl]-1H-indazol-3-yl]-4-piperazin-1-yl-2-(tetrahydropyran-4-ylamino)benzamide; |
| 63 | N-[6-(6-amino-4-methyl-3-pyridyl)-5-[(3,5-difluorophenyl)methyl]-1H-indazol-3-yl]-4-piperazin-1-yl-2-(tetrahydropyran-4-ylamino)benzamide; |
| 64 | N-[5-[(3,5-difluorophenyl)methyl]-6-[4-(methylcarbamoyl)phenyl]-1H-indazol-3-yl]-4-piperazin-1-yl-2-(tetrahydropyran-4-ylamino)benzamide; |
| 65 | N-[5-[(3,5-difluorophenyl)methyl]-6-[3-(hydroxymethyl)phenyl]-1H-indazol-3-yl]-4-piperazin-1-yl-2-(tetrahydropyran-4-ylamino)benzamide; |
| 66 | N-[5-[(3,5-difluorophenyl)methyl]-6-[4-hydroxy-2-(trifluoromethyl)phenyl)-1H-indazol-3-yl]-4-piperazin-1-yl-2-(tetrahydropyran-4-ylamino)benzamide; |
| 67 | N-[5-[(3,5-difluorophenyl)methyl]-6-[4-hydroxy-3-methyl-phenyl)-1H-indazol-3-yl]-4-piperazin-1-yl-2-(tetrahydropyran-4-ylamino)benzamide; |
| 68 | N-[5-[(3,5-difluorophenyl)methyl]-6-(1H-pyrrolo[2,3-b]pyridin-5-yl)-1H-indazol-3-yl]-4-piperazin-1-yl-2-(tetrahydropyran-4-ylamino)benzamide; |
| 69 | N-[5-[(3,5-difluorophenyl)methyl]-6-(6-hydroxy-3-pyridyl)-1H-indazol-3-yl]-4-piperazin-1-yl-2-(tetrahydropyran-4-ylamino)benzamide; |
| 70 | N-[5-[(3,5-difluorophenyl)methyl]-6-phenyl-1H-indazol-3-yl]-4-piperazin-1-yl-2-(tetrahydropyran-4-ylamino)benzamide; |

-continued

| No. | Chemical Name |
|---|---|
| 71 | N-[5-[(3,5-difluorophenyl)methyl]-6-(3-methoxyphenyl)-1H-indazol-3-yl]-4-piperazin-1-yl-2-(tetrahydropyran-4-ylamino)benzamide; |
| 72 | N-[5-[(3,5-difluorophenyl)methyl]-6-(3-fluoro-4-hydroxy-phenyl)-1H-indazol-3-yl]-4-piperazin-1-yl-2-(tetrahydropyran-4-ylamino)benzamide; |
| 73 | N-[5-[(3,5-difluorophenyl)methyl]-6-(1H-indazol-5-yl)-1H-indazol-3-yl]-4-piperazin-1-yl-2-(tetrahydropyran-4-ylamino)benzamide; |
| 74 | N-[5-[(3,5-difluorophenyl)methyl]-6-pyrimidin-5-yl-1H-indazol-3-yl]-4-piperazin-1-yl-2-(tetrahydropyran-4-ylamino)benzamide; |
| 75 | N-[5-[(3,5-difluorophenyl)methyl]-6-(3-oxoisoindolin-5-yl)-1H-indazol-3-yl]-4-piperazin-1-yl-2-(tetrahydropyran-4-ylamino)benzamide; |
| 76 | N-[6-(2-aminopyrimidin-5-yl)-5-[(3,5-difluorophenyl)methyl]-1H-indazol-3-yl]-4-piperazin-1-yl-benzamide; |
| 77 | N-[6-(3-fluoro-4-hydroxy-phenyl)-5-[(3-fluorophenyl)methyl]-1H-indazol-3-yl]-2-(2-methoxyethylamino)-4-piperazin-1-yl-benzamide; |
| 78 | N-[6-[2-(3-hydroxyphenyl)ethynyl]-1H-indazol-3-yl]-4-piperazin-1-yl-2-(tetrahydropyran-4-ylamino)benzamide; |
| 79 | N-[5-[(3,5-difluorophenyl)methyl]-6-(4-pyridyl)-1H-indazol-3-yl]-4-piperazin-1-yl-2-(tetrahydropyran-4-ylamino)benzamide; |
| 80 | N-[5-[(3,5-difluorophenyl)methyl]-6-(3-pyridyl)-1H-indazol-3-yl]-4-piperazin-1-yl-2-(tetrahydropyran-4-ylamino)benzamide; |
| 81 | N-[6-(3-fluoro-4-hydroxy-phenyl)-5-[(3-fluorophenyl)methyl]-1H-indazol-3-yl]-4-piperazin-1-yl-2-(tetrahydropyran-4-ylamino)benzamide; |
| 82 | N-[6-(2-fluoro-4-hydroxy-phenyl)-5-[(3-fluorophenyl)methyl]-1H-indazol-3-yl]-4-piperazin-1-yl-2-(tetrahydropyran-4-ylamino)benzamide; |
| 83 | N-[5-[(3,5-difluorophenyl)methyl]-6-[4-(1-hydroxy-1-methyl-ethyl)phenyl]-1H-indazol-3-yl]-4-piperazin-1-yl-2-(tetrahydropyran-4-ylamino)benzamide; |
| 84 | N-[5-[(3,5-difluorophenyl)methyl]-6-(4-hydroxy-3-methyl-phenyl)-1H-indazol-3-yl]-4-piperazin-1-yl-benzamide; |
| 85 | N-[6-(2-aminopyrimidin-5-yl)-5-[(3-fluorophenyl)methyl]-1H-indazol-3-yl]-4-piperazin-1-yl-benzamide; |

Pharmacology

Compounds of the present invention were tested in cellular assays to evaluate kinase inhibitory activity as described below.

Inhibition of the Proliferation of ALK Positive Cells

Method: Tritiated Thymidine Uptake Cell Proliferation Assay

The following procedure was used with parent untransformed BaF3 cells, BaF3 cells transformed with the oncogenic fusion protein NPM/ALK, NPM/ALK positive SUDHL-1 cells, NPM/ALK positive SUPM2, ALK-negative HL60 cells, NPM/ALK positive KARPAS-299 cells. The parent untransformed BaF3 cells or Alk-negative HL60 cells are used as controls. Cells were seeded in U-bottomed 96-well plates at 10000 cells/well in a volume of 100 µl in supplemented medium. In the case of the parent untransformed BaF3 cells, the medium was supplemented with IL-3. Serial dilutions of inhibitors were added to the appropriate wells and volumes adjusted to 200 µl. Controls were treated with the equivalent volume of vehicle, DMSO, alone. Plates were incubated at 37° C. for 72 h. 3[H]-thymidine (1 µCi/well) was added for the last 16 h of incubation. Cells were harvested on to paper filters and 3[H]-thymidine incorporation was measured using a scintillation counter (1430 MicroBeta, Wallac, Turku, Finland). The 50% inhibitory concentration ($IC_{50}$) was defined as the concentration of inhibitor, expressed in nanomolar units, that gave a 50% decrease in 3[H]-thymidine uptake compared with controls.

Potentially toxic effects were assessed using parent untransformed BaF3 cells or ALK negative HL60 cells.

In Table 1 are listed results for selected examples of compounds of the invention, reported as percentage of inhibition of cell proliferation at 200 nM, obtained from cellular assays in Karpas 299 lymphoma cell line positive for the oncogenic fusion protein NPM-ALK.

TABLE 1

| % Inhibition Karpas 299 cells | Example |
|---|---|
| 99 | 4 |
| 100 | 5 |
| 100 | 6 |
| 93 | 7 |
| 99 | 8 |
| 100 | 9 |
| 93 | 10 |
| 95 | 11 |
| 100 | 12 |
| 62 | 14 |
| 100 | 15 |
| 88 | 16 |
| 100 | 18 |
| 99 | 19 |
| 100 | 38 |
| 100 | 33 |
| 100 | 34 |
| 100 | 35 |
| 100 | 42 |
| 100 | 21 |
| 100 | 29 |
| 71 | 23 |
| 100 | 25 |
| 99 | 26 |
| 87 | 27 |
| 55 | 28 |
| 93 | 3 |

In Table 2 are listed results for selected examples of compounds of the invention, reported as percentage of inhibition of cell proliferation at 200 nM, obtained from cellular assays in BaF3 cell line transfected with the oncogenic fusion protein NPM-ALK and expressing the mutation L1196M.

TABLE 2

| % Inhibition BaF3 NPM-ALK L1196M cells | Example |
| --- | --- |
| 99 | 4 |
| 100 | 5 |
| 100 | 6 |
| 100 | 7 |
| 99 | 8 |
| 99 | 9 |
| 61 | 10 |
| 88 | 11 |
| 99 | 12 |
| 97 | 13 |
| 66 | 14 |
| 100 | 15 |
| 97 | 18 |
| 100 | 19 |
| 57 | 20 |
| 100 | 38 |
| 99 | 33 |
| 100 | 34 |
| 96 | 35 |
| 93 | 42 |
| 99 | 21 |
| 98 | 29 |
| 61 | 23 |
| 52 | 24 |
| 100 | 25 |
| 99 | 26 |
| 62 | 27 |
| 60 | 28 |
| 83 | 3 |

In Table 3 are listed averaged IC$_{50}$ values of cell proliferation inhibition for selected examples of compounds of the present invention, obtained from cellular assays in BaF3 cell line transfected with the oncogenic fusion protein NPM-ALK and expressing the mutation L1196M. The letter "A" designates an IC$_{50}$ value between 1 nM and 50 nM, the letter "B" designates an IC$_{50}$ value between 50 nM and 100 nM, the letter "C" designates an IC$_{50}$ value between 100 and 500 nM.

TABLE 3

| IC$_{50}$ BaF3 NPM-ALK L1196M cells | Example |
| --- | --- |
| A | 4 |
| A | 5 |
| A | 6 |
| A | 7 |
| A | 8 |
| A | 9 |
| A | 38 |
| A | 33 |
| A | 34 |
| A | 21 |
| B | 29 |
| A | 25 |
| A | 26 |
| A | 3 |
| B | 11 |
| B | 12 |
| C | 13 |
| B | 15 |
| C | 18 |
| B | 19 |
| B | 35 |
| B | 42 |

In Table 4 are reported the IC$_{50}$ of cellular proliferation assays of example 3 versus ALK positive, mutated and negative cell lines.

TABLE 4

| Cell line | Example 3 (nM) |
| --- | --- |
| BaF3 NPM-ALK L1196M | 6 |
| BaF3 NPM-ALK L1152R | 18 |
| BaF3 NPM-ALK C1156Y | 34 |
| BaF3 NPM-ALK WT | 18 |
| Karpas299 | 23 |
| SUPM2 | 52 |
| SUDHL1 | 36 |
| HL60 | 17000 |

Biochemical Assay

A proprietary radiometric protein kinase assay (33Pan-Quinase® Activity Assay) developed by ProQuinase GmbH (Freiburg, Germany) was used for measuring the kinase activity of selected protein kinases. All assays were performed in FlashPlates™ wells 96 Perkin Elmer (Boston, Mass., USA) in a reaction volume of 50 µl. The reaction mixture was obtained in 4 steps in the following order:
1. 10 µl of a solution of non-radioactive ATP in water;
2. 25 µl of assay buffer/[γ-$^{33}$P]-ATP mixture
3. 5 µl of test sample in 10% DMSO
4. 10 µl of enzyme/substrate mixture The assay for all protein kinases contained 70 mM HEPES-NaOH pH 7.5, 3 mM MgCl$_2$, 3 mM MnCl$_2$, 3 µM Na-orthovanadate, 1.2 mM DTT, ATP (variable amounts, corresponding to the apparent ATP-K$_m$ of the respective kinase), [γ-$^{33}$P]-ATP (approx. 8×10$^5$ cpm per well), protein kinase (variable amounts), and substrate (variable amounts).

Compounds of formula (I) have been tested against a panel of protein kinases for the determination of IC$_{50}$ values by testing 10 concentrations of compound in the range from 5×10-06 M to 1.5×10-10 M in singlicate in each kinase assay. All protein kinases provided by ProQinase were expressed in Sf9 insect cells or in *E. coli* as recombinant GST-fusion proteins or His-tagged proteins, either as full-length or enzymatically active fragments. All kinases were produced from human cDNAs and purified by either GSH-affinity chromatography or immobilized metal. Affinity tags were removed from a number of kinases during purification. The purity of the protein kinases was examined by SDS-PAGE/Coomassie staining, the identity was checked by mass spectroscopy. Kinases from external vendors (CAR=Carna Biosciences Inc.; INV=Life Technologies (Invitrogen Corporation); MIL=Merck-Millipore (Millipore Corporation), were expressed, purified and quality-controlled by virtue of the vendors readings.

Typical Procedure:

A stock solution of compound of formula (I) was diluted to 5×10-04M/100% DMSO. In the process, the compound was serially diluted in semi-log steps with 100% DMSO in a 96 well microtiter plate. The concentration range of serial dilution was 5×10-04 M to 1.5×10-08 M. Directly before use the test compound was further diluted 1:10 with water, resulting in a concentration range from 5×10-05 M to 1.5×10-09 M in 10% DMSO. For the assays 5 µl from each concentration were transferred into the assay. The final volume of the assay was 50 µl. The compound was tested at 10 final assay concentrations in the range from 5×10-06 M to 1.5×10-10 M. The final DMSO concentration in the reaction cocktails was 1% in all cases. The reaction cocktails were incubated at 30° C. for 60 minutes. The reaction was stopped with 50 µl of 2% (v/v) H3PO4, plates were aspirated and washed two times with 200 µl 0.9% (w/v) NaCl. Incorporation of 33Pi (counting of "cpm") was determined with a microplate scintillation counter (Microbeta, Wallac).

All assays were performed with a BeckmanCoulter Biomek 2000/SL robotic system. The kinases and substrates with their concentrations used in the assays are listed in Table 5.

TABLE 5

| Kinase Name | Kinase conc. ng/50 µl | Kinase conc. nM* | ATP conc. µM | Substrate Name | Substrate conc. µg/50 ml |
|---|---|---|---|---|---|
| ALK F1174L (GST-His-tag) | 25 | 7.1 | 0.3 | Poli(Glu, Tyr)4:1 | 0.125 |
| ALK L1196M (GST-His-tag) | 30 | 8.5 | 0.3 | Poli(Glu, Tyr)4:1 | 0.125 |
| ALK wt (GST-His-tag) | 10 | 2.8 | 0.3 | Poli(Glu, Tyr)4:1 | 0.125 |
| DDR2 T654M | 100 | 25.7 | 0.3 | RBER-NTRK3tide | 2.0 |
| DDR2 wt | 50 | 12.9 | 1.0 | RBER-NTRK3tide | 2.0 |
| EPHB2 | 50 | 12.6 | 0.3 | Poli(Ala, Glu, Lys, Tyr)6:2:5:1 | 0.125 |
| FYN | 10 | 2.2 | 0.3 | Poli(Glu, Tyr)4:1 | 0.125 |
| RET M918T | 40 | 9.9 | 0.3 | Poli(Glu, Tyr)4:1 | 0.125 |
| RET V804M | 25 | 6.2 | 0.3 | Poli(Glu, Tyr)4:1 | 0.125 |
| RET wt | 40 | 9.9 | 1.0 | Poli(Glu, Tyr)4:1 | 0.125 |
| ROS | 5 | 1.3 | 0.3 | Poli(Ala, Glu, Lys, Tyr)6:2:5:1 | 0.125 |
| TRK-B | 10 | 3.0 | 0.3 | Poli(Glu, Tyr)4:1 | 0.25 |

*Maximal molar enzyme assay concentrations, implying enzyme preparations exclusively containing 100% active enzyme For each kinase, the median value of the cpm of three wells with complete reaction cocktails, but without kinase, was defined as "low control" (n=3). This value reflects unspecific binding of radioactivity to the plate in the absence of protein kinase but in the presence of the substrate. Additionally, for each kinase the median value of the cpm of three other wells with the complete reaction cocktail, but without any compound, was taken as the "high control", i.e. full activity in the absence of any inhibitor (n=3). The difference between high and low control was taken as 100% activity for each kinase. As part of the data evaluation the low control value of each kinase was subtracted from the high control value as well as from their corresponding "compound values". The residual activity (in %) for each compound well was calculated by using the following formula:

Res. Activity (%)=100×[(cpm of compound−low control)/(high control−low control)]

Since 10 distinct concentrations of each compound were tested against each kinase, the evaluation of the raw data resulted in 10 values for residual activities per kinase. Based on each 10 corresponding residual activities, $IC_{50}$ values were calculated using Prism 5.04 for Windows (Graphpad, San Diego, Calif.). The mathematical model used was "Sigmoidal response (variable slope)" with parameters "top" fixed at 100% and "bottom" at 0%. The fitting method used was a least-squares fit.

In Table 6 are reported $IC_{50}$ values for the example 3 in 12 wild-type and mutated protein kinases assays.

TABLE 6

| Kinase Name | $IC_{50}$ (nM) |
|---|---|
| ALK F1174L (GST-His-tag) | 46 |
| ALKL1196M (GST-His-tag) | 45 |
| ALK wild-type (GST-His-tag) | 29 |
| DDR2 T654M | 84 |
| DDR2 wild-type | 150 |

TABLE 6-continued

| Kinase Name | $IC_{50}$ (nM) |
|---|---|
| EPHB2 | 90 |
| FYN | 34 |
| RET M918T | 120 |
| RET V804M | 85 |
| RET wild-type | 120 |
| ROS | 160 |
| TRK-B | 88 |

The invention claimed is:

1. Compounds of general formula (I):

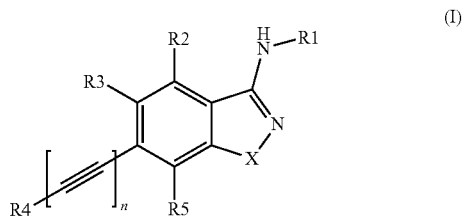

in which:
X is —NH— or —O—;
$R_1$ is hydrogen or —$COR_6$;
$R_2$ and $R_5$ are independently selected from hydrogen, halogen and $C_1$-$C_6$ alkyl;
$R_3$ is —Y—Ar where Y is a divalent group selected from —$CH_2$—, —NH—, —O—, —S—, —S(O)—, and —$S(O)_2$—;
Ar is an aryl, or a 5-10 membered heteroaryl, where said aryl or heteroaryl is optionally substituted by one to three groups independently selected from halogen, $C_1$-$C_6$ alkyl, $C_1$-$C_6$ haloalkyl, $C_1$-$C_6$ hydroxyalkyl, $C_1$-$C_6$ haloalkoxy, $C_1$-$C_6$ halothioalkoxy, cyano, hydroxyl, mercapto, amino, $C_1$-$C_6$ alkoxy, $C_1$-$C_6$ thioalkoxy, $C_1$-$C_6$ mono alkylamino, $C_1$-$C_6$ bis alkylamino, carbamoyl, N—($C_1$-$C_6$ alkyl) carbamoyl, N,N-bis ($C_1$-$C_6$ alkyl)carbamoyl, $C_1$-$C_6$ acylamino, N—($C_1$-$C_6$ alkyl)-N—($C_1$-$C_6$ acyl) amino, N—($C_1$-$C_6$ alkyl)sulfonylamino and N,N-bis ($C_1$-$C_6$ alkyl)sulfonylamino;
$R_4$ is selected from the group consisting of:
aryl optionally substituted by one to three substituents independently selected from hydroxyl, amino, —OC(O)$NHR_e$, —$OR_e$, —NHC(O)$NHR_e$, halogen, cyano, carbamoyl, $C_1$-$C_6$ alkyl, $C_1$-$C_6$ hydroxyalkyl, $C_1$-$C_6$ haloalkyl, $C_1$-$C_6$ haloalkoxy, $C_1$-$C_3$ alkoxy, —$OCH_2CH_2R_e$, —$OCH_2C(O)NHR_e$, —$OCH_2CH_2OR_e$, —$OCH_2CH_2NHR_e$, —$CH_2C(O)NHR_e$, N—($C_1$-$C_6$ alkyl)carbamoyl, N—($C_3$-$C_6$ cycloalkyl)carbamoyl, $C_1$-$C_6$ acylamino, $C_1$-$C_6$ alkylsulfonylamino, aminosulfonyl, N—($C_1$-$C_6$ alkyl) aminosulfonyl, and $C_1$-$C_6$ alkylsulfonyl being $R_e$ an aryl optionally substituted by one or two substituents independently selected from $C_1$-$C_6$ haloalkyl and $CH_2$-A, where A is an heterocyclyl selected among pyrrolidinyl, piperidinyl, piperazinyl and morpholinyl, and said heterocyclyl being optionally substituted by a $C_1$-$C_3$-alkyl group;
5-10 membered heteroaryl optionally substituted on the carbon atoms with one or two groups independently selected from amino, $C_1$-$C_6$ acylamino, oxo, hydroxyl, halogen, $C_1$-$C_6$ alkylsulfonyl, $C_1$-$C_6$ alkylsulfonylamino, aminosulfonyl, N—($C_1$-$C_6$ alkyl)aminosulfonyl, cyano, $C_1$-$C_6$ alkyl, $C_1$-$C_6$ haloalkyl, $C_1$-$C_3$ alkoxy, $C_1$-$C_6$ hydroxyalkyl, carbamoyl, N—($C_1$-$C_6$ alkyl)carbamoyl and N—($C_3$-$C_6$ cycloalkyl)carbamoyl;

$R_6$ is aryl substituted by $R_7$ and $R_8$;

$R_7$ is selected from the group consisting of hydrogen, —$OR_f$ and —$NR_fR_g$, where $R_f$ and $R_g$ are independently selected from hydrogen, $C_1$-$C_6$ alkyl, $C_2$-$C_6$ alkyl optionally substituted by amino, $C_1$-$C_3$ mono alkylamino, $C_1$-$C_3$ bis alkylamino, hydroxy or $C_1$-$C_3$ alkoxy, $C_3$-$C_7$ cycloalkyl and heterocyclyl groups from 4 to 7 atoms containing up to 2 heteroatoms selected from oxygen, sulfur and nitrogen, in which those $C_3$-$C_7$ cycloalkyl and heterocyclyl are optionally substituted by one or two substituents independently selected from halogen, $C_1$-$C_6$ alkyl, $C_1$-$C_6$ haloalkyl, $C_1$-$C_6$ haloalkoxy, halothioalkoxy, nitro, cyano, hydroxy, $C_1$-$C_6$ alkoxy, mercapto, amino, $C_1$-$C_6$ alkylthio, $C_1$-$C_6$ mono alkylamino, $C_1$-$C_6$ bis alkylamino, $C_1$-$C_6$ acylamino, N—($C_1$-$C_6$ alkyl)-N—($C_1$-$C_6$ acyl)amino, $C_1$-$C_6$ alkyl sulfonylamino, N—($C_1$-$C_6$ alkyl)-N—($C_1$-$C_6$ alkyl)sulfonylamino, N—($C_1$-$C_6$ alkyl)carbamoyl; N—($C_3$-$C_7$ cycloalkyl) carbamoyl and heterocyclyl groups from 4 to 7 atoms containing up to 2 heteroatoms selected from oxygen, sulfur and nitrogen;

$R_8$ is selected from the group consisting of hydrogen, —$OR_c$, —$NR_cR_d$ and 5-10 membered heteroaryl or heterocyclyl groups from 4 to 7 atoms containing up to 2 heteroatoms selected from oxygen, sulfur and nitrogen and optionally substituted by a substituent selected from halogen, $C_1$-$C_6$ alkyl, $C_1$-$C_6$ haloalkyl, $C_1$-$C_6$ haloalkoxy, $C_1$-$C_6$ halothioalkoxy, nitro, cyano, hydroxy, $C_1$-$C_6$ alkoxy, mercapto, $C_1$-$C_6$ alkylthio, amino, $C_1$-$C_6$ mono alkylamino, $C_1$-$C_6$ bis alkylamino, $C_1$-$C_6$ acylamino, N—($C_1$-$C_6$ alkyl)-N—($C_1$-$C_6$ acyl)amino, $C_1$-$C_6$ alkylsulfonylamino, N—($C_1$-$C_6$ alkyl)-N—($C_1$-$C_6$ alkyl)sulfonylamino, (N,N-bis($C_1$-$C_6$ alkyl)carbamoyl)$C_1$-$C_6$ alkyl and heterocyclyl groups from 4 to 7 atoms containing up to two heteroatoms selected from oxygen, sulfur and nitrogen;

$R_c$ and $R_d$ are independently selected from hydrogen, $C_1$-$C_6$ alkyl, $C_2$-$C_6$ alkyl optionally substituted by amino, $C_1$-$C_3$ mono alkylamino, $C_1$-$C_3$ bis alkylamino, hydroxyl, and $C_1$-$C_3$ alkoxy;

n is 0;

their N-oxides, pharmaceutically acceptable salts, enantiomers, stereoisomers, atropisomers, rotamers, tautomers, diastereomers, or racemates.

2. Compounds according to claim 1 in which X is —NH—.

3. Compounds of general formula (I)

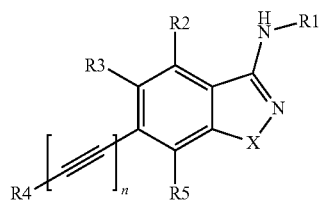

(I)

wherein:

X is —NH—;

n is 0;

$R_1$ is hydrogen or —CO—$R_6$;

$R_2$ and $R_5$ are independently selected in the group consisting of hydrogen, halogen and $C_1$-$C_6$ alkyl;

$R_3$ is —Y—Ar where Y is the bivalent group —$CH_2$—;

Ar is phenyl or naphthyl, optionally substituted by one to three groups selected independently in the group consisting of halogen, $C_1$-$C_6$ alkyl, $C_1$-$C_6$ haloalkyl, cyano, carbamoyl, N—($C_1$-$C_6$ alkyl)carbamoyl, and N,N-bis ($C_1$-$C_6$ alkyl)carbamoyl;

$R_4$ is selected from the group consisting of:
phenyl or naphthyl optionally substituted by one to three substituents independently selected among hydroxyl, $C_1$-$C_3$ alkoxy, amino, —OC(O)$NHR_e$, —$OR_e$, —NHC(O)$NHR_e$, halogen, cyano, $C_1$-$C_6$ hydroxyalkyl, $C_1$-$C_6$ haloalkyl, $C_1$-$C_6$ alkyl, $C_1$-$C_6$ haloalkoxy, —$OCH_2CH_2R_e$, —$OCH_2C(O)NHR_e$, —$OCH_2CH_2OR_e$, —$CH_2CH_2OR_e$— $OCH_2CH_2NHR_e$, —$CH_2C(O)NHR_e$, N—($C_1$-$C_6$ alkyl)carbamoyl, N—($C_3$-$C_6$ cycloalkyl)carbamoyl, $C_1$-$C_6$ acylamino, $C_1$-$C_6$ alkylsulfonylamino, $C_1$-$C_6$ alkylsulfonyl, N—($C_1$-$C_6$ alkyl)aminosulfonyl, and aminosulfonyl, being $R_e$ a phenyl optionally substituted by one or two substituents independently selected among trifluoromethyl and $CH_2$-A, wherein A is an heterocyclyl selected among pyrrolidinyl, piperidinyl, piperazinyl and morpholinyl, and said heterocyclyl being optionally substituted by a $C_1$-$C_3$-alkyl group;

5-10 membered heteroaryl selected from pyridyl, pyrimidinyl, pyridazinyl, pyrazinyl, triazinyl, benzopyrazolyl, benzo-imidazolyl, indolyl, isoindolyl, pyrazolyl, indazolyl, imidazo-pyridinyl, pyrrolopyridinyl, thiazolyl, benzo-oxazolyl, and benzoisoxazolyl, optionally substituted at the carbon atoms with one or two groups independently selected from amino, $C_1$-$C_6$ acylamino, oxo, hydroxyl, cyano, $C_1$-$C_3$ alkoxy, halogen, $C_1$-$C_6$ alkylsulfonyl, N—($C_1$-$C_6$ alkyl)aminosulfonyl, $C_1$-$C_6$ alkylsulfonylamino, aminosulfonyl, $C_1$-$C_6$ alkyl, $C_1$-$C_6$ haloalkyl, $C_1$-$C_6$ hydroxyalkyl, carbamoyl, N—($C_1$-$C_6$ alkyl)carbamoyl and N—($C_3$-$C_6$ cycloalkyl)carbamoyl;

$R_6$ is phenyl or naphthyl;

$R_7$ is selected among hydrogen, —$NR_fR_g$ where $R_f$ is hydrogen and $R_g$ is selected from $C_3$-$C_7$ cycloalkyl, heterocyclyl and $C_2$-$C_6$ alkyl optionally substituted by $C_1$-$C_3$ alkoxy; or $R_7$ is a group selected among:

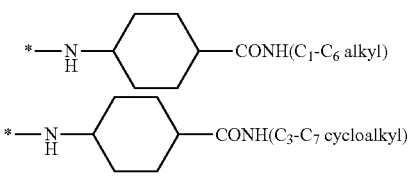

with cis or trans configuration and where the asterisk * indicates the bond of those groups with $R_6$;

$R_8$ is hydrogen or a heterocyclyl selected among pyrrolidinyl, piperidinyl, piperazinyl, and morpholinyl, optionally substituted by $C_1$-$C_3$-alkyl.

4. Compounds according to claim 3, wherein:
n is 0;
$R_1$ is —CO—$R_6$;
$R_3$ is —CH$_2$Ar, where Ar is phenyl substituted by one or two groups independently selected from halogen, $C_1$-$C_6$ alkyl, $C_1$-$C_6$ haloalkyl, cyano, carbamoyl, N—($C_1$-$C_6$ alkyl)carbamoyl, and N,N-bis($C_1$-$C_6$ alkyl)carbamoyl;
$R_4$ is phenyl optionally substituted by one or two substituents selected from hydroxyl, $C_1$-$C_3$ alkoxy, amino, —OC(O)NHR$_e$, —OR$_e$, —NHC(O)NHR$_e$, halogen, cyano, $C_1$-$C_6$ haloalkyl, $C_1$-$C_6$ alkyl, $C_1$-$C_6$ hydroxyalkyl, $C_1$-$C_6$ haloalkoxy, —OCH$_2$CH$_2$R$_e$, —OCH$_2$C(O)NHR$_e$, —CH$_2$CH$_2$OR$_e$, —OCH$_2$CH$_2$OR$_e$, —OCH$_2$CH$_2$NHR$_e$, —CH$_2$C(O)NHR$_e$, N—($C_1$-$C_6$ alkyl)carbamoyl, N—($C_3$-$C_6$ cycloalkyl)carbamoyl, $C_1$-$C_6$ acylamino, $C_1$-$C_6$ alkylsulfonylamino, and aminosulfonyl, being R$_e$ a phenyl optionally substituted by one or two substituents independently selected among trifluoromethyl and CH$_2$-A, wherein A is an heterocyclyl selected among pyrrolidinyl, piperidinyl, piperazinyl and morpholinyl, and said heterocyclyl being optionally substituted by a $C_1$-$C_3$-alkyl group;
$R_6$ is phenyl substituted by $R_7$ and $R_8$.

5. Compounds according to claim 3, wherein
n is 0;
$R_1$ is —CO—$R_6$;
$R_3$ is —CH$_2$Ar, where Ar is phenyl substituted by one or two groups independently selected from halogen, $C_1$-$C_6$ alkyl, $C_1$-$C_6$ haloalkyl, cyano, carbamoyl, N—($C_1$-$C_6$ alkyl)carbamoyl, and N,N-bis($C_1$-$C_6$ alkyl)carbamoyl;
$R_4$ is heteroaryl selected from pyridyl, pyrimidinyl, pyrazolyl, imidazo[4,5-b]pyridinyl, indazolyl, isoindolyl, and pyrrolo[2,3-b]pyridinyl, which are optionally substituted on the carbon atoms by one or two substituents independently selected from $C_1$-$C_6$ alkyl, $C_1$-$C_6$ haloalkyl, cyano, carbamoyl, $C_1$-$C_6$ hydroxyalkyl, $C_1$-$C_3$ alkoxy, amino, oxo and hydroxyl;
$R_6$ is phenyl substituted by $R_7$ and $R_8$.

6. Compounds according to claim 4, wherein
$R_1$ is —CO—$R_6$ where $R_6$ is phenyl substituted in position 2 and 4, respectively, by group $R_7$ and $R_8$;
$R_2$ and $R_5$ are hydrogen;
$R_3$ is —CH$_2$Ar, where Ar is phenyl substituted by one or two substituents independently selected from fluoro, chloro, trifluoromethyl, methyl, cyano, and carbamoyl;
$R_4$ is phenyl substituted by one or two substituents independently selected from trifluoromethyl, hydroxyl, halogen, $C_1$-$C_3$-alkoxy, cyano, $C_1$-$C_6$ hydroxyalkyl, amino, $C_1$-$C_6$ alkyl, N—($C_1$-$C_6$ alkyl)carbamoyl, —OC(O)NHR$_e$, —OR$_e$, —NHC(O)NHR$_e$, —OCH$_2$CH$_2$R$_e$, —OCH$_2$C(O)NHR$_e$, —OCH$_2$CH$_2$OR$_e$, —OCH$_2$CH$_2$NHR$_e$, and —CH$_2$C(O)NHR$_e$, being R$_e$ a trifluoromethylphenyl group.

7. Compounds of general formula (I)

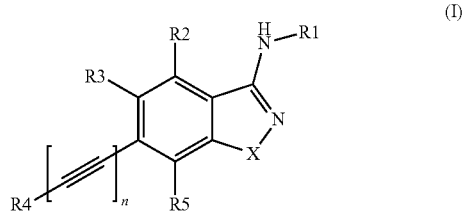

(I)

wherein
X is —NH—;
n is 0;
$R_1$ is —CO—$R_6$ where $R_6$ is phenyl substituted in position 2 and 4, respectively, by group $R_7$ and $R_8$;
$R_2$ and $R_5$ are hydrogen;
$R_3$ is —CH$_2$Ar, where Ar is selected among 3,5-difluorophenyl, 3-fluorophenyl, 3-chlorophenyl, 3-bromophenyl, 2,4-difluorophenyl, 2,5-difluorophenyl, 2,6-difluorophenyl, 3,5-dimethylphenyl, 3,5 dichlorophenyl, 2,5-dichlorophenyl, 2,6-dichlorophenyl, 5-cyano-3-fluorophenyl, 3-cyano-6-fluorophenyl and 2-cyano-5-fluorophenyl;
$R_4$ is phenyl substituted by one or two groups selected from trifluoromethyl, fluoro, hydroxyl, methyl, hydroxymethyl, 1-hydroxy-1-methylethyl, methoxy, and N-methylcarbamoyl;
$R_7$ is —NHR$_g$ where R$_g$ is selected among tetrahydropyranyl, 2-methoxyethyl and piperidinyl, or $R_7$ is a group selected between:

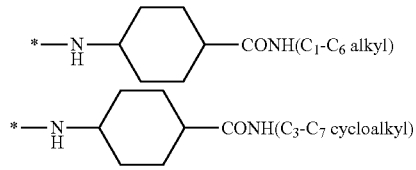

with cis or trans configuration and where the asterisk * indicates the bond of those groups with $R_6$;
$R_8$ is a piperazinyl or 4-methyl-piperazinyl.

8. Compounds according to claim 7, wherein
$R_1$ is —CO—$R_6$ where $R_6$ is phenyl substituted in position 2 by 4-tetrahydropyranylamino group or by 2-methoxyethylamino group and in position 4 by a 4-methyl-1-piperazinyl group;
$R_4$ is phenyl substituted with two hydroxyl groups, with one fluorine and one hydroxyl group, or with one methyl and one hydroxyl group or with one trifluoromethyl and one hydroxyl group.

9. Compounds according to claim 3, wherein:
n is 0;
$R_1$ is hydrogen;
$R_3$ is —CH$_2$Ar, where Ar is a phenyl substituted by one or two substituents selected among fluoro, chloro, trifluoromethyl, methyl, cyano, and carbamoyl;
$R_4$ is a phenyl substituted by one or two substituents independently selected among $C_1$-$C_6$ alkyl, $C_1$-$C_6$ haloalkyl, and hydroxyl.

10. Compounds according to claim 9, wherein:
$R_2$ and $R_5$ are hydrogen;
$R_3$ is —CH$_2$Ar, where Ar is a group 3,5-difluorophenyl, 3-fluorophenyl, 2,4-difluorophenyl, 2,5-difluorophenyl, 2,6-difluorophenyl, 3,5-dimethylphenyl, 3,5-dichlorophenyl, 2,5-dichlorophenyl, 2,6-dichlorophenyl, 5-cyano-3-fluorophenyl, 3-cyano-6-fluorophenyl, and 2-cyano-5-fluorophenyl;
$R_4$ is phenyl substituted in position 3 or 4 by hydroxyl or by hydroxyl and methyl.

11. A compound according to claim 1, selected from:
N-[5-[(3,5-difluorophenyl)methyl]-6-(4-hydroxyphenyl)-1H-indazol-3-yl]-4-(4-methylpiperazin-1-yl)-2-(tetrahydropyran-4-ylamino)benzamide;

N-[5-[(3,5-difluorophenyl)methyl]-6-(3-hydroxyphenyl)-1H-indazol-3-yl]-4-(4-methylpiperazin-1-yl)-2-(tetrahydropyran-4-ylamino)benzamide;

N-[5-[(3,5-difluorophenyl)methyl]-6-(4-hydroxy-2-methyl-phenyl)-1H-indazol-3-yl]-4-(4-methylpiperazin-1-yl)-2-(tetrahydropyran-4-ylamino)benzamide;

N-[5-[(3,5-difluorophenyl)methyl]-6-(2-fluoro-4-hydroxy-phenyl)-1H-indazol-3-yl]-4-(4-methylpiperazin-1-yl)-2-(tetrahydropyran-4-ylamino)benzamide;

N-[5-[(3,5-difluorophenyl)methyl]-6-(5-hydroxy-2-methyl-phenyl)-1H-indazol-3-yl]-4-(4-methylpiperazin-1-yl)-2-(tetrahydropyran-4-ylamino)benzamide;

N-[5-[(3,5-difluorophenyl)methyl]-6-(2-fluoro-5-hydroxy-phenyl)-1H-indazol-3-yl]-4-(4-methylpiperazin-1-yl)-2-(tetrahydropyran-4-ylamino)benzamide;

N-[5-[(3,5-difluorophenyl)methyl]-6-[(4-hydroxy-2-(trifluoromethyl)phenyl)-1H-indazol-3-yl]-4-(4-methylpiperazin-1-yl)-2-(tetrahydropyran-4-ylamino)benzamide;

N-[6-(2-aminopyrimidin-5-yl)-5-[(3,5-difluorophenyl)methyl]-1H-indazol-3-yl]-4-(4-methylpiperazin-1-yl)-2-(tetrahydropyran-4-ylamino)benzamide;

N-[6-(6-amino-3-pyridyl)-5-[(3,5-difluorophenyl)methyl]-1H-indazol-3-yl]-4-(4-methylpiperazin-1-yl)-2-(tetrahydropyran-4-ylamino)benzamide;

N-[6-(5-amino-3-pyridyl)-5-[(3,5-difluorophenyl)methyl]-1H-indazol-3-yl]-4-(4-methylpiperazin-1-yl)-2-(tetrahydropyran-4-ylamino)benzamide;

N-[5-[(3,5-difluorophenyl)methyl]-6-[(3-(hydroxymethyl)phenyl)-1H-indazol-3-yl]-4-(4-methylpiperazin-1-yl)-2-(tetrahydropyran-4-ylamino)benzamide;

N-[6-(6-amino-4-methyl-3-pyridyl)-5-[(3,5-difluorophenyl)methyl]-1H-indazol-3-yl]-4-(4-methylpiperazin-1-yl)-2-(tetrahydropyran-4-ylamino)benzamide;

N-[5-[(3,5-difluorophenyl)methyl]-6-[1-(2-hydroxy-1,1-dimethyl-ethyl)pyrazol-4-yl]-1H-indazol-3-yl]-4-(4-methylpiperazin-1-yl)-2-(tetrahydropyran-4-ylamino)benzamide;

N-[5-[(3,5-difluorophenyl)methyl]-6-(2-oxo-1H-pyridin-4-yl)-1H-indazol-3-yl]-4-(4-methylpiperazin-1-yl)-2-(tetrahydropyran-4-ylamino)benzamide;

N-[5-[(3,5-difluorophenyl)methyl]-6-(3H-imidazo[4,5-b]pyridin-6-yl)-1H-indazol-3-yl]-4-(4-methylpiperazin-1-yl)-2-(tetrahydropyran-4-ylamino)benzamide;

N-[5-[(3,5-difluorophenyl)methyl]-6-(1H-pyrazol-4-yl)-1H-indazol-3-yl]-4-(4-methylpiperazin-1-yl)-2-(tetrahydropyran-4-ylamino)benzamide;

N-[5-[(3,5-difluorophenyl)methyl]-6-(3-fluoro-5-hydroxy-phenyl)-1H-indazol-3-yl]-4-(4-methylpiperazin-1-yl)-2-(tetrahydropyran-4-ylamino)benzamide;

N-[5-[(3,5-difluorophenyl)methyl]-6-[4-(methylcarbamoyl)phenyl]-1H-indazol-3-yl]-4-(4-methylpiperazin-1-yl)-2-(tetrahydropyran-4-ylamino)benzamide;

N-[5-[(3,5-difluorophenyl)methyl]-6-[4-hydroxy-3-methyl-phenyl)-1H-indazol-3-yl]-4-(4-methylpiperazin-1-yl)-2-(tetrahydropyran-4-ylamino)benzamide;

N-[5-[(3,5-difluorophenyl)methyl]-6-(6-hydroxy-3-pyridyl)-1H-indazol-3-yl]-4-(4-methylpiperazin-1-yl)-2-(tetrahydropyran-4-ylamino)benzamide;

N-[5-[(3,5-difluorophenyl)methyl]-6-phenyl-1H-indazol-3-yl]-4-(4-methylpiperazin-1-yl)-2-(tetrahydropyran-4-ylamino)benzamide;

N-[5-[(3,5-difluorophenyl)methyl]-6-(3-methoxyphenyl)-1H-indazol-3-yl]-4-(4-methylpiperazin-1-yl)-2-(tetrahydropyran-4-ylamino)benzamide;

N-[5-[(3,5-difluorophenyl)methyl]-6-(3-fluoro-4-hydroxy-phenyl)-1H-indazol-3-yl]-4-(4-methylpiperazin-1-yl)-2-(tetrahydropyran-4-ylamino)benzamide;

N-[5-[(3,5-difluorophenyl)methyl]-6-(1H-indazol-5-yl)-1H-indazol-3-yl]-4-(4-methylpiperazin-1-yl)-2-(tetrahydropyran-4-ylamino)benzamide;

N-[5-[(3,5-difluorophenyl)methyl]-6-pyrimidin-5-yl-1H-indazol-3-yl]-4-(4-methylpiperazin-1-yl)-2-(tetrahydropyran-4-ylamino)benzamide;

N-[5-[(3,5-difluorophenyl)methyl]-6-(3-oxoisoindolin-5-yl)-1H-indazol-3-yl]-4-(4-methylpiperazin-1-yl)-2-(tetrahydropyran-4-ylamino)benzamide;

N-[5-[(3,5-difluorophenyl)methyl]-6-(1H-pyrrolo[2,3-b]pyridin-5-yl)-1H-indazol-3-yl]-4-(4-methylpiperazin-1-yl)-2-(tetrahydropyran-4-ylamino)benzamide;

N-[5-[(3,5-difluorophenyl)methyl]-6-(4-pyridyl)-1H-indazol-3-yl]-4-(4-methylpiperazin-1-yl)-2-(tetrahydropyran-4-ylamino)benzamide;

N-[5-[(3,5-difluorophenyl)methyl]-6-(3-pyridyl)-1H-indazol-3-yl]-4-(4-methylpiperazin-1-yl)-2-(tetrahydropyran-4-ylamino)benzamide;

N-[5-[(3,5-difluorophenyl)methyl]-6-[4-(1-hydroxy-1-methyl-ethyl)phenyl]-1H-indazol-3-yl]-4-(4-methylpiperazin-1-yl)-2-(tetrahydropyran-4-ylamino)benzamide;

N-[5-[(3,5-difluorophenyl)methyl]-6-(4-hydroxyphenyl)-1H-indazol-3-yl]-4-(4-methylpiperazin-1-yl)-benzamide;

N-[5-[(3,5-difluorophenyl)methyl]-6-(4-hydroxy-2-methyl-phenyl)-1H-indazol-3-yl]-4-(4-methylpiperazin-1-yl)benzamide;

N-[5-[(3,5-difluorophenyl)methyl]-6-(1H-indazol-5-yl)-1H-indazol-3-yl]-4-(4-methylpiperazin-1-yl)benzamide;

N-[6-(2-aminopyrimidin-5-yl)-5-[(3,5-difluorophenyl)methyl]-1H-indazol-3-yl]-4-(4-methylpiperazin-1-yl)benzamide;

N-[5-[(3,5-difluorophenyl)methyl]-6-(4-hydroxy-3-methyl-phenyl)-1H-indazol-3-yl]-4-(4-methylpiperazin-1-yl)benzamide;

N-[5-[(3-fluorophenyl)methyl]-6-(4-hydroxyphenyl)-1H-indazol-3-yl]-4-(4-methylpiperazin-1-yl)-2-(tetrahydropyran-4-ylamino)benzamide;

N-[6-(3-fluoro-4-hydroxy-phenyl)-5-[(3-fluorophenyl)methyl]-1H-indazol-3-yl]-4-(4-methylpiperazin-1-yl)-2-(tetrahydropyran-4-ylamino)benzamide;

N-[6-(2-fluoro-4-hydroxy-phenyl)-5-[(3-fluorophenyl)methyl]-1H-indazol-3-yl]-4-(4-methylpiperazin-1-yl)-2-(tetrahydropyran-4-ylamino)benzamide;

N-[6-(2-aminopyrimidin-5-yl)-5-[(3-fluorophenyl)methyl]-1H-indazol-3-yl]-4-(4-methylpiperazin-1-yl)benzamide;

N-[6-(3-fluoro-4-hydroxy-phenyl)-5-[(3-fluorophenyl)methyl]-1H-indazol-3-yl]-2-(2-methoxyethylamino)-4-(4-methylpiperazin-1-yl)benzamide;

3-[3-amino-5-[(3,5-difluorophenyl)methyl]-1H-indazol-6-yl]-4-methyl-phenol;

4-[3-amino-5-[(3,5-difluorophenyl)methyl]-1H-indazol-6-yl]phenol

N-[5-[(3,5-difluorophenyl)methyl]-6-(4-hydroxyphenyl)-1H-indazol-3-yl]-4-piperazin-1-yl-2-(tetrahydropyran-4-ylamino)benzamide;

N-[5-[(3,5-difluorophenyl)methyl]-6-(3-hydroxyphenyl)-1H-indazol-3-yl]-4-piperazin-1-yl-2-(tetrahydropyran-4-ylamino)benzamide;

N-[5-[(3,5-difluorophenyl)methyl]-6-(5-hydroxy-2-methyl-phenyl)-1H-indazol-3-yl]-4-piperazin-1-yl-2-(tetrahydropyran-4-ylamino)benzamide;

N-[5-[(3,5-difluorophenyl)methyl]-6-(4-hydroxy-2-methyl-phenyl)-1H-indazol-3-yl]-4-piperazin-1-yl-2-(tetrahydropyran-4-ylamino)benzamide;

N-[5-[(3-fluorophenyl)methyl]-6-(4-hydroxyphenyl)-1H-indazol-3-yl]-4-piperazin-1-yl-2-(tetrahydropyran-4-ylamino)benzamide;

N-[5-[(3,5-difluorophenyl)methyl]-6-(4-hydroxyphenyl)-1H-indazol-3-yl]-4-piperazin-1-yl-benzamide;

N-[5-[(3,5-difluorophenyl)methyl]-6-(2-oxo-1H-pyridin-4-yl)-1H-indazol-3-yl]-4-piperazin-1-yl-2-(tetrahydropyran-4-ylamino)benzamide;

N-[5-[(3,5-difluorophenyl)methyl]-6-[1-(2-hydroxy-1,1-dimethyl-ethyl)pyrazol-4-yl]-1H-indazol-3-yl]-4-piperazin-1-yl-2-(tetrahydropyran-4-ylamino)benzamide;

N-[5-[(3,5-difluorophenyl)methyl]-6-(1H-pyrazol-4-yl)-1H-indazol-3-yl]-4-piperazin-1-yl-2-(tetrahydropyran-4-ylamino)benzamide;

N-[5-[(3,5-difluorophenyl)methyl]-6-(2-fluoro-4-hydroxy-phenyl)-1H-indazol-3-yl]-4-piperazin-1-yl-2-(tetrahydropyran-4-ylamino)benzamide;

N-[5-[(3,5-difluorophenyl)methyl]-6-(4-hydroxy-2-methyl-phenyl)-1H-indazol-3-yl]-4-piperazin-1-yl-benzamide;

N-[5-[(3,5-difluorophenyl)methyl]-6-(1H-indazol-5-yl)-1H-indazol-3-yl]-4-piperazin-1-yl-benzamide;

N-[5-[(3,5-difluorophenyl)methyl]-6-(3-fluoro-5-hydroxy-phenyl)-1H-indazol-3-yl]-4-piperazin-1-yl-2-(tetrahydropyran-4-ylamino)benzamide;

N-[5-[(3,5-difluorophenyl)methyl]-6-(2-fluoro-5-hydroxy-phenyl)-1H-indazol-3-yl]-4-piperazin-1-yl-2-(tetrahydropyran-4-ylamino)benzamide;

N-[6-(2-aminopyrimidin-5-yl)-5-[(3,5-difluorophenyl)methyl]-1H-indazol-3-yl]-4-piperazin-1-yl-2-(tetrahydropyran-4-ylamino)benzamide;

N-[5-[(3,5-difluorophenyl)methyl]-6-(3H-imidazo[4,5-b]pyridin-6-yl)-1H-indazol-3-yl]-4-piperazin-1-yl-2-(tetrahydropyran-4-ylamino)benzamide;

N-[6-(5-amino-3-pyridyl)-5-[(3,5-difluorophenyl)methyl]-1H-indazol-3-yl]-4-piperazin-1-yl-2-(tetrahydropyran-4-ylamino)benzamide;

N-[6-(6-amino-3-pyridyl)-5-[(3,5-difluorophenyl)methyl]-1H-indazol-3-yl]-4-piperazin-1-yl-2-(tetrahydropyran-4-ylamino)benzamide;

N-[6-(6-amino-4-methyl-3-pyridyl)-5-[(3,5-difluorophenyl)methyl]-1H-indazol-3-yl]-4-piperazin-1-yl-2-(tetrahydropyran-4-ylamino)benzamide;

N-[5-[(3,5-difluorophenyl)methyl]-6-[4-(methylcarbamoyl)phenyl]-1H-indazol-3-yl]-4-piperazin-1-yl-2-(tetrahydropyran-4-ylamino)benzamide;

N-[5-[(3,5-difluorophenyl)methyl]-6-[3-(hydroxymethyl)phenyl]-1H-indazol-3-yl]-4-piperazin-1-yl-2-(tetrahydropyran-4-ylamino)benzamide;

N-[5-[(3,5-difluorophenyl)methyl]-6-[4-hydroxy-2-(trifluoromethyl)phenyl]-1H-indazol-3-yl]-4-piperazin-1-yl-2-(tetrahydropyran-4-ylamino)benzamide;

N-[5-[(3,5-difluorophenyl)methyl]-6-[4-hydroxy-3-methyl-phenyl]-1H-indazol-3-yl]-4-piperazin-1-yl-2-(tetrahydropyran-4-ylamino)benzamide;

N-[5-[(3,5-difluorophenyl)methyl]-6-(1H-pyrrolo[2,3-b]pyridin-5-yl)-1H-indazol-3-yl]-4-piperazin-1-yl-2-(tetrahydropyran-4-ylamino)benzamide;

N-[5-[(3,5-difluorophenyl)methyl]-6-(6-hydroxy-3-pyridyl)-1H-indazol-3-yl]-4-piperazin-1-yl-2-(tetrahydropyran-4-ylamino)benzamide;

N-[5-[(3,5-difluorophenyl)methyl]-6-phenyl-1H-indazol-3-yl]-4-piperazin-1-yl-2-(tetrahydropyran-4-ylamino)benzamide;

N-[5-[(3,5-difluorophenyl)methyl]-6-(3-methoxyphenyl)-1H-indazol-3-yl]-4-piperazin-1-yl-2-(tetrahydropyran-4-ylamino)benzamide;

N-[5-[(3,5-difluorophenyl)methyl]-6-(3-fluoro-4-hydroxy-phenyl)-1H-indazol-3-yl]-4-piperazin-1-yl-2-(tetrahydropyran-4-ylamino)benzamide;

N-[5-[(3,5-difluorophenyl)methyl]-6-(1H-indazol-5-yl)-1H-indazol-3-yl]-4-piperazin-1-yl-2-(tetrahydropyran-4-ylamino)benzamide;

N-[5-[(3,5-difluorophenyl)methyl]-6-pyrimidin-5-yl-1H-indazol-3-yl]-4-piperazin-1-yl-2-(tetrahydropyran-4-ylamino)benzamide;

N-[5-[(3,5-difluorophenyl)methyl]-6-(3-oxoisoindolin-5-yl)-1H-indazol-3-yl]-4-piperazin-1-yl-2-(tetrahydropyran-4-ylamino)benzamide;

N-[6-(2-aminopyrimidin-5-yl)-5-[(3,5-difluorophenyl)methyl]-1H-indazol-3-yl]-4-piperazin-1-yl-benzamide;

N-[6-(3-fluoro-4-hydroxy-phenyl)-5-[(3-fluorophenyl)methyl]-1H-indazol-3-yl]-2-(2-methoxyethylamino)-4-piperazin-1-yl-benzamide;

N-[5-[(3,5-difluorophenyl)methyl]-6-(4-pyridyl)-1H-indazol-3-yl]-4-piperazin-1-yl-2-(tetrahydropyran-4-ylamino)benzamide;

N-[5-[(3,5-difluorophenyl)methyl]-6-(3-pyridyl)-1H-indazol-3-yl]-4-piperazin-1-yl-2-(tetrahydropyran-4-ylamino)benzamide;

N-[6-(3-fluoro-4-hydroxy-phenyl)-5-[(3-fluorophenyl)methyl]-1H-indazol-3-yl]-4-piperazin-1-yl-2-(tetrahydropyran-4-ylamino)benzamide;

N-[6-(2-fluoro-4-hydroxy-phenyl)-5-[(3-fluorophenyl)methyl]-1H-indazol-3-yl]-4-piperazin-1-yl-2-(tetrahydropyran-4-ylamino)benzamide;

N-[5-[(3,5-difluorophenyl)methyl]-6-[4-(1-hydroxy-1-methyl-ethyl)phenyl]-1H-indazol-3-yl]-4-piperazin-1-yl-2-(tetrahydropyran-4-ylamino)benzamide;

N-[5-[(3,5-difluorophenyl)methyl]-6-(4-hydroxy-3-methyl-phenyl)-1H-indazol-3-yl]-4-piperazin-1-yl-benzamide;

N-[6-(2-aminopyrimidin-5-yl)-5-[(3-fluorophenyl)methyl]-1H-indazol-3-yl]-4-piperazin-1-yl-benzamide;

3-amino-5-(2,4-difluorobenzyl)-6-(4-hydroxyphenyl)-1H-indazole;

3-amino-5-(2,6-difluorobenzyl)-6-(4-hydroxyphenyl)-1H-indazole 3-amino-5-(2,5-difluorobenzyl)-6-(4-hydroxyphenyl)-1H-indazole;

3-amino-5-(2,5-dimethylbenzyl)-6-(4-hydroxyphenyl)-1H-indazole;

3-amino-5-(2,5-dichlorobenzyl)-6-(4-hydroxyphenyl)-1H-indazole;

3-amino-5-(3,5-dichlorobenzyl)-6-(4-hydroxyphenyl)-1H-indazole;

3-amino-5-(2,6-dichlorobenzyl)-6-(4-hydroxyphenyl)-1H-indazole;

3-amino-5-(3-fluorobenzyl)-6-(4-hydroxyphenyl)-1H-indazole;

3-[3-amino-5-[(2,4-difluorophenyl)methyl]-1H-indazol-6-yl]-4-methyl-phenol;

3-[3-amino-5-[(2,5-difluorophenyl)methyl]-1H-indazol-6-yl]-4-methyl-phenol;

3-[3-amino-5-[(2,5-dimethylphenyl)methyl]-1H-indazol-6-yl]-4-methyl-phenol;

3-[3-amino-5-[(2,5-dichlororophenyl)methyl]-1H-indazol-6-yl]-4-methyl-phenol;

3-[3-amino-5-[(3,5-dichlorophenyl)methyl]-1H-indazol-6-yl]-4-methyl-phenol;

3-[3-amino-5-[(2,6-dichlorophenyl)methyl]-1H-indazol-6-yl]-4-methyl-phenol;

3-[3-amino-5-[(3-fluorophenyl)methyl]-1H-indazol-6-yl]-4-methyl-phenol;

[5-[(2,4-difluorophenyl)methyl]-6-(4-hydroxyphenyl)-1H-indazol-3-yl]-4-(4-methylpiperazin-1-yl)-2-(tetrahydropyran-4-ylamino)benzamide;

N-[5-[(2,6-difluorophenyl)methyl]-6-(4-hydroxyphenyl)-1H-indazol-3-yl]-4-(4-methylpiperazin-1-yl)-2-(tetrahydropyran-4-ylamino)benzamide;

N-[5-[(2,3-difluorophenyl)methyl]-6-(4-hydroxyphenyl)-1H-indazol-3-yl]-4-(4-methylpiperazin-1-yl)-2-(tetrahydropyran-4-ylamino)benzamide;

N-[5-[(2,5-difluorophenyl)methyl]-6-(4-hydroxyphenyl)-1H-indazol-3-yl]-4-(4-methylpiperazin-1-yl)-2-(tetrahydropyran-4-ylamino)benzamide;

N-[5-[(2,5-dimethylphenyl)methyl]-6-(4-hydroxyphenyl)-1H-indazol-3-yl]-4-(4-methylpiperazin-1-yl)-2-(tetrahydropyran-4-ylamino)benzamide;

N-[5-[(3,5-dimethylphenyl)methyl]-6-(4-hydroxyphenyl)-1H-indazol-3-yl]-4-(4-methylpiperazin-1-yl)-2-(tetrahydropyran-4-ylamino)benzamide;

N-[5-[(2,5-dichlorophenyl)methyl]-6-(4-hydroxyphenyl)-1H-indazol-3-yl]-4-(4-methylpiperazin-1-yl)-2-(tetrahydropyran-4-ylamino)benzamide;

N-[5-[(3,4-dichlorophenyl)methyl]-6-(4-hydroxyphenyl)-1H-indazol-3-yl]-4-(4-methylpiperazin-1-yl)-2-(tetrahydropyran-4-ylamino)benzamide;

N-[5-[(3,5-dichlorophenyl)methyl]-6-(4-hydroxyphenyl)-1H-indazol-3-yl]-4-(4-methylpiperazin-1-yl)-2-(tetrahydropyran-4-ylamino)benzamide;

N-[5-[(2,3-dichlorophenyl)methyl]-6-(4-hydroxyphenyl)-1H-indazol-3-yl]-4-(4-methylpiperazin-1-yl)-2-(tetrahydropyran-4-ylamino)benzamide and pharmaceutically acceptable salts thereof.

12. A pharmaceutical composition containing a compound according to claim 1 in mixture with a pharmaceutically acceptable.

13. Method of treating conditions which benefit of modulation of biological activity of proteins kinases with the composition according to claim 12 in subjects in need thereof, said method comprising administering to said subjects pharmaceutically effective amounts of said composition, wherein the protein kinases are selected from the group consisting of ALK, DDR2, DDR1, EPHB2, TRKA, TRKB, TRKC, LTK, HCK, RET, TYK2, ROS1, JAK1, JAK2, JAK3, SRC, LYN, FYN, TXK, PKC6, FGR and their mutated and rearranged forms.

14. The method according to claim 13, wherein the protein kinase is ALK, or ALK harboring at least one mutation selected from L1196M, C1156Y, G1269A, L1152R, F1174V, S1206Y and F1174L.

15. The method according to claim 13, wherein said conditions are selected from the group consisting of tumors, inflammatory diseases, autoimmune diseases and neurodegenerative diseases.

16. The method as claimed in claim 15, wherein the tumors are selected from the group consisting of neuroblastoma, rhabdomyosarcoma, glioblastoma, inflammatory myofibroblastic tumor, melanoma, mammary carcinoma, Ewing's sarcoma, retinoblastoma, diffuse B cell lymphoma, large B cell anaplastic lymphoma, squamous cell carcinoma, thyroid carcinoma, pancreatic carcinoma, prostate carcinoma and non-small cell lung carcinoma; and the neurodegenerative disease is Alzheimer's or Parkinson disease.

\* \* \* \* \*